(12) United States Patent
Walewski et al.

(10) Patent No.: US 10,912,816 B2
(45) Date of Patent: Feb. 9, 2021

(54) OBESITY-RELATED GENES AND THEIR PROTEINS AND USES THEREOF

(71) Applicant: THE TRUSTEES OF COLUMBIA UNIVERSITY IN THE CITY OF NEW YORK, New York, NY (US)

(72) Inventors: José Leonardo Walewski, New York, NY (US); Paul David Berk, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/863,181

(22) Filed: Apr. 15, 2013

(65) Prior Publication Data

US 2013/0274181 A1 Oct. 17, 2013

Related U.S. Application Data

(63) Continuation-in-part of application No. PCT/US2011/056417, filed on Oct. 14, 2011.

(60) Provisional application No. 61/393,634, filed on Oct. 15, 2010.

(51) Int. Cl.
| | | |
|---|---|---|
| *A61K 38/04* | (2006.01) | |
| *A61K 38/10* | (2006.01) | |
| *A61K 38/17* | (2006.01) | |
| *A61K 38/22* | (2006.01) | |
| *C07K 7/08* | (2006.01) | |
| *C07K 11/00* | (2006.01) | |
| *A61P 3/04* | (2006.01) | |
| *C12Q 1/6883* | (2018.01) | |

(52) U.S. Cl.
CPC .......... *A61K 38/1709* (2013.01); *A61K 38/04* (2013.01); *A61K 38/10* (2013.01); *A61K 38/22* (2013.01); *C07K 11/00* (2013.01); *C12Q 1/6883* (2013.01); *A61P 3/04* (2018.01); *C07K 7/08* (2013.01); *C12Q 2600/118* (2013.01); *C12Q 2600/158* (2013.01)

(58) Field of Classification Search
CPC .... A61K 38/04; A61K 38/10; A61K 38/1709; A61K 38/22; A61P 3/04; C07K 7/08; C07K 14/575; C07K 11/00
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,683,195 A | 7/1987 | Mullis et al. |
| 4,683,202 A | 7/1987 | Mullis |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,236,838 A | 8/1993 | Rasmussen et al. |
| 5,252,479 A | 10/1993 | Srivastava |
| 5,328,470 A | 7/1994 | Nabel et al. |
| 5,354,556 A | 10/1994 | Sparks et al. |
| 5,391,377 A | 2/1995 | Barnwell |
| 5,580,757 A | 12/1996 | Desnick et al. |
| 5,591,767 A | 1/1997 | Mohr et al. |
| 5,639,476 A | 6/1997 | Oshlack et al. |
| 5,674,533 A | 10/1997 | Santus et al. |
| 5,712,171 A | 1/1998 | Zambias et al. |
| 5,733,566 A | 3/1998 | Lewis |
| 5,747,469 A | 5/1998 | Roth et al. |
| 5,851,995 A | 12/1998 | Basinski et al. |
| 5,879,680 A | 3/1999 | Ginns et al. |
| 6,017,524 A | 1/2000 | Roth et al. |
| 6,083,725 A | 7/2000 | Selden et al. |
| 6,143,290 A | 11/2000 | Zhang et al. |
| 6,188,045 B1 | 2/2001 | Hansen et al. |
| 6,210,666 B1 | 4/2001 | Miyamura |
| 6,395,884 B1 | 5/2002 | Selden et al. |
| 6,410,010 B1 | 6/2002 | Zhang et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,511,847 B1 | 1/2003 | Zhang et al. |
| 7,148,342 B2 | 12/2006 | Tolentino et al. |
| 7,294,504 B1 | 11/2007 | Wang |
| 7,422,896 B1 | 9/2008 | Wang |
| 7,951,382 B2 | 5/2011 | Gelber et al. |
| 2002/0000069 A1 | 1/2002 | McNamara |
| 2002/0077313 A1 | 6/2002 | Clayman |
| 2002/0173478 A1 | 11/2002 | Gewirtz |
| 2005/0221359 A1* | 10/2005 | Hsueh et al. ...................... 435/6 |
| 2005/0238639 A1 | 10/2005 | Conrad et al. |
| 2007/0072204 A1 | 3/2007 | Hannon et al. |
| 2008/0015265 A1 | 1/2008 | Rubin et al. |
| 2008/0261913 A1 | 10/2008 | Sommadossi et al. |
| 2010/0113473 A1 | 5/2010 | Player et al. |
| 2010/0184638 A1 | 7/2010 | Wynick |
| 2014/0087426 A1 | 3/2014 | Liu et al. |

FOREIGN PATENT DOCUMENTS

| | | |
|---|---|---|
| WO | WO-93/20242 | 10/1993 |
| WO | WO-95/18972 | 7/1995 |
| WO | WO-96/22529 | 7/1996 |
| WO | WO-99/07409 | 2/1999 |
| WO | WO-99/32619 A1 | 7/1999 |

(Continued)

OTHER PUBLICATIONS

Ceschi, M. et al. Epidemiology and pathophysiology of obesity as a cause of cancer. Swiss Med. Weekly, 2007, vol. 137, p. 50-56.*

(Continued)

*Primary Examiner* — Joanna Hama
*Assistant Examiner* — Bruce D. Hissong
(74) *Attorney, Agent, or Firm* — Wilmer Cutler Pickering Hale and Dorr LLP

(57) ABSTRACT

The invention provides for methods of treating obesity or an obesity-associated disorder.

26 Claims, 22 Drawing Sheets

Specification includes a Sequence Listing.

(56) References Cited

FOREIGN PATENT DOCUMENTS

| WO | WO-00/01846 | | 1/2000 |
|----|----|----|----|
| WO | WO-00/44895 | | 8/2000 |
| WO | WO-00/44914 | | 8/2000 |
| WO | WO-01/29058 | A1 | 4/2001 |
| WO | WO-01/36646 | | 5/2001 |
| WO | WO-2005/040205 | A1 | 5/2005 |
| WO | WO2006/017171 | * | 2/2006 |
| WO | WO-2006017171 | A2 | 2/2006 |
| WO | WO-2012/042455 | A1 | 4/2012 |
| WO | WO-2012/051567 | A2 | 4/2012 |

OTHER PUBLICATIONS

Tsoukas, M.A. et al. Leptin in congenetial and HIV-associated lipodystrophy. Metabolism Clinical and Experimental, 2015, vol. 64, p. 47-59.*

Kus, I., et al. Pinealectomy increases and exogenous melatonin decrases leptin production in rat anterior pituitary cells: an immunohistochemical study. Physiol. Res., 2004, 53:403-408.*

Abate N, "Obesity and cardiovascular disease Pathogenetic role of the metabolic syndrome and therapeutic implications" J Diabetes Complications, 2000, 14(3):154-74.

Abumrad NA, Park JH, Park CR. Permeation of long-chain fatty acid into adipocytes. Kinetics, specificity, and evidence for involvement of a membrane protein. J Biol Chem. Jul. 25, 1984;259(14):8945-8953.

Abumrad, N.A., et al., Mechanism of long chain fatty acid permeation in the isolated adipocyte. J Biol Chem, 1981. 256(17): p. 9183-91.

Ahima RS and SY Osei, "Leptin Signaling." Physio Behav, 2004, 81:223-41.

Allison, D.B., et al., Annual deaths attributable to obesity in the United States. JAMA, 1999. 282(16): p. 1530-38.

Altaras et al., Production and formulation of adenovirus vectors, Adv Biochem Eng Biotechnol. 2005;99:193-260.

Anderson et al., Human gene therapy. Science 256:808-813 (1992).

Anderson, Human gene therapy, Nature, supplement to vol. 392, No. 6679, pp. 25-30 (1998).

Ashburner M, Ball CA, Blake JA, Botstein D, Butler H, Cherry JM, Davis AP, Dolinski K, Dwight SS, Eppig JT, Harris MA, Hill DP, Issel-Tarver L, Kasarskis A,Lewis S, Matese JC, Richardson JE, Ringwald M, Rubin GM, Sherlock G. Gene ontology: tool for the unification of biology. The Gene Ontology Consortium. Nat Genet. 2000; 25(1):25-29, 9 pages.

Atherton et al., (1989) *Solid Phase Peptide Synthesis: a Practical Approach*. IRL Press, Oxford, England, 7 pages.

Ausubel FM, ed., Current Protocols in Molecular Biology, John Wiley & Sons, Inc., New York, 1989; 17 pgs.

Bachman, K.H., Obesity, weight management, and health care costs: a primer. Dis Manag, 2007. 10(3): p. 129-37.

Balistreri, C.R., C. Caruso, and G. Candore, The role of adipose tissue and adipokines in obesity-related inflammatory diseases. Mediators Inflamm, 2010. 2010: 802078, 19 pages.

Bandyopadhyay PK, Temin HM. Expression from an internal AUG codon of herpes simplex thymidine kinase gene inserted in a retrovirus vector. Mol Cell Biol. Apr. 1984;4(4):743-8.

Bardag-Gorce F, Oliva J, Dedes J, Li J, French BA, French SW. Chronic ethanol feeding alters hepatocyte memory which is not altered by acute feeding. Alcohol Clin Exp Res. 2009;33(4):684-692, 20 pages.

Barringer et al., Blunt-end and single-strand ligations by *Escherichia coli* ligase: influence on an in vitro amplification scheme. Gene 89:117-122, 1990.

Bass, B.L., "RNA interference: the short answer," Nature, 2001,vol. 411, pp. 428-429.

Bayoumi, R et al. "Some Genetic Determinants of Obesity, Type 2 Diabetes and Dyslipidemias in "Oman Family Study"" Genetic Disorders in the Arab World, 2008, 68-77.

Bays, Current and Investigational Antiobesity Agents and Obesity Therapeutic Treatment Targets (2004) Obesity Research 12(8):1197-1211.

Beck et al., "Strategies and challenges for the next generation of therapeutic antibodies." Nat Rev Immunol. May 2010;10(5):345-52.

Benjamini, Y. and Hochberg, Y. (1995). "Controlling the False Discovery Rate: a Practical and Powerful Approach to Multiple Testing," Journal of the Royal Statistical Society B, 1995; 57, 289-300.

Berg CE et al., "Rapamycin partially prevents insulin resistance induced by chronic insulin treatment." Biochem Biophys Res Commun, 2002, 293(3):1021-7.

Berger, Preparation of cDNA and the generation of cDNA libraries: overview. Methods Enzymol. 152:307-316, 1987.

Berk PD, Stump DD. Mechanisms of cellular uptake of long chain free fatty acids. Mol Cell Biochem. Feb. 1999;192(1-2):17-31.

Berk PD, Zhou S, Kiang C, Stump DD, Fan X, Bradbury MW. Selective up-regulation of fatty acid uptake by adipocytes characterizes both genetic and diet-induced obesity in rodents. J Biol Chem. 1999; 274(40):28626-28631.

Berk PD, Zhou SL, Bradbury M, Stump D, Kiang CL, Isola LM. Regulated membrane transport of free fatty acids in adipocytes: role in obesity and non-insulin dependent diabetes mellitus. Trans Am Clin Climatol Assoc. 1997;108:26-43.

Berk PD, Zhou SL, Kiang CL, Stump D, Bradbury M, Isola LM. Uptake of long chain free fatty acids is selectively up-regulated in adipocytes of Zucker rats with genetic obesity and noninsulin dependent diabetes mellitus. J Biol Chem.1997; 272(13): 8830-8835.

Berk PD. The Masters Perspective: Regulatable fatty acid transport mechanisms are central to the pathophysiology of obesity, fatty liver, & metabolic syndrome. Hepatol 2008; 48: 1362-1376, 26 pages.

Berkner et al. Development of Adenovirus Vectors for the Expression of Heterologous Genes Biotechniques. Jul.-Aug. 1988;6(7):616-29.

Berkner. Expression of Heterologous Sequences in Adenoviral Vectors. Curr Top Microbiol Immunol. 1992;158:39-66.

Berman DM, et al., "Racial Disparities in Metabolism, Central Obesity, and Sex Hormone-Binding Globulin in Postmenopausal Women." J Clin Endocrinol Metab, 2001, 86(1):97-103.

Berman, M. and M. Weiss, Users Manual for SAAM U.S. Public Health Service Publication 1703. , D.o.H.a.H. Services, Editor 1967: Washington, DC. 174 pages.

Blondelle, S.E., et al., "Novel antimicrobial compounds indentified using synthetic combinatorial library technology," Tib Tech, 1996, vol. 14, p. 60-65.

Bojesen IN & Bojesen E. Binding of arachidonate and oleate to bovine serum albumin. J Lipid Res 1994; 35: 770-778.

Bouche C, et al., "The Cellular Fate of Glucose and Its Relevance in Type 2 Diabetes." Endoc Rev, 2004, 25(5): 807-830.

Bradbury MW, Berk PD. Lipid metabolism in hepatic steatosis. Clin Liver Dis. 2004; 8(3): 639-671.

Bray, G. A., "1989 McCollum Award Lecture. Genetic and hypothalamic mechanisms for obesity—finding the needle in the haystack." 1989, Amer. J. Clin. Nutr. 5:891-902.

Bray, G. A., "Genetic, hypothalamic and endocrine features of clinical and experimental obesity." 1992, Prog. Brain Res. 93:333-341.

Bray, G.A., Medical consequences of obesity. J Clin Endocrinol Metab, 2004. 89(6): p. 2583-9.

Brenner et al., "Encoded combinatorial chemistry." (1992) Proc. Natl. Acad. Sci. USA 89:5381-5383.

Brower, Naked DNA vaccines come of age. Nature Biotechnology, 16:1304-1305 (1998).

Brunner L et al., "Leptin is a physiologically important regulator of food intake." Obes Relat Metab Disord, 1997, 21(12):1152-60.

Buchschacher GL Jr1, Panganiban AT. Human immunodeficiency virus vectors for inducible expression of foreign genes. J Virol. May 1992;66(5):2731-9.

(56) References Cited

OTHER PUBLICATIONS

Buchwald et al., Long-term, continuous intravenous heparin administration by an implantable infusion pump in ambulatory patients with recurrent venous thrombosis. Surgery 88(4):507-516 (1980).
Buijs M M, Burggraaf J, Wijbrandts C, de Kam M L, Frölich M, Cohen A F, Romijn J A, Sauerwein H P, Meinders A E, and Pijl H. Blunted lipolytic response to fasting in abdominally obese women: evidence for involvement of hyposomatotropism. Am J Clin Nutr 2003;77: 544-550.
Burg et al., Single molecule detection of RNA reporter probes by amplification with Q beta replicase. Mol. Cell. Probes 10:257-271, 1996.
Calabrese, V., et al., Cellular stress responses, the hormesis paradigm, and vitagenes: novel targets for therapeutic intervention in neurodegenerative disorders. Antioxid Redox Signal, 2010. 13(11): p. 1763-811.
Caro JF, et al., "Leptin: The Tale of an Obesity Gene." Diabetes, 1996, 45(11):1455-62.
Carulli L, et al., "Review article: diabetes, genetics and ethnicity." Aliment Pharmacol Ther, 2005, 22 Suppl 2:16-9.
Celik, I., et al., Therapeutic efficacy of endostatin exhibits a biphasic dose-response curve. Cancer Res, 2005. 65(23): p. 11044-50.
Chan et al., "Therapeutic antibodies for autoimmunity and inflammation." Nat Rev Immunol. May 2010;10(5):301-16.
Chen et al., Gene therapy for brain tumors: regression of experimental gliomas by adenovirus-mediated gene transfer in vivo.1994. Proc. Natl. Acad. Sci. USA 91: 3054-3057.
Chirieac DV, Chirieac LR, Corsetti JP, Cianci J, Sparks CE, Sparks JD. Glucose-stimulated insulin secretion suppresses hepatic triglyceride-rich lipoprotein and apoB production. Am J Physiol Endocrinol Metab. 2000;279(5):E1003-1011.
Chu NF, et al., "Glycemic status and soluble tumor necrosis factor receptor levels in relation to plasma leptin concentrations among normal weight and overweight US men." Int J Obes Relat Metab Disord, 2000, 24(9):1085-92.
Considine, R.V., et al., Serum immunoreactive-leptin concentrations in normal-weight and obese humans. N Engl J Med, 1996. 334(5): p. 292-295.
Cutfield LS, et al., "Reduced Insulin Sensitivity During Growth Hormone Therapy for Short Children Born Small for Gestational Age." J Pediatr, 2003, 142(2):113-6.
Dallas et al., "RNAi: A novel antisense technology and its therapeutic potential." (2006) Med. Sci. Monit.12(4):RA67-74.
Dennis PB et al., "The Principal Rapamycin-Sensitive p70s6k Phosphorylation Sites, T-229 and T-389, Are Differentially Regulated by Rapamycin-Insensitive Kinase Kinases." Mol Cell Biol, 1996, 16(11):6242-51.
Desai AS and PT O'Gara, "Diabetes and Heart Failure: Epidemiology, Pathophysiology and Management." Indian Heart J, 2005, 57(4):295-303.
Di Girolamo, M., S. Mendlinger, and J.W. Fertig, A simple method to determine fat cell size and number in four mammalian species. Am J Physiol, 1971. 221(3): p. 850-8.
Diehl AM. Lessons from animal models of NASH. Hepatol Res. 2005;33(2):138-144.
Doniger SW, Salomonis N, Dahlquist KD, Vranizan K, Lawlor SC, Conklin BR. MAPPFinder: using Gene Ontology and GenMAPP to create a global gene-expression profile from microarray data. Genome Biol. 2003; 4(1):R7-R7.12.
During et al., Controlled release of dopamine from a polymeric brain implant: in vivo characterization. Ann. Neurol. 25(4):351-356 (1989).
Dzau et al., Gene therapy for cardiovascular disease. Trends Biotechnol 11(5):205-210 (1993).
Edens, N. K., Fried, S. K., Kral, J. G., Hirsch, J., and Leibel, R. L. In vitro lipid synthesis in human adipose tissue from three abdominal sites. Am J Physiol 1993; 265(3 Pt 1):E374-379.
Elbashir, S.M., et al., "Duplexes of 21-nucleotide RNAs mediate RNA interference in cultured mammalian cells," Nature, vol. 411, pp. 494-498, 2001.
Eliyahu et al., Polymers for DNA delivery. Molecules, 2005; 10(1):34-64.
Erb, E., et al., "Recursive deconvolution of combinatorial chemical libraries," Proc Natl Acad Sci USA, 1994, vol. 91, pp. 11422-11426.
Fan X, Bradbury MW, Berk PD. Leptin and insulin modulate nutrient partitioning and weight loss in ob/ob mice through regulation of long-chain fatty acid uptake by adipocytes. J Nutr. 2003; 133(9): 2707-2715.
Fantin VR et al., "Characterization of Insulin Receptor Substrate 4 in Human Embryonic Kidney 293 Cells." J Biol Chem, 1998, 273(17):10726-32.
Federici M and R Lauro, "Review article: diabetes and atherosclerosis—running on a common road." Aliment Pharmacol Therapy, 2005, 22(Suppl 2): 11-15.
Fink et al. "In Vivo Expression of beta-Galactosidase in Hippocampal Neurons by HSV-Mediated Gene Transfer." Hum Gene Ther. Feb. 1992;3(1):11-9.
Finkelstein, E.A., C.J. Ruhm, and K.M. Kosa, Economic causes and consequences of obesity. Annu Rev Public Health, 2005. 26: p. 239-57.
Fix JA, Oral controlled release technology for peptides: status and future prospects. Pharm Res. 13(12): 1760-1764, 1996.
Flegal, K.M., et al., Prevalence and trends in obesity among US adults, 1999-2000. JAMA, 2002. 288(14): p. 1723-27.
Fodor, S.P.A., et al., "Light-directed, spatially addressable parallel chemical synthesis," Science, 1991, vol. 251, pp. 767-773.
Freedman BI, Langefeld CD, Rich SS, Valis CJ, Sale MM, Williams AH, Brown WM, Beck SR, Hicks PJ, Bowden DW. A genome scan for ESRD in black families enriched for nondiabetic nephropathy. J Am Soc Nephrol. 2004; 15(10):2719-2127.
Freshney RI, Animal Cell Culture, A Practical Approach. IRL Press Limited, 1987, 10 pgs.
Fried, S. K. and Kral, J. G. Sex differences in regional distribution of fat cell size and lipoprotein lipase activity in morbidly obese patients. Int J Obes 1987; 11(2):129-140.
Friedman, J. M. and Liebel, R. L., "Tackling a Weighty Problem." 1992, Cell 69:217-220.
Friedman, J. M. et al., "Molecular mapping of obesity genes." 1991, Mamm. Gen. 1:130-144.
Friedmann T., Progress toward human gene therapy. Science, 244(4910):1275-1281 (1989).
Gait MJ, Oligonucleotide Synthesis, IRL Press Limited, Oxford, England (1984) 12 pgs.
Gallop, M.A., et al., "Applications of combinatorial technologies to drug discovery. 1. backgroud and peptide combinatorial libraries," J Medicinal Chemistry, 1994, vol. 37, No. 9, pp. 1233-1251.
Garaulet M, Pérez-Llamas F, Pérez-Ayala M, Martinez P, de Medina FS, Tebar FJ, Zamora S. Site-specific differences in the fatty acid composition of abdominal adipose tissue in an obese population from a Mediterranean area: relation with dietary fatty acids, plasma lipid profile, serum insulin, and central obesity. Am J Clin Nutr. 2001;74:585-591.
Ge, F., et al., Insulin- and leptin-regulated fatty acid uptake plays a key causal role in hepatic steatosis in mice with intact leptin signaling but not in ob/ob or db/db mice. Am J Physiol Gastrointest Liver Physiol, 2010. 299(4): p. G855-66, 25 pages.
Geller AI, Freese A. Infection of cultured central nervous system neurons with a defective herpes simplex virus 1 vector results in stable expression of *Escherichia coli* beta-galactosidase. Proc Natl Acad Sci U S A. Feb. 1990;87(3):1149-53.
Gillingham MB, Purnell JQ, Jordan J, Stadler D, Haqq AM, Harding CO. Effects of higher dietary protein intake on energy balance and metabolic control in children with long-chain 3-hydroxy acyl-CoA dehydrogenase (LCHAD) or trifunctional protein (TFP) deficiency. Mol Genet Metab. 2007; 90(1):64-69, 15 pages.
Glatz JF, van Nieuwenhoven FA, Luiken JJ, Schaap FG, van der Vusse GJ. Role of membrane-associated and cytoplasmic fatty acid-binding proteins in cellular fatty acid metabolism. Prostaglandins Leukot Essent Fatty Acids. Oct. 1997;57(4-5) 373-378.
Glover DN, ed., DNA Cloning, vol. I, IRL Press, Oxford, England (1985) 8 pgs.

(56) References Cited

OTHER PUBLICATIONS

Goldberg IJ, Ginsberg HN. Ins and outs modulating hepatic triglyceride and development of nonalcoholic fatty liver disease. Gastroent 2006; 130(4):1343-1346.

Gordon GJ, Jensen RV, Hsiao LL, Gullans SR, Blumenstock JE, Ramaswamy S, Richards WG, Sugarbaker DJ, Bueno R. Translation of microarray data into clinically relevant cancer diagnostic tests using gene expression ratios in lung cancer and mesothelioma. Cancer Res. Sep. 1, 2002;62(17):4963-7.

Gordon GJ, Jensen RV, Hsiao LL, Gullans SR, Blumenstock JE, Richards WG, Jaklitsch MT, Sugarbaker DJ, Bueno R. Using gene expression ratios to predict outcome among patients with mesothelioma. J Natl Cancer Inst. Apr. 16, 2003;95(8):598-605.

Gorziglia M and A Z Kapikian, Expression of the OSU rotavirus outer capsid protein VP4 by an adenovirus recombinant. J. Virol. 1992, 66(7):4407-4412.

Graves LM et al., "cAMP- and rapamycin-sensitive regulation of the association of eukaryotic iniitiation factor 4E and the translational regulator PHAS-I in aortic smooth muscle cells." Proc Natl Acad Sci U S A, 1995, 92(16):7222-6.

Guatelli et al., Isothermal, in vitro amplification of nucleic acids by a multienzyme reaction modeled after retroviral replication. Proc. Natl. Acad. Sci. USA 87:1874-1878, 1990.

Hames "Transcription and Translation", B. D. Hames & S. J. Higgins, eds. (1984), 13 pages.

Hames BD et al., Nucleic Acid Hybridization, IRL Press Limited, Oxford, England (1985) 11 pgs.

Hara K, et al., "Regulation of eIF-4E BP1 Phosphorylation by mTOR." J Biol Chem, 1997, 272(42):26457-63.

Helseth E1, Kowalski M, Gabuzda D, Olshevsky U, Haseltine W, Sodroski J. Rapid complementation assays measuring replicative potential of human immunodeficiency virus type 1 envelope glycoprotein mutants. J Virol. May 1990;64(5):2416-20.

Hansen, J.B., "Towards selective Kir6.2/SUR1 potassium channel openers, medicinal chemistry and therapeutic perspectives," Curr Med Chem, 2006, vol. 13, No. 4, pp. 361-376.

Herweijer et al., Gene therapy progress and prospects: hydrodynamic gene delivery. Gene Ther. 14(2):99-107 (2007).

Holgado-Madruga M et al., "A Grb2-associated docking protein in EGF- and insulin-receptor signalling." Nature, 1996, 379:560-4.

Houghten, R.A., et al., "Generation and use of synthetic peptide combinatorial libraries for basic research and drug discovery," Nature, 1991, vol. 354, pp. 84-86.

Houghten, R.A. et al., "The use of synthetic peptide combinatorial libraries for the identification of bioactive peptides," Biotechniques, 1992, vol. 13, p. 412-421.

Howard et al., Intracerebral drug delivery in rats with lesion-induced memory deficits. J Neurosurg. 71:105-112 (1989).

Hsueh WC, Mitchell BD, Schneider JL, et al. Genomewide scan of obesity in the Old Order Amish. J Clin Endocrinol Metab. 2001;86:1199-205.

Hudson, P.J., "Recombinant antibody fragments," Curr Opin Biotechnol, 1998, vol. 9, pp. 395-402.

Innis et al., PCR Protocols, A Guide to Methods and Applications Academic Press Inc., N.Y. (1990) 16 pgs.

Innis et al., PCR Strategies, Academic Press Inc., N.Y. (1995) 13 pgs.

Isaka et al., Electroporation-mediated gene therapy. Expert Opin Drug Deliv. 4(5):561-71 (2007).

Jager et al., Emerging adenoviral vectors for stable correction of genetic disorders. Curr Gene Ther. 7(4):272-83 (2007).

Jayawickreme, C.K., et al., "Creation and functional screening of a multi-use peptide library," Proc Natl Acad Sci USA, 1994, vol. 91, pp. 1614-1618.

Jensen et al., Cutaneous gene therapy. Ann Med. 2007;39(2):108-15.

Johnson PA, Miyanohara A, Levine F, Cahill T, Friedmann T. Cytotoxicity of a replication-defective mutant of herpes simplex virus type 1. J Virol. May 1992;66(5):2952-65.

Kalota, A., et al., "Progress in the Development of Nucleic Acid Therapeutics," Handbook Exp. Pharmacol, 2006, vol. 173, pp. 173-196.

Kampf JP, Kleinfeld AM. Fatty acid transport in adipocytes monitored by imaging intracellular free fatty acid levels. J Biol Chem. Aug. 20, 2004;279(34):35775-35780.

Kampf JP, Parmley D, Kleinfeld AM. Free fatty acid transport across adipocytes is mediated by an unknown membrane protein pump. Am J Physiol Endocrinol Metab. 2007; 293(5):E1207-1214.

Kanehisa M, Goto S, Kawashima S, Okuno Y, Hattori M. The KEGG resource for deciphering the genome. Nucleic Acids Res. 2004; 32 D277-280.

Kennedy L, Vass JK, Haggart DR, Moore S, Burczynski ME, Crowther D, Miele G. Hematopoietic Lineage Transcriptome Stability and Representation in PAXgene Collected Peripheral Blood Utilising SPIA Single-Stranded cDNA Probes for Microarray. Biomark Insights. 2008; 3:403-417.

Kikuchi et al., Cutaneous gene delivery. J Dermatol Sci. 50(2):87-98 (2008).

Kim K, Perroud B, Espinal G, Kachinskas D, Austrheim-Smith I, Wolfe B M, Warden, CH.Genes and networks expressed in perioperative omental adipose tissue are correlated with weight loss from Roux-en-Y gastric bypass. International Journal of Obesity (2008) 32: 1395-1406.

Kleinfeld AM, Kampf JP, Lechene C. Transport of 13C-oleate in adipocytes measured using multi-imaging mass spectrometry. J Am Soc Mass Spectrom. Nov. 2004;15(11):1572-1580.

Klonoff et al., Drugs in the pipeline for the obesity market. J Diabetes Sci Technol. Sep. 2008;2(5):913-8.

Kontermann, Alternative antibody formats. Curr Opin Mol Ther. Apr. 2010;12(2):176-83.

Kwoh et al., Transcription-based amplification system and detection of amplified human immunodeficiency virus type 1 with a bead-based sandwich hybridization format. Proc. Natl. Acad. Sci. USA 86(4):1173-1177 (1989).

Lago, F., et al., Adipokines as novel modulators of lipid metabolism. Trends Biochem Sci, 2009. 34(10): p. 500-10.

Lago, F., et al., The emerging role of adipokines as mediators of inflammation and immune responses. Cytokine Growth Factor Rev, 2007. 18(3-4): p. 313-25.

Lam, K.S., et al., "A new type of synthetic peptide library for identifying ligand-binding activity," Nature, 1991, vol. 354, pp. 82-84.

Landegren et al., A ligase-mediated gene detection technique. Science 241(4869):1077-1080 (1988).

Langer and Peppas, "Chemical and Physical Structure of Polymers as Carriers for Controlled Release of Bioactive Agents: A Review." J. Macromol. Sci. Rev. Macromol. Chem. 23:61-126 (1983).

Langer et al., Medical Applications of Controlled Release, vol. 2. Applications and Evaluation, CRC Press Inc., Boca Raton, Fla. (1974) 26 pgs.

Langer R, New methods of drug delivery. Science 249:1527-1533 (1990).

Langin D, Dicker A, Tavernier G, Hoffstedt J, Mairal A, Rydén M, Arner E, Sicard A, Jenkins CM, Viguerie N, van Harmelen V, Gross RW, Holm C, Arner P. Adipocyte lipases and defect of lipolysis in human obesity. Diabetes. 2005;54(11):3190-3197.

Levy et al., Inhibition of calcification of bioprosthetic heart valves by local controlled-release diphosphonate. Science 228(4696):190-192 (1985).

Li, X., et al., Intracerebroventricular leptin infusion improves glucose homeostasis in lean type 2 diabetic MKR mice via hepatic vagal and non-vagal mechanisms. PLoS One, 2011. 6(2): p. e17058, 7 pages.

Liang, N. C., N. T. Bello, and T.H. Moran, Experience with activity based anorexia enhances conditioned taste aversion learning in rats. Physiol Behav, 2011. 102(1): p. 51-7, 16 pages.

Luiken JJ, Glatz JF, Bonen A. Fatty acid transport proteins facilitate fatty acid uptake in skeletal muscle. Can J Appl Physiol. Oct. 2000;25(5):333-351.

Luiken JJ, Turcotte LP, Bonen A. Protein-mediated palmitate uptake and expression of fatty acid transport proteins in heart giant vesicles. J Lipid Res. 1999;40(6)1007-1016.

(56) References Cited

OTHER PUBLICATIONS

Lutzelberger, M., et al., "Strategies to identify potential therapeutic target sites in RNA," Handbook Exp Pharmacol, 2006, vol. 173, pp. 243-259.
Ma, L., et al., Region-specific involvement of BDNF secretion and synthesis in conditioned taste aversion memory formation. J Neurosci, 2011. 31(6): p. 2079-90, 25 pages.
Madzak C et al. "Efficient in vivo encapsidation of a shuttle vector into pseudo-simian virus 40 virions using a shuttle virus as helper." Journal of General Virology (1992) 73:1533-1536.
Mann R, Baltimore D. Varying the position of a retrovirus packaging sequence results in the encapsidation of both unspliced and spliced RNAs. J Virol. May 1985;54(2):401-7.
Mannhold,R., "Structure-activity relationships of $K_{ATP}$ channel openers," Curr Top Med Chem, 2006, vol. 6, No. 10, pp. 1031-1047.
Margolskee. "Epstein-Barr Virus Based Expression Vectors." Curr Top Microbiol Immunol. 1992;158:67-95.
Maynard, J., et al., "Antibody Engineering," Ann Rev Biomed Eng, 2008, vol. 2, pp. 339-376.
McCaffrey et al. RNA interference in adult mice. 2002, Nature, 418:38-9.
McManus and Sharp "Gene silencing in mammals by small interfering RNAs." (2002) Nat Rev Genetics, 3:737-47.
McManus et al., "Gene silencing using micro-RNA designed hairpins." 2002, RNA, 8:842-50.
Medynski, D., "Synthetic peptide combinatorial libraries," Biotechnology, 1994, vol. 12, pp. 709-710.
Miller AD, Human gene therapy comes of age. Nature, 357(6378): 455-460 (1992).
Miller AD, Law MF, Verma IM. Generation of helper-free amphotropic retroviruses that transduce a dominant-acting, methotrexate-resistant dihydrofolate reductase gene. Mol Cell Biol. Mar. 1985;5(3):431-7.
Miller AD1, Bender MA, Harris EA, Kaleko M, Gelinas RE. Design of retrovirus vectors for transfer and expression of the human beta-globin gene. J Virol. Nov. 1988;62(11):4337-45.
Mirabeau, O., et al., Identification of novel peptide hormones in the human proteome by hidden Markov model screening. Genome Res, 2007. 17(3): p. 320-7.
Moss. "Vaccinia and other poxvirus expression vectors." Curr Opin Biotechnol. Oct. 1992;3(5):518-22.
Mustelin L, Pietiläinen KH, Rissanen A, Sovijärvi AR, Piirilä P, Naukkarinen J, Peltonen L, Kaprio J, Yki-Järvinen H. Acquired obesity and poor physical fitness impair expression of genes of mitochondrial oxidative phosphorylation in monozygotic twins discordant for obesity. Am J Physiol Endocrinol Metab. 2008; 295(1):E148-54.
Muzyczka. "Use of Adeno-Associated Virus as a General Transduction Vector for Mammalian Cells." Curr Top Microbiol Immunol. 1992;158:97-129.
Myers MG, Leptin receptor signaling and the regulation of mammalian physiology. Recent Prog Horm Res, 2004, 59:287-304.
Natarajan R and JL Nadler, Lipid Inflammatory Mediators in Diabetic Vascular Disease. Arterioscler Thromb Vasc Biol, 2004, 24:1542-48.
Niswender KD, et al., Insulin and its evolving partnership with leptin in the hypothalamic control of energy homeostasis. Trends Endocr Metab, 2004, 15(8):362-9.
Oda A, et al., Leptin stimulates rat aortic smooth muscle cell proliferation and migration. Kobe J Med Sci, 2001, 47(3):141-50.
Ogden, C.L., et al., The epidemiology of obesity. Gastroenterology, 2007. 132(6): p. 2087-102.
Ohi et al. "Construction and replication of an adeno-associated virus expression vector that contains human beta-globin cDNA." Gene. May 14, 1990;89(2):279-82.
Ohlmeyer, M.H., et al., "Complex synthetic chemical libraries indexed with molecular tags," Proc Natl Acad Sci USA, 1993, vol. 90, pp. 10922-10926.

Oldridge, N., et al., Goal attainment in a randomized controlled trial of rehabilitation after myocardial infarction. J Cardiopulm Rehabil, 1999. 19(1): p. 29-34.
Olshansky, S.J., et al., A potential decline in life expectancy in the United States in the 21st century. N Engl J Med, 2005. 352(11): p. 1138-45.
Ostman, J., Arner, P., Engfeldt, P., and Kager, L. Regional differences in the control of lipolysis in human adipose tissue. Metabolism 1979; 28(12):1198-1205.
Paddison et al., "Short hairpin RNAs (shRNAs) induce sequence-specific silencing in mammalian cells." 2002, Genes Dev, 16:948-58.
Page KA, Landau NR, Littman DR. Construction and use of a human immunodeficiency virus vector for analysis of virus infectivity. J Virol. Nov. 1990;64(11):5270-6.
Patti ME, Butte AJ, Crunkhorn S, Cusi K, Berria R, Kashyap S, Miyazaki Y, Kohane I, Costello M, Saccone R, Landaker EJ, Goldfine AB, Mun E, DeFronzo R, Finlayson J, Kahn CR, Mandarino LJ. Coordinated reduction of genes of oxidative metabolism in humans with insulin resistance and diabetes: Potential role of PGC1 and NRF1. Proc Natl Acad Sci U S A. 2003; 100(14):8466-71.
Perbal B., A Practical Guide to Molecular Cloning (1984); the treatise, Methods in Enzymology (Academic Press, Inc., N.Y.); 11 pgs.
Petrescu, O., et al., Long-chain fatty acid uptake is upregulated in omental adipocytes from patients undergoing bariatric surgery for obesity. Int J Obes (Lond), 2005. 29(2): p. 196-203.
Petrescu, O., Fan, XQ, Bradbury, MW and Berk, PD, Selective regulation of long chain fatty acid uptake across adipocyte plasma membranes is a control point for body adiposity. Gastroenterology, 2003: p. A70.
Petropoulos CJ, Payne W, Salter DW, Hughes SH. Appropriate in vivo expression of a muscle-specific promoter by using avian retroviral vectors for gene transfer [corrected]. J Virol. Jun. 1992;66(6):3391-7.
Powers, K.A., S.T. Rehrig, and D.B. Jones, Financial impact of obesity and bariatric surgery. Med Clin North Am, 2007. 91(3): p. 321-38.
Puzzo, D., L. Privitera, and A. Palmeri, Hormetic effect of amyloid-beta peptide in synaptic plasticity and memory. Neurobiol Aging, 2012. 33(7): p. 1484 e15-24.
Quantin B, Perricaudet LD, Tajbakhsh S, Mandel JL. Adenovirus as an expression vector in muscle cells in vivo. Proc Natl Acad Sci U S A. Apr. 1, 1992;89(7):2581-4.
Ramakrishnan R, Dorris D, Lublinsky A, Nguyen A, Domanus M, Prokhorova A, Gieser L, Touma E, Lockner R, Tata M, Zhu X, Patterson M, Shippy R, Sendera TJ, Mazumder A. An assessment of Motorola CodeLink microarray performance for gene expression profiling applications. Nucleic Acids Res. 2002;30(7):e30, 12 pages.
Ribon V and AR Saltiel, Insulin stimulates tyrosine phosphorylation of the proto-oncogene product of c-Cbl in 3T3-L1 adipocytes .Biochem J, 1997, 324( Pt 3):839-45.
Richieri GV, Anel A & Kleinfeld AM. Interactions of long-chain fatty acids and albumin: determination of free fatty acid levels using the fluorescent probe ADIFAB. Biochemistry 1993; 32: 7574-7580.
Rose H, Conventz M, Fischer Y, Jungling E, Hennecke T & Kammermeier H. Long-chain fatty acid-binding to albumin: re-evaluation with directly measured concentrations. Biochim Biophys Acta 1994; 1215: 321-326.
Rosenfeld et al. "In Vivo Transfer of the Human Cystic Fibrosis Transmembrane Conductance Regulator Gene to the Airway Epithelium." Cell. Jan. 10, 1992;68(1):143-55.
Rucinski M, Porzionato A, Ziolkowska A, Szyszka M, Macchi V, De Caro R, Malendowicz LK. Expression of the spexin gene in the rat adrenal gland and evidences indicating that spexin inhibits adrenocortical cell proliferation. Peptides 31:676-682, 2010.
Fisher, F. M., McTernan, P. G., Valsamakis, G., Chetty, R., Harte, A. L., Anwar, A. J., Starcynski, J., Crocker, J., Barnett, A. H., McTernan, C. L., and Kumar, S. Differences in adiponectin protein expression: effect of fat depots and type 2 diabetic status. Horm Metab Res 2002; 34: 650-654.

(56) References Cited

OTHER PUBLICATIONS

Saiki A, Olsson M, Jernås M, Gummesson A, McTernan PG, Andersson J, Jacobson P, Sjöholm K, Olsson B, Yamamura S, Walley A, Froguel P, Carlsson B, Sjöström L, Svensson PA, Carlsson LM.. Tenomodulin is highly expressed in adipose tissue, increased in obesity, and down-regulated during diet-induced weight loss. J Clin Endocrinol Metab. Oct. 2009; 94(10): 3987-94.

Salmon, S.E., et al., "Discovery of biologically active peptides in random libraries: solution-phase testing after staged orthogonal release from resin beads," Proc Natl Acad Sci USA, 1993, vol. 90, pp. 11708-11712.

Samanen et al., Chemical approaches to improve the oral bioavailability of peptidergic molecules. J. Pharm. Pharmacol. 48: 119-135 (1996).

Sambrook et al., Molecular Cloning, a laboratory manual, Second Edition, vols. 1-3, Cold Spring Harbor Laboratory Press, USA (1989) 33 pgs.

Saudek et al., A preliminary trial of the programmable implantable medication system for insulin delivery. N. Engl. J. Med. 321(9):574-579 (1989).

Schwieterman W, Sorrentino D, Potter BJ, et al. Uptake of oleate by isolated rat adipocytes is mediated by a 40-kDa plasma membrane fatty acid binding protein closely related to that in liver and gut. Proc Natl Acad Sci U S A. Jan. 1988;85(2):359-363.

Sefton MV., Implantable pumps. CRC Crit. Ref. Biomed. Eng. 14(3):201-240 (1987).

Sen and Blau, "A brief history of RNAi: the silence of the genes," (2006) FASEB J., 20:1293-99.

Shi, L., Reid, L.H., Jones, W.D., Shippy, R., Warrington, J.A., Baker, S.C., Collins, P.J., de Longueville, F., Kawasaki, E.S., Lee, K.Y., et al. 2006. The MicroArray Quality Control (MAQC) project shows inter- and intraplatform reproducibility of gene expression measurements. Nat Biotechnol 24:1151-1161, 23 pages.

Shimada T1, Fujii H, Mitsuya H, Nienhuis AW. Targeted and highly efficient gene transfer into CD4+ cells by a recombinant human immunodeficiency virus retroviral vector. J Clin Invest. Sep. 1991;88(3):1043-7.

Smith et al., Detection of *Mycobacterium* turberculosis directly from sputum by using a prototype automated Q-beta replicase assay. J. Clin. Microbiol. 35:1477-1483 (1997).

Smolen et al., Controlled Drug Bioavailability, Drug Product Design and Performance, John Wiley & Sons, Inc., New York (1984) 3 pgs.

Snedecor GW & Cochran WG. Statistical methods 6th ed. Iowa State University Press: Ames, Iowa 1967, 9 pages.

Sooknanan et al., A detection and amplification system uniquely suited for RNA. Biotechnology 13:563-564 (1995).

Sorge J, Wright D, Erdman VD, Cutting AE. Amphotropic retrovirus vector system for human cell gene transfer. Mol Cell Biol. Sep. 1984;4(9):1730-7.

Sorrentino D, Robinson RB, Kiang CL & Berk PD. At physiologic albumin/oleate concentrations oleate uptake by isolated hepatocytes, cardiac myocytes, and adipocytes is a saturable function of the unbound oleate concentration. Uptake kinetics are consistent with the conventional theory. J Clin Invest 1989; 84: 1325-1333.

Sorrentino D, Stump D, Potter BJ, et al. Oleate uptake by cardiac myocytes is carrier mediated and involves a 40-kD plasma membrane fatty acid binding protein similar to that in liver, adipose tissue, and gut. J Clin Invest. Sep. 1988;82(3):928-935.

Spector AA, Fletcher JE & Ashbrook JD. Analysis of long-chain free fatty acid binding to bovine serum albumin by determination of stepwise equilibrium constants. Biochemistry 1971; 10: 3229-3232.

Stratford-Perricaudet et al. "Evaluation of the Transfer and Expression in Mice of an Enzyme-Encoding Gene Using a Human Adenovirus Vector." Hum Gene Ther. 1990 Fall;1(3):241-56.

Stremmel W, Berk PD. Hepatocellular influx of [14C]oleate reflects membrane transport rather than intracellular metabolism or binding. Proc Natl Acad Sci U S A. 1986; 83(10):3086-3090.

Stremmel W. Uptake of fatty acids by jejunal mucosal cells is mediated by a fatty acid binding membrane protein. J Clin Invest. Dec. 1988;82(6):2001-2010.

Stump DD, Fan X, Berk PD. Oleic acid uptake and binding by rat adipocytes define dual pathways for cellular fatty acid uptake. J Lipid Res. Apr. 2001;42(4):509-520.

Stump DD, Nunes RM, Sorrentino D, Isola LM, Berk PD. Characteristics of oleate binding to liver plasma membranes and its uptake by isolated hepatocytes. J Hepatol. 1992;16(3):304-315.

Su X, Abumrad NA. Cellular fatty acid uptake: a pathway under construction. Trends Endocrinol Metab. Mar. 2009;20(2):72-7, 13 pages.

Sugiyama H, et al., p70 S6 kinase sensitivity to rapamycin is eliminated by amino acid substitution of Thr229. J Immunol, 1996, 157(2):656-60.

Sun XJ, et al., Role of IRS-2 in insulin and cytokine signalling. Nature, 1995, 377:173-7.

Sun XJ, et al., Structure of the insulin receptor substrate IRS-1 defines a unique signal transduction protein. Nature, 1991, 352:73-7.

Sun, H.D., et al., Monoclonal antibody antagonists of hypothalamic FGFR1 cause potent but reversible hypophagia and weight loss in rodents and monkeys. Am J Physiol Endocrinol Metab, 2007. 292(3): p. E964-E976.

Tartaglia, L. A. et al., Identification and expression cloning of a leptin receptor, OB-R. 1995, Cell 83:1263-1271.

Tijssen P, Laboratory Techniques in Biochemistry and Molecular Biology Hybridization with Nucleic Acid Probes, Part I. Theory and Nucleic Acid Preparation, Elsevier Science Publishers, New York (1993) 7 pgs.

Tolppanen AM, Pulkkinen L, Kolehmainen M, Schwab U, Lindström J, Tuomilehto J, Uusitupa M; Finnish Diabetes Prevention Study Group. Tenomodulin is associated with obesity and diabetes risk: the Finnish diabetes prevention study. Obesity (Silver Spring). May 2007;15(5):1082-8.

Trentin L, Giordan M, Dingermann T, Basso G, Te Kronnie G, Marschalek R. Two independent gene signatures in pediatric t(4;11) acute lymphoblastic leukemia patients. Eur J Haematol. Jun. 25, 2009, 406-419.

Ukena SN, Koenecke C, Geffers R, Fuehner T, Welte T, Ganser A, Buer J, Franzke A. T helper type 2 differentiation is associated with induction of antibacterial defense mechanisms in blood lymphocytes of patients with sarcoidosis. Immunol Invest. 2009;38(1):49-66.

Verma IM, Gene Therapy, Treatment of disease by introducing healthy genes into the body is becoming feasible. But the therapy will not reach its full potential until the genes can be coaxed to work throughout life. Scientific American: 68-72, 81-82, 84 (1990).

Verna EC, Berk PD. Role of fatty acids in the pathogenesis of obesity and fatty liver: Impact of bariatric surgery. Semin Liver Dis 2008; 28(4): 407-426.

Vijayakumar, A., et al., Targeted loss of GHR signaling in mouse skeletal muscle protects against high-fat diet-induced metabolic deterioration. Diabetes, 2012. 61(1): p. 94-103.

Volarevic S and G Thomas, Role of S6 phosphorylation and S6 kinase in cell growth. Prog Nucleic Acid Res Mol Biol, 2001, 65:101-27.

Waehler et al., Engineering targeted viral vectors for gene therapy. Nat Rev Genet. 8(8):573-87 (2007).

Walewski, J.L., et al., A Novel Human Peptide that Reduces Adipocyte Uptake of Long Chain Fatty Acids and Causes Weight Loss in Mice, in the Obesity Society 2012: San Antonio, TX, 3 pages.

Walewski, J.L., et al., Adipocyte accumulation of long-chain fatty acids in obesity is multifactorial, resulting from increased fatty acid uptake and decreased activity of genes involved in fat utilization. Obes Surg, 2010. 20(1): p. 93-107, 26 pages.

Wallace AM, et al., Plasma leptin and the risk of cardiovascular disease in the west of Scotland coronary prevention study (WOSCOPS). Circulation, 2001, 104(25):3052-6.

Wang L, Beecham A, Di Tullio MR, Slifer S, Blanton SH, Rundek T, Sacco RL. Novel quantitative trait locus is mapped to chromosome 12p11 for left ventricular mass in Dominican families: the Family Study of Stroke Risk and Carotid Atherosclerosis. BMC Med Genet. Jul. 23, 2009;10:74. doi: 10.1186/1471-2350-10-74, 8 pages.

(56) References Cited

OTHER PUBLICATIONS

Wang, H., et al., "ATP-Sensitive potassium channel openers and 2,3-dimethyl-2-butylamine derivatives," Curr Med Chem, 2007, vol. 14, No. 2, pp. 133-155.

Wang, Y., Beydoun, M A, The obesity epidemic in the United States gender, age socio-economic, racial/ethnic and geograpical characteristics: a systematic review and meta-regression analyses. Epidemol Reviews, 2007. 29: p. 6-28.

Werner et al., "Joining high-throughput technology with in silicomodelling advances genome-wide screening towards targeted discovery." (2006) Brief Funct. Genomic Proteomic 5(1):32-6.

Wilkinson et al. "Constitutive and enhanced expression from the CMV major IE promoter in a defective adenovirus vector." Nucleic Acids Res. May 11, 1992;20(9):2233-9.

Woodward J, Immobilized Cells and Enzymes, IRL Press Limited (1986) 8 pgs.

Wosilait WD & Nagy P. A method of computing drug distribution in plasma using stepwise association constants: clofibrate acid as an illustrative example. Comput Programs Biomed 1976; 6: 142-148.

Wozniak, S.E., et al., Adipose tissue: the new endocrine organ? A review article. Dig Dis Sci, 2009. 54(9): p. 1847-56.

Wu et al., The ligation amplification reaction (LAR)—amplification of specific DNA sequences using sequential rounds of template-dependent ligation. Genomics 4(4):560-569 (1989).

Yamaguchi K, Yang L, McCall S, et al. Inhibiting triglyceride synthesis improves hepatic steatosis but exacerbates liver damage and fibrosis in obese mice with nonalcoholic steatohepatitis. Hepatology. Jun. 2007; 45(6):1366-1374.

Yanovski, S.Z. and J.A. Yanovski, Obesity. N Engl J Med, 2002. 346(8): p. 591-602.

Yu et al., 2002, RNA interference by expression of short-interfering RNAs and hairpin RNAs in mammalian cells. Proc Natl Acad Sci USA, 99:6047-52.

Zhang, Y. et al., Positional cloning of the mouse obese gene and its human homologue. 1994, Nature 372:425-432.

Zhou, S., Sorrentino, D, Stump, D, Potter, B, and Berk, PD, Adipocyte Differentiation in 3T3-L1 Fibroblasts Is Associated with Expression of a Plasma-Membrane Fatty-Acid Binding-Protein. Hepatology, 1990(12): p. 897.

Zhou, S., Stump D, Kiang, CL, isola LM, and Berk PD, Mitochondrial aspartate aminotransferase expressed on the surface of 3T3-L1 adipocytes mediates saturable fatty acid uptake. Proc Soc Exp Biol Med, 1995. 208: p. 263-270.

Chen, H. et al., "Evidence That the Diabetes Gene Encodes the Leptin Receptor: Identification of a Mutation in the Leptin Receptor Gene in db/ db Mice," Cell, vol. 84, pp. 491-495 (Feb. 9, 1996).

International Search Report and Written Opinion issued from the International Searching Authority for Application No. PCT/US11/56417 dated Oct. 10, 2012 (17 Pages).

Supplemental European Search Report and Written Opinion issued by the European Patent Office for Application No. EP11833512.4 dated Mar. 10, 2014 (10 pages).

Author Unknown, "RGD_C12 orf39, Gene: C12orf39 (chromosome 12 open reading frame 39) Homo sapiens," Rat Genome Database, 2 pages (May 16, 2012).

Bognetti, E. et al., "Prevalence and correlates of obesity in insulin dependent diabetic patients," Archives of Disease in Childhood, vol. 73, No. 3, pp. 239-242 (Apr. 1995).

European Search Report issued by the European Patent Office for European Application No. 11833512.4 dated Mar. 27, 2014 11 pages.

First Office Action issued by the Chinese Patent Office for Chinese Application No. 201180057465.5 dated Jun. 4, 2014, 22 pages.

Jimenez-Cruz, A. et al., "Low glycemic index lunch on satiety in overweight and obese people with type 2 diabetes," Nutricion Hospitalaria., vol. 20, No. 5, pp. 348-350 (2005).

Orpana, H.M. et al., "BMI and Mortality: Results From a National Longitudinal Study of Canadian Adults," Obesity Journal, vol. 18, No. 1, pp. 214-218 (Jan. 2010).

Porzionato, Andrea et al., "Spexin expression in normal rat tissues," The Journal of Histochemistry and Cytochemistry: Official Journal of the Histochemistry Society, vol. 58, No. 9, pp. 825-837, ISSN: 1551-5044 (Sep. 2010).

Sandyarani, N., "Serum Vs. Plasma," URL: <http://www.buzzle.com/articles/serum-vs-plasma.html> 3 pages (retrieved from the internet on Jun. 25, 2014).

Arnold, Matthew, "Obesity market set for explosive growth, says report," Medical Marketing & Media, retrieved online from URL:<http://www.mmm-online.com/channel/obesity-market-set-for-explosive-growth-says-report/article/108301>, 3 pages (Mar. 25, 2008).

Chinese Office Action issued by the State Intellectual Property Office of the People's Republic of China for Chinese Application No. 201180057465.5 dated Feb. 17, 2015 (18 pages).

Chinese Office Action issued by the State Intellectual Property Office of the People's Republic of China for Chinese Application No. 201180057465.5 dated Nov. 9, 2015 (9 pages).

Frost & Sullivan Research Service, "U.S. Anti-obesity Prescription Markets," retrieved online from URL:<http://www.frost.com/prod/servlet/report-brochure.pag?id=N01C-01-00-00-00>, 4 pages (Sep. 26, 2006).

Gu, L., et al., "Spexin peptide is expressed in human endocrine and epithelial tissues and reduced after glucose load in type 2 diabetes," Peptides, vol. 71, pp. 232-239 (2015).

Hareyan, Armen G., "U.S. Weight Loss Market to Reach 58 Billion in 2007," Emax Health, retrieved online from URL:<http://www.emaxhealth.com/69/11203.html>, 4 pages (Apr. 19, 2007).

Qian, W., et al., "Decreased Circulating Levels of Oxytocin in Obesity and Newly Diagnosed Type 2 Diabetic Patients," J. Clin. Endocrinol. Metab., vol. 99, No. 12, pp. 4683-4689 (Dec. 2014).

Walewski, J. L., et al., "Spexin is a Novel Human Peptide that Reduces Adipocyte Uptake of Long Chain Fatty Acids and Causes Weight Loss in Rodents with Diet-induced Obesity," Obesity, vol. 22, No. 7, pp. 1643-1652 (Jul. 2014).

Toll et al. (2012) Peptides derived from the prohormone proNPQ/spexin are potent central modulators of cardiovascular and renal function and nociception, FASEB J., 26(2):947-54 (8 pages).

Kim et al., "Coevolution of the Spexin/Galanin/Kisspeptin Family: Spexin Activates Galanin Receptor Type II and III," Endocrinology, 155(5):1864-1873 (May 2014).

Rankovic et al., "Biased agonism: An emerging paradigm in GPCR drug discovery," Bioorganic & Medicinal Chemistry Letters, 26, pp. 241-250 (2016).

Wan et al., "C12ORF39, a novel secreted protein with a typical amidation processing signal," Biosci. Rep., 30, pp. 1-10 (2010).

Toll et al., "Peptides derived from the prohormone proNPQ/spexin are potent central modulators of cardiovascular and renal function and nociception," The FASEB Journal, 26, pp. 947-954 (Feb. 2012).

International Preliminary Report on Patentability for International Patent Application No. PCT/US2011/056417 dated Apr. 16, 2013 (9 pages).

Chan et al., "Conservation of core gene expression in vertebrate tissues," J. Biol., 8:33, 17 pages (2009).

Bailey, K.R. et al., "Galanin Receptor Subtype 2 (GalR2) Null Mutant Mice Display an Anxiogenic-like Phenotype Specific to the Elevated Plus-maze", Author Manuscript, Published in final edited form as: Pharmacol Biochem Behav 86(1), pp. 8-20 (Jan. 2007) (23 pages).

Barbe, L. et al., "Toward a Confocal Subcellular Atlas of the Human Proteome," Molecular & Cellular Proteomics, 7.3, pp. 499-508 (2008) (10 pages).

Chagnon, Y.C. et al., "Genomic scan for genes affecting body composition before and after training in Caucasians from Heritage", J Appl Physiol, 90:1777-1787, 2001 (11 pages).

Gerhard, D.S. et al., "The Status, Quality, and Expansion of the NIH Full-Length cDNA Project: The Mammalian Gene Collection (MGC)", Genome Research, 14(10B) pp. 2121-2127 (2004) (7 pages).

Maruyama, R. et al., "Searching for novel ATF4 target genes in human hepatoma cells by microarray analysis", Bioscience, Biotechnology, and Biochemistry, 80(6), pp. 1149-1154 (Mar. 11, 2016) (7 pages).

(56) References Cited

OTHER PUBLICATIONS

Oláh, J. et al., "Interactions of Pathological Hallmark Proteins: Tubulin Polymerization Promoting Protein/p25,β-Amyloid, and α-Synuclein", The Journal of Biological Chemistry, 286(39), pp. 34088-34100 (Sep. 30, 2011) (13 pages).

Ota, T. et al., "Complete sequencing and characterization of 21,243 full-length human cDNAs," Nature Genetics, 36(1), pp. 40-45 (Jan. 2004) (6 pages).

Otsuki, T. et al., "Signal Sequence and Keyword Trap in silico for Selection of Full-Length Human cDNAs Encoding Secretion or Membrane Proteins from Oligo-Capped cDNA Libraries", DNA Research, 12(2), pp. 117-126 (2005) (10 pages).

Rankinen, T. et al., "The Human Obesity Gene Map: The 2005 Update", Obesity, 14(4):529-644, Apr. 2006 (116 pages).

Reyes-Alcaraz, A. et al., "Development of Spexin-based Human Galanin Receptor Type II-Specific Agonists with Increased Stability in Serum and Anxiolytic Effect in Mice", Scientific Reports, 6:21453 (Feb. 24, 2016) (10 pages).

Robertson, C.R. et al., "Engineering Galanin Analogues that Discriminate Between GalR1 and GalR2 Receptor Subtypes and Exhibit Anticonvulsant Activity Following Systemic Delivery", Author Manuscript, Published in final edited form as: J Med Chem, 53(4), pp. 1871-1875 (Feb. 25, 2010) (15 pages).

Sonmez, K. et al., "Evolutionary Sequence Modeling for Discovery of Peptide Hormones", PLoS Computational Biology, 5(1):e1000258, (Jan. 9, 2009) (12 pages).

Strausberg, R.L. et al., "Generation and initial analysis of more than 15,000 full-length human and mouse cDNA sequences", PNAS USA, 99(26), pp. 16899-16903 (Dec. 24, 2002) (5 pages).

Toll, L.R., "NPQ/Spexin in Endogenous Ligand for the Galanin Receptor 3", NIH Grant #: 1R01DA040882-01A1 , Torrey Pines Institute for Molecular Studies, <http://grantome.com/grant/NIH/R01-DA040882-01A1> (2015) (4 pages).

Webling, K. et al., "Ala$^5$-galanin (2-11) is a $GAL_2R$ specific galanin analogue", Neuropeptides, 60, pp. 75-82 (Published online Aug. 25, 2016) (8 pages).

Whalen, E.J. et al., "Therapeutic potential of β-arrestin- and G protein-biased agonists", Author Manuscript, Published in final edited form as: Trends Mol Med 17(3), pp. 126-139 (Mar. 2011) (27 pages).

\* cited by examiner

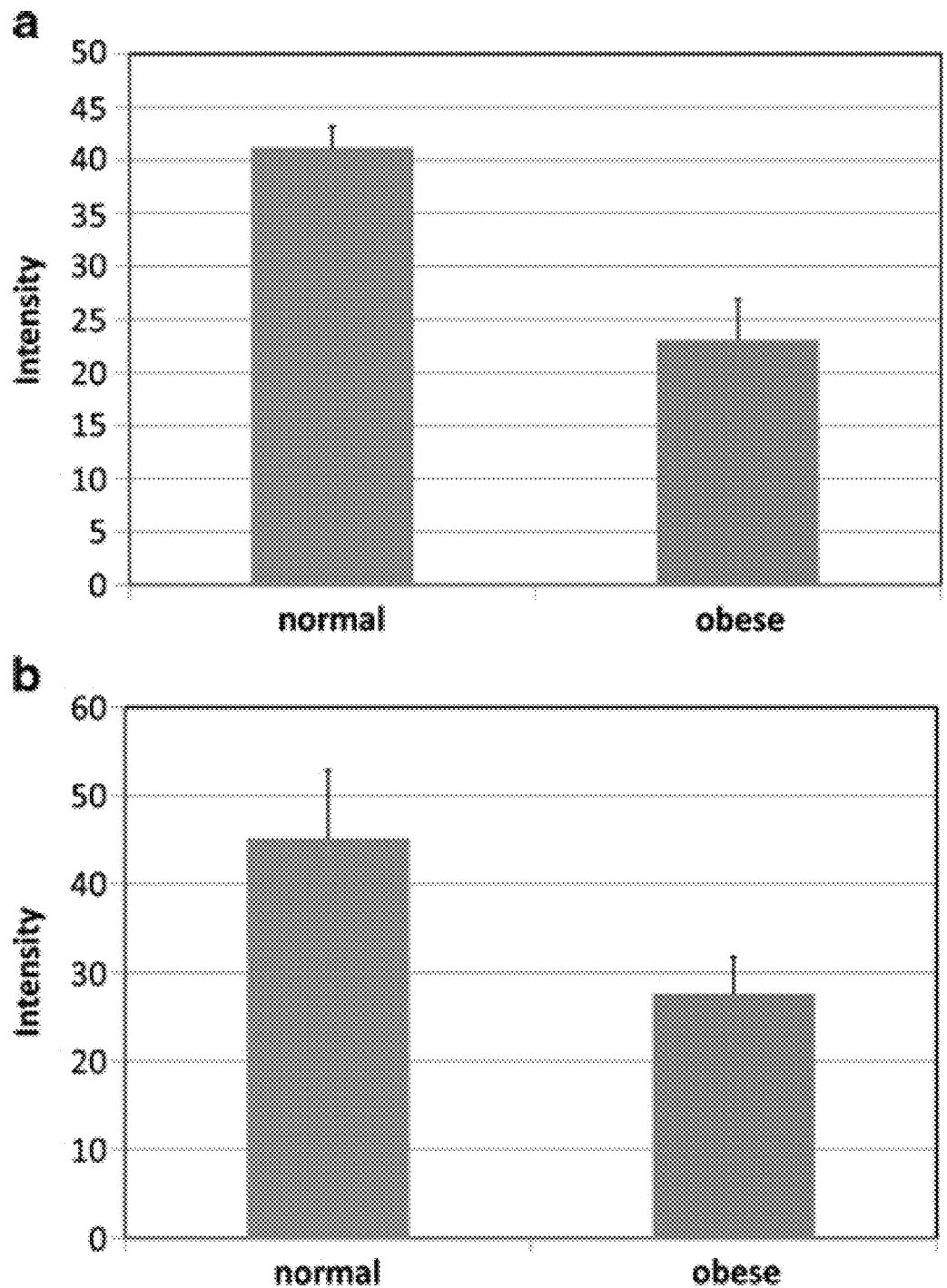
FIGS. 16A-B

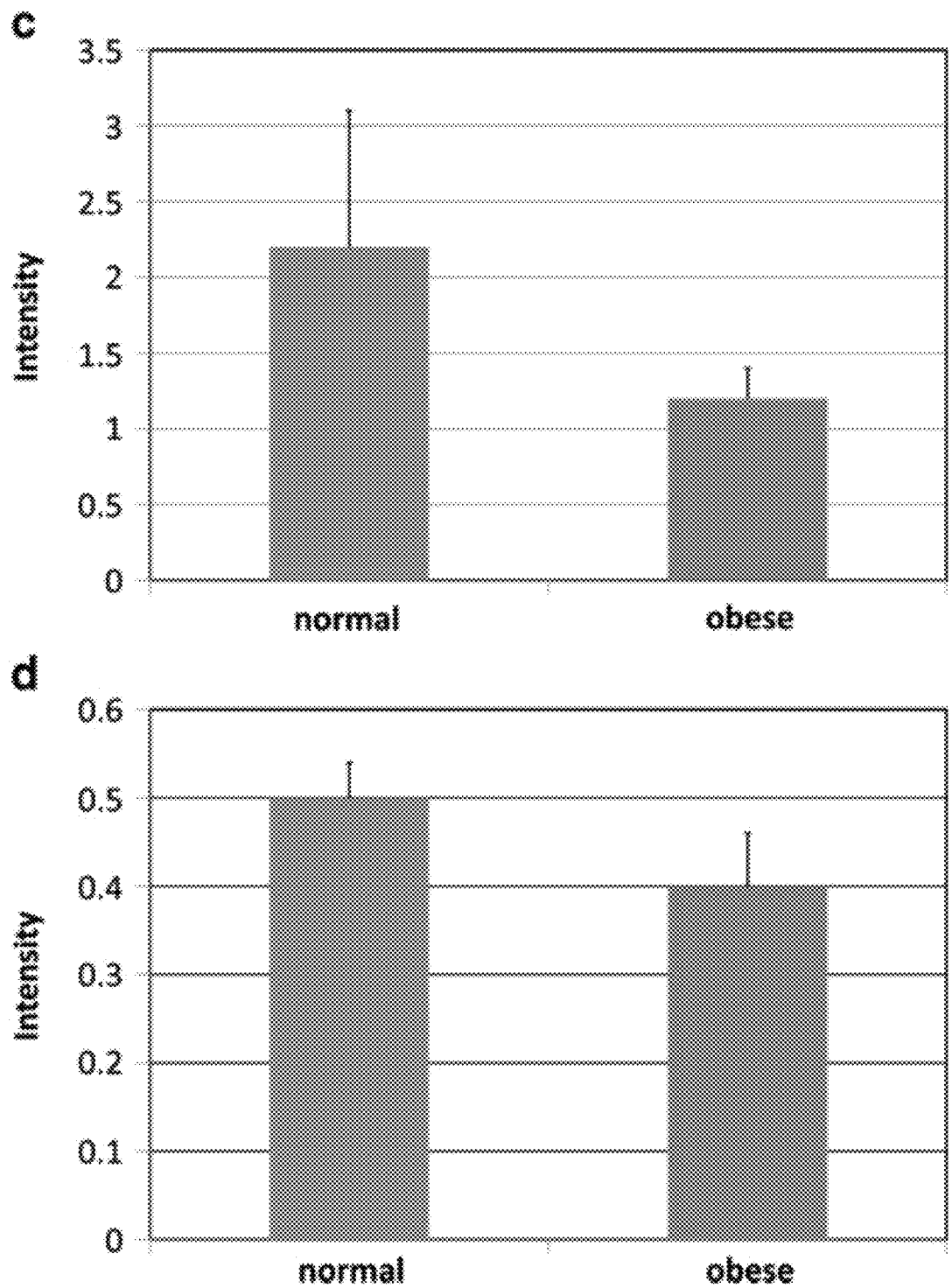
FIGS. 16C-D

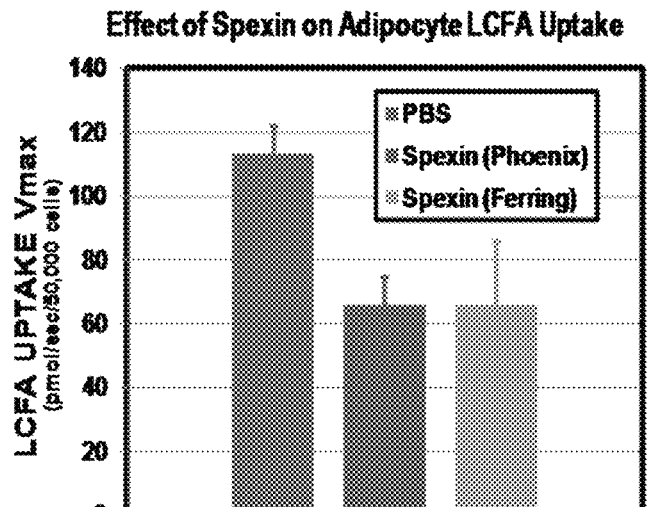
FIG. 21
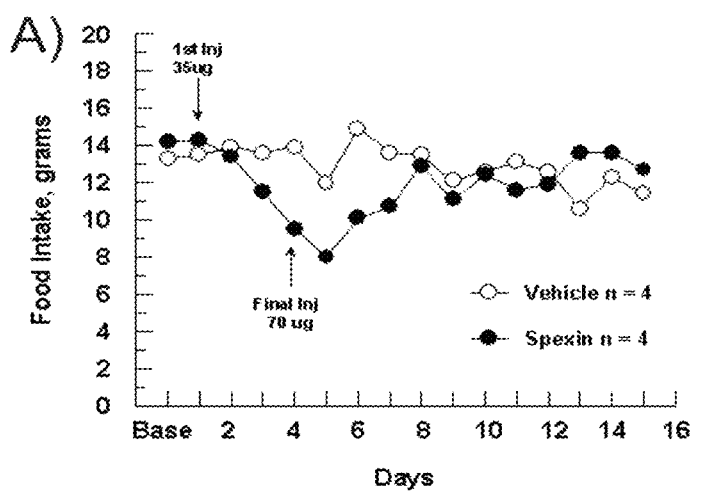
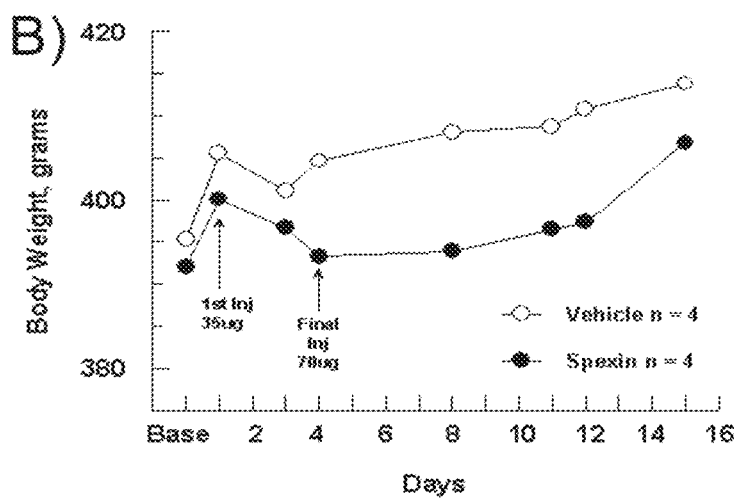
FIG. 22

OBESITY-RELATED GENES AND THEIR PROTEINS AND USES THEREOF

This application is a continuation-in-part of International Patent Application No. PCT/US2011/56417, filed Oct. 14, 2011, which claims priority to U.S. Provisional Patent Application No. 61/393,634 filed Oct. 15, 2010, the contents of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT SUPPORT

This invention was made with government support under DK066667, DK052401, and DK072526 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 19240.892US3_SL.txt and is 15,349 bytes in size.

BACKGROUND OF THE INVENTION

Obesity is a chronic disease manifested by an excess of fat mass in proportion to body size. Obesity is, de facto, the increased deposition of long chain fatty acids (LCFA), principally in the form of triglycerides (TG), in adipose and other tissues. Obese individuals have an excess of body fat relative to lean body mass that can contribute to other diseases.

Obesity is one of the most serious public health problems in the 21st century. According to the World Health Organization (WHO), obesity has reached epidemic proportions globally. More than 1 billion adults are overweight and at least 300 million of them are classified as clinically obese. Today, every third American is considered over-weight (Body Mass Index (BMI)>25 kg/m$^2$). 60% of adults in the US are obese or overweight, and obesity is widely recognized as the largest pharmaceutical market in the world, with few approved drugs that do not work well, leading to, at most, a 5-10% weight loss, that is not permanent. It is believed that genetic predisposition significantly increases the risk of becoming obese but specific details of the pathways involved have not been identified.

SUMMARY OF THE INVENTION

An aspect of the invention provides methods for treating obesity or an obesity-associated disorder in a subject. The methods comprise administering to a subject an effective amount of Spexin, thereby treating obesity or an obesity-associated disorder in the subject. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 kg/m$^2$. In other embodiments, the subject has a Body Mass Index (BMI) greater than about 30 kg/m$^2$. In further embodiments, the subject has a Body Mass Index (BMI) greater than about 35 kg/m$^2$. In other embodiments, the subject has a Body Mass Index (BMI) greater than about 40 kg/m$^2$. In other embodiments, the subject has a Body Mass Index (BMI) greater than about 45 kg/m$^2$. In other embodiments, the subject has a Body Mass Index (BMI) greater than about 50 kg/m$^2$. In other embodiments, the subject has a Body Mass Index (BMI) greater than about 55 kg/m$^2$. In other embodiments, the subject has a Body Mass Index (BMI) greater than about 60 kg/m$^2$. In other embodiments, the subject has a Body Mass Index (BMI) greater than about 65 kg/m$^2$. In other embodiments, the subject has a Body Mass Index (BMI) greater than about 70 kg/m$^2$. In other embodiments, the subject has a Body Mass Index (BMI) greater than about 75 kg/m$^2$. In one embodiment, the subject displays a decrease in adipose tissue mass after treatment with Spexin. In another embodiment, the Spexin amount administered results in at least about 1 ng/ml in the serum. In another embodiment, the Spexin amount administered results in at least about 3 ng/ml in the serum. In a further embodiment, the Spexin amount administered results in at least about 10 ng/ml in the serum. In some embodiments, the Spexin amount administered results in at least about 30 ng/ml in the serum. In other embodiments, the Spexin amount administered results in at least about 100 ng/ml in the serum. In further embodiments, the Spexin amount administered results in at least about 250 ng/ml in the serum. In some embodiments, the Spexin amount administered results in at least about 500 ng/ml in the serum. In one embodiment, Spexin is administered at least once daily or at least twice daily. In another embodiment, Spexin is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In a further embodiment, Spexin is administered for at least 1 year, for at least 1.5 years, for at least 2 years, for at least 2.5 years, for at least 5 years, for at least 7.5 years, for at least 10 years, or for at least 15 years.

The invention provides methods for treating obesity or an obesity-associated disorder in a subject. The methods comprise administering to a subject in need thereof a polypeptide comprising SEQ ID NO: 1, or a pharmaceutically acceptable salt thereof, thereby treating obesity or an obesity-associated disorder in the subject. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 kg/m$^2$. In other embodiments, the subject has a Body Mass Index (BMI) greater than about 30 kg/m$^2$. In further embodiments, the subject has a Body Mass Index (BMI) greater than about 35 kg/m$^2$. In other embodiments, the subject has a Body Mass Index (BMI) greater than about 40 kg/m$^2$. In other embodiments, the subject has a Body Mass Index (BMI) greater than about 45 kg/m$^2$. In other embodiments, the subject has a Body Mass Index (BMI) greater than about 50 kg/m$^2$. In other embodiments, the subject has a Body Mass Index (BMI) greater than about 55 kg/m$^2$. In other embodiments, the subject has a Body Mass Index (BMI) greater than about 60 kg/m$^2$. In other embodiments, the subject has a Body Mass Index (BMI) greater than about 65 kg/m$^2$. In other embodiments, the subject has a Body Mass Index (BMI) greater than about 70 kg/m$^2$. In other embodiments, the subject has a Body Mass Index (BMI) greater than about 75 kg/m$^2$.

An aspect of the invention provides for methods for promoting satiety in an obese subject or a subject afflicted with an obesity-associated disorder, the method comprising administering to a subject an effective amount of Spexin, thereby promoting satiety in an obese subject. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 kg/m$^2$. In other embodiments, the subject has a Body Mass Index (BMI) greater than about 30 kg/m$^2$. In further embodiments, the subject has a Body Mass Index (BMI) greater than about 35 kg/m$^2$. In other embodiments, the subject has a Body Mass Index (BMI) greater than about 40 kg/m$^2$. In other embodiments, the subject has a Body Mass Index (BMI) greater than about 45 kg/m$^2$. In other embodiments, the subject has a Body Mass Index (BMI) greater than about 50 kg/m$^2$. In other embodiments, the subject has a Body Mass Index (BMI) greater than about 55 kg/m$^2$. In other embodiments, the subject has a Body Mass Index (BMI) greater than about 60 kg/m$^2$. In other embodiments, the subject has a Body Mass Index (BMI) greater than about 65 kg/m$^2$. In other embodiments, the subject has a Body Mass Index (BMI) greater than about 70 kg/m$^2$. In other embodiments, the subject has a Body Mass Index (BMI) greater than about 75 kg/m$^2$. In one embodiment, the subject displays a decrease in adipose tissue mass after treatment with Spexin. In another embodiment, the Spexin amount administered results in at least about 1 ng/ml in the serum. In another embodiment, the Spexin amount administered results in at least about 3 ng/ml in the serum. In a further embodiment, the Spexin amount administered results in at least about 10 ng/ml in the serum. In some embodiments, the Spexin amount administered results in at least about 30 ng/ml in the serum. In other embodiments, the Spexin amount administered results in at least about 100 ng/ml in the serum. In further embodiments, the Spexin amount administered results in at least about 250 ng/ml in the serum. In some embodiments, the Spexin amount administered results in at least about 500 ng/ml in the serum. In one embodiment, Spexin is administered at least once daily or at least twice daily. In another embodiment, Spexin is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In a further embodiment, Spexin is administered for at least 1 year, for at least 1.5 years, for at least 2 years, for at least 2.5 years, for at least 5 years, for at least 7.5 years, for at least 10 years, or for at least 15 years.

The invention further provides for methods for promoting satiety in an obese subject or a subject afflicted with an obesity-associated disorder, the method comprising administering to a subject in need thereof a polypeptide comprising SEQ ID NO: 1, or a pharmaceutically acceptable salt thereof, thereby promoting satiety in an obese subject. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 kg/m$^2$. In other embodiments, the subject has a Body Mass Index (BMI) greater than about 30 kg/m$^2$. In further embodiments, the subject has a Body Mass Index (BMI) greater than about 35 kg/m$^2$.

An aspect of the invention also provides for a method of promoting weight loss in an obese subject or a subject afflicted with an obesity-associated disorder. The method comprises: a) administering to a subject an effective amount of Spexin; and b) determining whether Spexin decreased the subject's body mass as compared to the subject's body mass prior to treatment with Spexin, thereby promoting weight loss in the obese subject or the subject afflicted with an obesity-associated disorder. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 $kg/m^2$. In other embodiments, the subject has a Body Mass Index (BMI) greater than about 30 $kg/m^2$. In further embodiments, the subject has a Body Mass Index (BMI) greater than about 35 $kg/m^2$. In other embodiments, the subject has a Body Mass Index (BMI) greater than about 40 $kg/m^2$. In other embodiments, the subject has a Body Mass Index (BMI) greater than about 45 $kg/m^2$. In other embodiments, the subject has a Body Mass Index (BMI) greater than about 50 $kg/m^2$. In other embodiments, the subject has a Body Mass Index (BMI) greater than about 55 $kg/m^2$. In other embodiments, the subject has a Body Mass Index (BMI) greater than about 60 $kg/m^2$. In other embodiments, the subject has a Body Mass Index (BMI) greater than about 65 $kg/m^2$. In other embodiments, the subject has a Body Mass Index (BMI) greater than about 70 $kg/m^2$. In other embodiments, the subject has a Body Mass Index (BMI) greater than about 75 $kg/m^2$. In one embodiment, the subject displays a decrease in adipose tissue mass after treatment with Spexin. In another embodiment, the Spexin amount administered results in at least about 1 ng/ml in the serum. In another embodiment, the Spexin amount administered results in at least about 3 ng/ml in the serum. In a further embodiment, the Spexin amount administered results in at least about 10 ng/ml in the serum. In some embodiments, the Spexin amount administered results in at least about 30 ng/ml in the serum. In other embodiments, the Spexin amount administered results in at least about 100 ng/ml in the serum. In further embodiments, the Spexin amount administered results in at least about 250 ng/ml in the serum. In some embodiments, the Spexin amount administered results in at least about 500 ng/ml in the serum. In one embodiment, Spexin is administered at least once daily or at least twice daily. In another embodiment, Spexin is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In a further embodiment, Spexin is administered for at least 1 year, for at least 1.5 years, for at least 2 years, for at least 2.5 years, for at least 5 years, for at least 7.5 years, for at least 10 years, or for at least 15 years.

An aspect of the invention provides for methods of promoting weight loss in an obese subject or a subject afflicted with an obesity-associated disorder. The methods comprise: a) administering to a subject in need thereof a therapeutic amount of a polypeptide comprising SEQ ID NO: 1 or a pharmaceutically acceptable salt thereof; and b) determining whether the polypeptide comprising SEQ ID NO: 1 decreased the subject's body mass as compared to the subject's body mass prior to treatment with polypeptide comprising SEQ ID NO: 1, thereby promoting weight loss in the obese subject or the subject afflicted with an obesity-associated disorder. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 $kg/m^2$. In other embodiments, the subject has a Body Mass Index (BMI) greater than about 30 $kg/m^2$. In further embodiments, the subject has a Body Mass Index (BMI) greater than about 35 $kg/m^2$. In other embodiments, the subject has a Body Mass Index (BMI) greater than about 40 $kg/m^2$. In other embodiments, the subject has a Body Mass Index (BMI) greater than about 45 $kg/m^2$. In other embodiments, the subject has a Body Mass Index (BMI) greater than about 50 $kg/m^2$. In other embodiments, the subject has a Body Mass Index (BMI) greater than about 55 $kg/m^2$. In other embodiments, the subject has a Body Mass Index (BMI) greater than about 60 $kg/m^2$. In other embodiments, the subject has a Body Mass Index (BMI) greater than about 65 $kg/m^2$. In other embodiments, the subject has a Body Mass Index (BMI) greater than about 70 $kg/m^2$. In other embodiments, the subject has a Body Mass Index (BMI) greater than about 75 $kg/m^2$.

An aspect of the invention provides for methods of decreasing serum Leptin levels in an obese subject or a subject afflicted with an obesity-associated disorder. The methods comprise: a) administering to a subject an effective amount of Spexin; and b) determining whether Spexin decreased the subject's serum Leptin levels as compared to the subject's serum Leptin levels prior to treatment with Spexin, thereby decreasing serum Leptin levels in the obese subject or the subject afflicted with an obesity-associated disorder. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 $kg/m^2$. In other embodiments, the subject has a Body Mass Index (BMI) greater than about 30 $kg/m^2$. In further embodiments, the subject has a Body Mass Index (BMI) greater than about 35 $kg/m^2$. In other embodiments, the subject has a Body Mass Index (BMI) greater than about 40 $kg/m^2$. In other embodiments, the subject has a Body Mass Index (BMI) greater than about 45 $kg/m^2$. In other embodiments, the subject has a Body Mass Index (BMI) greater than about 50 $kg/m^2$. In other embodiments, the subject has a Body Mass Index (BMI) greater than about 55 kg/m². In other embodiments, the subject has a Body Mass Index (BMI) greater than about 60 kg/m². In other embodiments, the subject has a Body Mass Index (BMI) greater than about 65 kg/m². In other embodiments, the subject has a Body Mass Index (BMI) greater than about 70 kg/m². In other embodiments, the subject has a Body Mass Index (BMI) greater than about 75 kg/m². In one embodiment, the subject displays a decrease in adipose tissue mass after treatment with Spexin. In another embodiment, the Spexin amount administered results in at least about 1 ng/ml in the serum. In another embodiment, the Spexin amount administered results in at least about 3 ng/ml in the serum. In a further embodiment, the Spexin amount administered results in at least about 10 ng/ml in the serum. In some embodiments, the Spexin amount administered results in at least about 30 ng/ml in the serum. In other embodiments, the Spexin amount administered results in at least about 100 ng/ml in the serum. In further embodiments, the Spexin amount administered results in at least about 250 ng/ml in the serum. In some embodiments, the Spexin amount administered results in at least about 500 ng/ml in the serum. In one embodiment, Spexin is administered at least once daily or at least twice daily. In another embodiment, Spexin is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In a further embodiment, Spexin is administered for at least 1 year, for at least 1.5 years, for at least 2 years, for at least 2.5 years, for at least 5 years, for at least 7.5 years, for at least 10 years, or for at least 15 years.

The invention provides for a method of decreasing serum Leptin levels in an obese subject or a subject afflicted with an obesity-associated disorder. The method comprises: a) administering to a subject in need thereof a therapeutic amount of a polypeptide comprising SEQ ID NO: 1 or a pharmaceutically acceptable salt thereof; and b) determining whether the polypeptide comprising SEQ ID NO: 1 decreased the subject's serum Leptin levels as compared to the subject's serum Leptin levels prior to treatment with polypeptide comprising SEQ ID NO: 1, thereby decreasing serum Leptin levels in the obese subject or the subject afflicted with an obesity-associated disorder. In one embodiment, the subject is a human or non-human animal. In another embodiment, the non-human animal is a mouse, rat, dog, or cat. In a further embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination thereof. In some embodiments, the metabolic disorder comprises hyperglycemia, insulin resistance, hyperinsulinemia, metabolic syndrome, or a combination of such disorders. In other embodiments, the lipid related disorder comprises atherosclerosis, HIV lipodystrophy, coronary heart disease, dyslipidemia, or a combination of a disorder listed herein. In further embodiments, the cancer comprises endometrial cancer, breast cancer, colon cancer, or a combination of such a cancer. In some embodiments, the subject has a Body Mass Index (BMI) greater than about 25 kg/m². In other embodiments, the subject has a Body Mass Index (BMI) greater than about 30 kg/m². In further embodiments, the subject has a Body Mass Index (BMI) greater than about 35 kg/m². In other embodiments, the subject has a Body Mass Index (BMI) greater than about 40 kg/m². In other embodiments, the subject has a Body Mass Index (BMI) greater than about 45 kg/m². In other embodiments, the subject has a Body Mass Index (BMI) greater than about 50 kg/m². In other embodiments, the subject has a Body Mass Index (BMI) greater than about 55 kg/m². In other embodiments, the subject has a Body Mass Index (BMI) greater than about 60 kg/m². In other embodiments, the subject has a Body Mass Index (BMI) greater than about 65 kg/m². In other embodiments, the subject has a Body Mass Index (BMI) greater than about 70 kg/m². In other embodiments, the subject has a Body Mass Index (BMI) greater than about 75 kg/m².

In one embodiment, the subject displays a decrease in adipose tissue mass after treatment with Spexin. In another embodiment, the Spexin amount administered results in at least about 1 ng/ml in the serum. In another embodiment, the Spexin amount administered results in at least about 3 ng/ml in the serum. In a further embodiment, the Spexin amount administered results in at least about 10 ng/ml in the serum. In some embodiments, the Spexin amount administered results in at least about 30 ng/ml in the serum. In other embodiments, the Spexin amount administered results in at least about 100 ng/ml in the serum. In further embodiments, the Spexin amount administered results in at least about 250 ng/ml in the serum. In some embodiments, the Spexin amount administered results in at least about 500 ng/ml in the serum. In one embodiment, Spexin is administered at least once daily or at least twice daily. In another embodiment, Spexin is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks. In a further embodiment, Spexin is administered for at least 1 year, for at least 1.5 years, for at least 2 years, for at least 2.5 years, for at least 5 years, for at least 7.5 years, for at least 10 years, or for at least 15 years.

An aspect of the invention provides methods for detecting the presence of or a predisposition to obesity or an obesity-associated disorder in a human subject. The methods comprise: (a) obtaining a biological sample from a subject; and (b) detecting whether or not there is an alteration in the expression of a Obesity-Signature (OS) gene in the subject as compared to a subject not afflicted with obesity or an obesity-associated disorder. In one embodiment, the Obesity-Signature (OS) gene comprises any gene indicated as being differentially expressed (e.g., up-regulated or down-regulated) in any one of Tables 7-8, and/or Spexin, or a combination of such. In some embodiments, the Obesity-Signature (OS) gene comprises any gene indicated as being differentially expressed (e.g., down-regulated or up-regulated) in any one of Tables 7-8, and/or Spexin, or a combination of such. In one embodiment, the obesity-associated disorder comprises a metabolic disorder, hypertension, congestive heart failure, a lipid related disorder, type II diabetes mellitus, gallbladder disease, osteoarthritis, sleep apnea, cancer, polycystic ovary syndrome (PCOS), or a combination of the listed disorders. In another embodiment, the metabolic disorder comprises hyperglycemia, insulin resistance, hyperinsulinemia, metabolic syndrome, or a combination of such listed. In some embodiments, the lipid related disorder comprises atherosclerosis, coronary heart disease, dyslipidemia, HIV lipidodystrophy, or a combination of those listed disorders. In further embodiments, the cancer comprises endometrial cancer, breast cancer, colon cancer, or a combination of the listed cancers. In one embodiment, the detecting comprises determining in the sample whether expression of at least 2 OS genes, at least 3 OS genes, at least 4 OS genes, at least 5 OS genes, at least 6 OS genes, at least 7 OS genes, at least 8 OS genes, at least 9 OS genes, or at least 10 OS genes indicated as being differentially expressed (e.g., up-regulated or down-regulated) in any one of Tables 7-8, and/or Spexin, or a combination of such, are decreased as compared to expression in a normal sample. In another embodiment, the detecting comprises determining in the sample whether expression of at least 2 OS genes, at least 3 OS genes, at least 4 OS genes, at least 5 OS genes, at least 6 OS genes, at least 7 OS genes, at least 8 OS genes, at least 9 OS genes, or at least 10 OS genes indicated as being differentially expressed (e.g., up-regulated or down-regulated) in any one of Tables 7-8, or a combination of such tables indicated, are increased as compared to expression in a normal sample. In one embodiment, the detecting comprises determining in the sample whether expression of at least 2 OS genes, at least 3 OS genes, at least 4 OS genes, at least 5 OS genes, at least 6 OS genes, at least 7 OS genes, at least 8 OS genes, at least 9 OS genes, or at least 10 OS genes indicated as being differentially expressed (e.g., down-regulated or up-regulated) in any one of Tables 7-8, or a combination of such, are increased as compared to expression in a normal sample. In a further embodiment, the detecting comprises determining in the sample whether expression of at least 2 OS genes, at least 3 OS genes, at least 4 OS genes, at least 5 OS genes, at least 6 OS genes, at least 7 OS genes, at least 8 OS genes, at least 9 OS genes, or at least 10 OS genes indicated as being differentially expressed (e.g., down-regulated or up-regulated) in any one of Tables 7-8, and/or Spexin, or a combination of such indicated, are decreased as compared to expression in a normal sample. In some embodiments, the detecting comprises gene sequencing, selective hybridization, selective amplification, gene expression analysis, or a combination of a method indicated. In other embodiments, the sample comprises subcutaneous adipose tissue, omental adipose tissue, whole blood, plasma, serum, white blood cells, or mesenteric adipose tissue.

An aspect of the invention provides for a diagnostic kit for determining whether a sample from a subject exhibits increased or decreased expression of at least 2 or more OS genes, the kit comprising nucleic acid primers that specifically hybridize to a OS gene, wherein the primer will prime a polymerase reaction only when a OS gene in any one of Tables 7-8, and/or Spexin, is present.

An aspect of the invention provides for methods for identifying a Spexin-modulating compound useful for treating obesity or an obesity-associated disorder in a subject. The methods comprise: (a) administering a test agent to a mouse model of obesity or an obesity-associated disorder; and (b) determining whether the test agent altered serum Spexin levels, serum Leptin levels, a body-weight phenotype, or a combination thereof, as compared to a mouse in the absence of the test agent, thereby identifying a compound useful for treating obesity or an obesity-associated disorder. In one embodiment, the serum Spexin levels are increased. In another embodiment, the serum Leptin levels are decreased. In a further embodiment, the body-weight phenotype is a decrease in adipose tissue mass. In some embodiments, the test agent comprises a polynucleotide, small organic molecule, a small inorganic molecule, a soluble peptide, or an antibody. In other embodiments, the antibody specifically binds to a Spexin protein or a fragment thereof. In further embodiments, the polynucleotide is an antisense RNA that specifically inhibits expression of a Spexin gene that encodes a Spexin protein. In some embodiments, the polynucleotide is an siRNA that specifically targets a Spexin gene that encodes a Spexin protein.

BRIEF DESCRIPTION OF THE FIGURES

The original color versions of some of the figures can be viewed in Walewski et al., Obes Surg. 2010 January; 20(1): 93-107, of which the contents are herein incorporated by reference. The content corresponding to some of these figures can be viewed in Walewski et al.

FIG. 14A shows a Log-Log plot of all genes assayed in this study. Means of each data point are presented as a scatterplot (n=3 in each group, obese vs. normal). Relative expression data for 566 statistically significant genes (p<0.05, 1.2 fold or greater change in expression) are presented in color (red=up, blue=down). "Red" is depicted as dark grey circles to the top of the light grey circles (above and to the left of the line-of-identity [45°]). "Blue" is depicted as dark grey circles to the bottom of the light grey circles (below and to the right of the line-of-identity [45°]). FIG. 14B shows a detailed view of a representative section of scatterplot (centered dark grey square in FIG. 14A). Red (up in obese) and blue (down in obese) data points are statistically significant, whereas non-significant data points are represented as grey circles. "Red" is depicted as dark grey circles to the top of the light grey circles. "Blue" is depicted as dark grey circles to the bottom of the light grey circles. FIG. 14C. shows quartile box plots of means of all genes in normal (N=3) vs. obese (N=3). Striking similarities exist between the two groups.

FIG. 16 shows bar graphs depicting two adenylate cyclase genes that are involved in hormonal stimulation of lipolysis are under-expressed in obese omental fat. Adenylate Cyclase 6 is a membrane-associated enzyme and catalyzes the formation of the secondary messenger cyclic adenosine monophosphate (cAMP). This gene was 1.78-fold under-expressed in obese omental fat in cohort 1 (FIG. 16A), and 1.64 under-expressed in the cohort 2 samples (FIG. 16B). Adenylate Cyclase activating peptide receptor 1 is a membrane-associated protein and shares significant homology with members of the glucagon/secretin receptor family. This receptor mediates diverse biological actions of adenylate cyclase activating polypeptide 1 and is positively coupled to adenylate cyclase. This gene was 1.74-fold under-expressed in obese omental fat in cohort 1 (FIG. 16C), and 1.18 fold under-expressed in the cohort 2 samples (FIG. 16D).

FIG. 18A is a graph depicting the mean body weights per day of PBS injected DIO mice. The PBS injected DIO mice continued to gain weight. FIG. 18B is a graph depicting mean body weights of Spexin injected mice. The mice are losing approximately 0.3 g of body weight per day. Setting aside the day 2 body weight, the remaining days show a clear negative correlation between dosing day and body weight (r=−0.999).

FIG. 21 is a bar graph showing the effect of Spexin on adipocyte LCFA uptake.

FIG. 22 shows daily injections of spexin into DIO rats that lead to reductions in both food intake (FIG. 22A) and Body Weight (FIG. 22B). Spexin-treated DIO rats (N=4; 35 or 70 µgm/kg, SC) and vehicle-injected DIO rats (N=4) were approximately 20% overweight at the beginning of treatment. Individual body weights and total food consumed were measured daily. Note that the reduction in body weight persisted well beyond the treatment period.

(FIG. 23A) Pre-treatment period; both groups refrain from eating during the "daylight period [lights on] as indicated by the horizontal white lines". When the lights are turned off "nighttime [lights off]", both groups of DIO rats begin to consume food at regular intervals "meals". It should be noted that meal duration and the amounts of food consumed per meal are very consistent thoughout the feeding period. (FIG. 23B) On-treatment; rats were injected with Peptide A (Spexin) (35 or 70 µgm/kg, SC), or vehicle. Peptide A (Spexin)-treated animals demonstrated reduced meal size and duration, without altering meal patterns (frequency and "light off" timing) during the 24 hr recording cycle. Peptide A (Spexin)-treated animals consumed approximately 30% less total diet over a 24 hr recording period. However, the spexin-treated animals did not exhibit overt toxicity or nausea as evidenced by continued eating during the "lights on" cycle. (FIG. 23C) "Washout"; during the initial days post-Spexin treatment, the satiety effect begins to diminish. (FIG. 23D) Off-treatment; several days after the last injection of Peptide A (Spexin), both groups of animals again demonstrate equivalent total 24 hr food consumption and meal patterns.

DETAILED DESCRIPTION OF THE INVENTION

Figure 1:
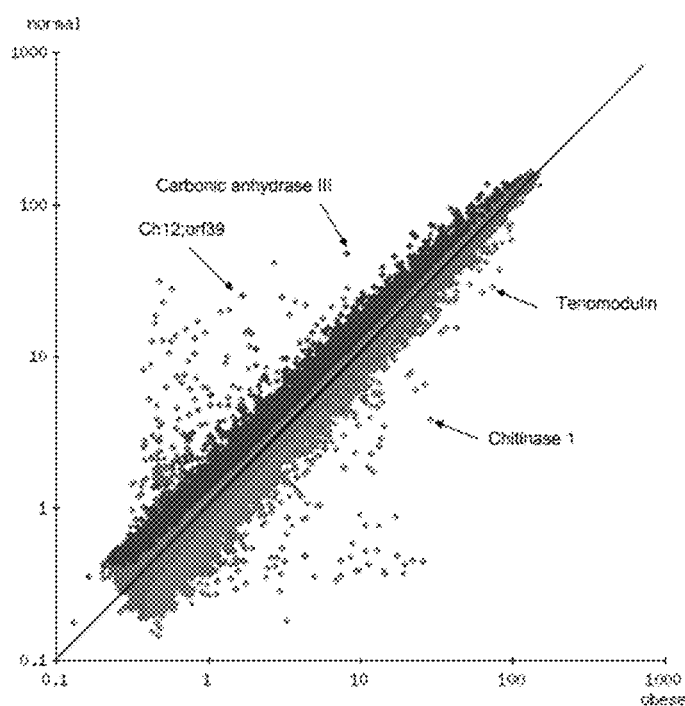
FIG. 1 is a log-log plot of gene expression differences between normal and obese fat. Data points represent the mean expression ratios (normal [n=8] vs obese fat [n=12]). Colored dots represent genes that have statistically significant differences (p<0.05) in expression values between sample sets (red=genes that are over-expressed in normal fat, green=genes that are over-expressed in obese fat; grey data points represent non-significant data). Ch12; orf39 is Spexin.

The invention provides, in part, the discovery of genes that are differentially expressed in obese and normal fat, providing the basis for Obesity Signatures (OSs) that can be used as therapeutic targets for obesity. These gene expression studies in human obese fat, thus, can be used to identify therapeutic targets using animal models of obesity. Once the targets are identified, the Obesity Signatures can be used for methods of diagnosis and treatment for obesity and obesity-associated disorders. In one embodiment, genes comprising an Obesity Signature comprise those genes listed in Table 7 and Table 8, Spexin, or a combination thereof.

The invention provides methods for administering Spexin or a polypeptide comprising SEQ ID NO: 1, or derived from Spexin, or a pharmaceutically acceptable salt thereof, to an obese subject to treat obesity or an obesity-associated disorder. The invention also provides methods for administering Spexin or a polypeptide comprising SEQ ID NO: 1, or a pharmaceutically acceptable salt thereof, to an obese subject or a subject afflicted with an obesity-associated disorder in order to promote weight loss in the subject. The invention further provides methods for administering Spexin or a polypeptide comprising SEQ ID NO: 1, or a pharmaceutically acceptable salt thereof, to an obese subject or a subject afflicted with an obesity-associated disorder to promote satiety in the subject. The invention also provides methods for detecting the presence of or a predisposition to obesity or an obesity-associated disorder in a human subject. The invention additionally provides a diagnostic kit for determining whether a subject is predisposed to obesity or an obesity-associated disorder or whether a sample from a subject exhibits increased or decreased expression of at least 2 or more Obesity-Signature (OS) genes. The invention further provides methods for identifying compounds useful for treating obesity or an obesity-associated disorder in a subject.

Obesity and Obesity-Associated Disorders

Obesity is characterized by excess body fat and is a chronic disease posing a significant impact on quality of life, productivity, and socioeconomic status. A normal-sized person has between 30 and 35 billion fat cells. When a person gains weight, these fat cells first increase in size and then in number. Obesity is, de facto, the increased deposition of long chain fatty acids (LCFA), principally in the form of triglycerides (TG), in adipose and other tissues. Although LCFA were once believed to enter cells exclusively by passive diffusion across plasma membranes, the fact that TG accumulate in specific sites indicated that cellular LCFA uptake involves specific, regulatable mechanisms.

Obesity has been shown to increase the risk for hypertension, dyslipidemia (high total cholesterol or high levels of triglycerides), type II diabetes, coronary heart disease, stroke, gallbladder disease, osteoarthritis, sleep apnea, and some cancers (for example, endometrial cancer, breast cancer, and colon cancer). In one embodiment, an obesity-associated disorder comprises a metabolic disorder, hypertension, congestive heart failure, a lipid related disorder, type II diabetes mellitus (Non-insulin Dependent Diabetes Mellitus, NIDDM), gallbladder disease, osteoarthritis, sleep apnea, cancer, polycystic ovary syndrome (PCOS), or a combination thereof. In one embodiment, the metabolic disorder comprises hyperglycemia, insulin resistance, hyperinsulinemia, metabolic syndrome, or a combination thereof. In another embodiment, the lipid related disorder comprises atherosclerosis, coronary heart disease, dyslipidemia, or a combination thereof. In a further embodiment, the cancer comprises endometrial cancer, breast cancer, colon cancer, or a combination thereof.

Obesity occurs when a subject has a weight and body mass, particularly of fat tissue, above currently accepted standards. The body mass index (BMI; $kg/m^2$) provides a useful population-level measure of obesity that can be used to estimate the prevalence of obesity within a population and the risks associated with it. For example, a subject is obese with a BMI above the currently accepted standard. When a subject is a human, the current standards for both men and women accepted as "normal" are a BMI of about 20 $kg/m^2$ to about 24.9 $kg/m^2$. In one embodiment, an obese subject has a BMI of 25 $kg/m^2$ or greater. In another embodiment, an obese subject has a BMI of about 30 $kg/m^2$ or greater. In further embodiments, an obese subject has a BMI of about 40 $kg/m^2$ or greater. In some embodiments, the subject is obese when it weighs more than 120% of the normal body weight for its age and height. Even mild obesity, at 20% over desirable weight according to standard height-weight charts, can increase the risk for disease, such as the obesity-associated disorders described herein, and premature death. Normal body weights vary among species and individuals based on height, body build, bone structure, and sex. A subject, according to the invention includes, but is not limited to a human or non-human animal, such as a primate, a dog, a cat, a cow, a horse, a rabbit, a monkey, a mouse, a rat, a pig, a sheep, or a goat.

Mouse Models of Obesity and Obesity-Associated Disorders

Various animal models exist to study obesity (see, for example, Bray, G. A., 1992, Prog. Brain Res. 93:333-341, and Bray, G. A., 1989, Amer. J. Clin. Nutr. 5:891-902). Animals that have mutations leading to syndromes that include obesity symptoms have also been identified. The best studied animal models for obesity are mice. See reviews, e.g., Friedman, J. M. et al., 1991, Mamm. Gen. 1:130-144; Friedman, J. M. and Liebel, R. L., 1992, Cell 69:217-220, which are each incorporated by reference in their entirety. Mice models of obesity have indicated that obesity is a complex trait with a high degree of heritability. Mutations at a number of loci that lead to obese phenotypes have been identified, and include (but are not limited to) the autosomal recessive mutations obese (ob), diabetes (db), fat (fat) and tubby (tub).

The ob mutation is found on chromosome 6 while the db mutation is located at chromosome 4. Each mutation leads to a clinically similar onset of obesity, starting at about one month of age, with a phenotype typified by hyperphagia, severe abnormalities in glucose and insulin metabolism, poor thermoregulation and non-shivering thermogenesis, and extreme torpor and underdevelopment of the lean body mass. In the db mouse, elevated triiodothyronine levels have also been reported.

The ob gene and its human homologue were cloned by Zhang, Y. et al., (1994, Nature 372:425-432). The ob gene encodes Leptin, a protein of 167 amino acids. It is produced by adipocytes of white adipose tissue, and the level of circulating Leptin is directly proportional to the total amount of fat in the body. In its active form, Leptin is a 16 kDa protein hormone involved in regulating energy intake and energy expenditure, including appetite and metabolism. ob/ob mice have mutations in the gene for Leptin, and are responsive to Leptin treatment.

The db locus encodes a high affinity receptor for the ob gene product, Leptin (Chen, H. et al., Cell. 1996 Feb. 9; 84(3):491-5). The db gene product, the Leptin receptor, is a single membrane-spanning receptor that is closely related to the gp130 cytokine receptor signal transducing component (Tartaglia, L. A. et al., 1995, Cell 83:1263-1271).

Another animal model, the fa/fa (fatty) rat, is similar to the ob/ob mouse and the db/db mouse. However, a fa/fa rat has a normal capacity for non-shivering thermogenesis but are very sensitive to cold. Torpor seems to play a larger part in the maintenance of obesity in fa/fa rats as compared to the ob/ob and db/db mice.

Overview of Diabetes

Obesity, one of the major symptoms in metabolic syndrome, is not only a strong risk factor for the development of Type II diabetes (Abate N, et al., *J Diabetes Complications*, 2000, 14(3):154-74) but also a independent risk factor of coronary heart disease (Wallace A M, et al., *Circulation*, 2001, 104(25):3052-6). The increase of circulating Leptin levels is markedly associated with obesity (Caro J F, et al., *Diabetes*, 1996, 45(11):1455-62; Chu N F, et al., *Int J Obes Relat Metab Disord*, 2000, 24(9):1085-92). The primary physiological function of Leptin is to prevent obesity by regulating food intake and energy balance through activation of its receptors in hypothalamic centers. The elevated levels of plasma Leptin (also referred to as hyperleptinemia) associated with obesity and diabetes implies a resistance to the action of Leptin.

Diabetes mellitus is one of the most prevalent chronic disorders affecting the population worldwide. Diabetes mellitus is a disorder of carbohydrate metabolism, characterized by hyperglycemia and glycosuria, which results from inadequate synthesis or utilization of insulin. Hyperleptinemia and hyperinsulinemia are also characteristic of some types of diabetes, such as Type 11 diabetes (or non-insulin dependent diabetes mellitus, NIDDM; discussed below) Diabetes exists as four categories: Type I diabetes (also referred to as insulin dependent diabetes mellitus, or IDDM), Type II diabetes (NIDDM), gestational diabetes mellitus, and other specific types, wherein each type has a distinct pathogenesis and etiology. In Europe, the United States, and Canada, over 80% of diabetes cases are classified as Type II, and 5-10% are diagnosed as Type I (Carulli L, et al., *Aliment Pharmacol Ther*, 2005, 22 Suppl 2:16-9).

In Type I diabetes, the pancreas fails to produce insulin, which is essential for glucose homeostasis. This form develops typically in children and adolescents, but can also develop later in life. Type II diabetes results from the inability of insulin-responsive tissues to respond properly to the action of insulin, thus are referred to as being insulin-resistant. Type II diabetes occurs most frequently in adults, but an increase in adolescents diagnosed with Type II diabetes has been observed (Carulli L, et al., *Aliment Pharmacol Ther*, 2005, 22 Suppl 2:16-9; Bouche C, et al., *Endoc Rev*, 2004, 25(5): 807-830).

Non-insulin dependent diabetes mellitus (NIDDM), or Type II diabetes, occurs predominantly in adults. These individuals produce adequate levels of insulin but display a defect in insulin-mediated utilization and metabolism of glucose in peripheral tissues, such as in skeletal muscle, brown adipose tissue, and white adipose tissue. NIDDM subjects exhibit overproduction of glucose by the liver, thus contributing to the hyperglycemic state associated with the disorder; impairment of glucose-regulated insulin secretion; and resistance to insulin-mediated glucose disposal, thus also contributing to the hyperglycemic status of the afflicted subject. In NIDDM, insulin secretion is often enhanced in order to compensate for insulin resistance. As the disorder prevails, the pancreatic β-cells fail to sustain sufficient insulin secretion to compensate for the impaired insulin responsiveness. However, mechanisms responsible for the failure of β-cell action have yet to be established, but perhaps can be attributed to hyperglycemic effects and/or to the continuous demands placed on the β-cells by peripheral insulin resistance (Carulli L, et al., *Aliment Pharmacol Ther*, 2005, 22 Suppl 2:16-9; Bouche C, et al., *Endoc Rev*, 2004, 25(5): 807-830).

Subjects who display insulin resistance or are diagnosed as a Type II diabetic often exhibit various symptoms that are referred to as metabolic syndrome, or syndrome X. A subject having this syndrome is characterized as exhibiting three or more symptoms selected from the following group: (1) hypertriglyceridemia; (2) abdominal obesity; (3) low high-density lipoprotein cholesterol (HDL); (4) elevated fasting serum glucose levels; (5) high blood pressure; and (6) hyperleptinemia. NIDDM subjects can display a number of the symptoms described. Syndrome X subjects, whether or not overt diabetes mellitus develops, have an increased risk of developing the microvascular and macrovascular complications that occur in NIDDM subjects, such as atherosclerosis and coronary heart disease (Carulli L, et al., *Aliment Pharmacol Ther*, 2005, 22 Suppl 2:16-9).

Uncontrolled and continuous hyperglycemia connected with diabetes is associated with increased and premature morbidity and mortality. Diabetic subjects, such as those having NIDDM, have a considerable increased risk of macrovascular and microvascular complications, such as coronary heart disease, atherosclerosis, peripheral vascular disease, stroke, hypertension, retinopathy, neuropathy, and nephropathy (Federici M and R Lauro, *Aliment Pharmacol Therapy*, 2005, 22(Suppl 2): 11-15; Desai A S and P T O'Gara, *Indian Heart J*, 2005, 57(4):295-303; Natarajan R and J L Nadler, *Arterioscler Thromb Vasc Biol*, 2004, 24:1542-48). Thus, therapeutic control of obesity, glucose homeostasis, hypertension, and lipid metabolism are critically important in the treatment and clinical management of diabetes mellitus, so as to decrease mortality due to diabetic complications, such as cardiovascular disease.

Insulin and Leptin Signaling

Binding of insulin to its receptor leads to the activation of several mitogenic and metabolic pathways via insulin receptor substrates (IRS 1-4), Gab-1, and Cbl (Sun X J, et al., *Nature*, 1995, 377:173-7; Sun X J, et al., *Nature*, 1991, 352:73-7; Fantin V R, et al., *J Biol Chem*, 1998, 273(17): 10726-32; Berg C E, et al., *Biochem Biophys Res Commun*, 2002, 293(3):1021-7; Holgado-Madruga M, et al., *Nature*, 1996, 379:560-4; Ribon V and A R Saltiel, *Biochem J*, 1997, 324(Pt 3):839-45). Insulin binds to its receptor resulting in autophosphorylation of the β-subunits and phosphorylation of the tyrosine residues of the insulin receptor substrates (such as IRS-1). IRS subsequently phosphorylates the SH2 domain of the tyrosine phosphatase, Shp2, as well as the SH3 domain of the adaptor molecule Grb2. Active Grb2 in turn binds to Sos1, which then activates the Ras signaling pathway and downstream transcription of genes. The IRS protein also activates phosphoinositide 3-kinase (PI3K) via binding to its SH2 domain, resulting in increases in intracellular PIP and PIP levels which leads to the activation of phosphatidylinositol phosphate-dependent kinase-1 (PDK-1). This event thus leads to activating the Akt/PKB pathway, which results in intracellular events, such as translocation of the glucose transporter (GLUT4) from an intracellular pool to the cell surface.

Among the mitogenic and metabolic pathways initiated by the insulin signaling cascade is the phosphatidylinositol 3-kinase (PI3K) pathway (Berman D M, et al., *J Clin Endocrinol Metab*, 2001, 86(1):97-103; Dennis P B, et al., *Mol Cell Biol*, 1996, 16(11):6242-51). In vascular smooth cells (VSMCs), Leptin binds to its receptor and activates both mitogen activated protein kinase (MAPK) and PI3K pathways through phosphorylation of Tyr985 and Tyr1138 residues of the Leptin receptor (Oda A, et al., *Kobe J Med Sci*, 2001, 47(3):141-50). The activated Leptin receptor is known to regulate components of the insulin signaling cascade, such as ERK, Akt, IRS-1, MAP kinase, and PI3-kinase, a cellular action referred to as crosstalk (Niswender K D, et al., *Trends Endocr Metab*, 2004, 15(8):362-9; Myers M G, *Recent Prog Horm Res*, 2004, 59:287-304; Ahima R S and S Y Osei, *Physio Behav*, 2004, 81:223-41). The activation of the PI3K pathway can stimulate the phosphorylation of mTOR via activation of Akt (protein kinase B).

These directly link the hormones insulin and Leptin (an adipokine) to the mTOR pathway. Activation of mTOR leads to the hyperphosphorylation of p70$^{S6K}$ and the eIF-4E binding protein (4E-BP1) driving translation of the 5' terminal oligopyrimidine tract mRNA and releasing eIF-4E to form the eIF-4F complex, respectively (Brunner L et al., *Obes Relat Metab Disord*, 1997, 21(12):1152-60; Cutfield L S, et al., *J Pediatr*, 2003, 142(2):113-6; Sugiyama H, et al., *J Immunol*, 1996, 157(2):656-60; Volarevic S and G Thomas, *Prog Nucleic Acid Res Mol Biol*, 2001, 65:101-27; Hara K, et al., *J Biol Chem*, 1997, 272(42):26457-63; Graves L M, et al., *Proc Natl Acad Sci USA*, 1995, 92(16):7222-6).

Spexin

Spexin is a peptide with GI activity. It was first identified using Markov modeling analysis based on features common to peptide hormones to find new ones in human proteome sequences (Mirabeau et al., (2007) *Genome Res.*, 17: 320-327). It demonstrates contractile effects in a rat stomach explant assay, indicating a biological activity.

Ch12, orf39 (Spexin; ~17,333 bp in humans) maps to locus 12p12.1, which is also defined by microsatellite marker (MS) D12S1042. Locus 12p12.1, which is the site Spexin maps to, has been associated with various phenotypic markers of obesity in various family linkage studies. For example, 12p12.1 has been associated with BMI in whites, with a maximum LOD score of 2.1 (HERITAGE study; Yvon et al; 2001: Obesity Genome Map; Rankinen et al, 2006). MS marker D12S1042 has further been linked to waist circumference, with a maximum LOD score of 2.374 (Oman Family Study, Bayoumi et al, 2008). In addition, linkage with microsatellite marker D12S1042 was significant in a subset of families with high average waist circumference, with a maximum LOD score of 4.45, p=0.0045 for increase in evidence for linkage (Dominican family study; Wang et al; 2009). In one embodiment, a method for detecting the presence of or a predisposition to obesity or an obesity-associated disorder in a human subject comprises obtaining a biological sample from a subject; and detecting whether or not the subject expresses Spexin in combination with displaying phenotypic marker(s) of obesity (BMI, waist circumference, or a combination thereof), as compared to a subject not afflicted with obesity or an obesity-associated disorder. The human Spexin gene is found at a locus which has been linked to obesity-related phenotypes/manifestations in a number of genome-wide association studies. In a further embodiment, a gene in the 12p12.1 locus (and the region defined by microsatellite marker D12S1042), plays a role in obesity. In another embodiment, a genetic alteration in SEQ ID NO: 1 (e.g., a deletion, missense mutation, nonsense mutation, or a combination thereof) alters the expression level or primary sequence of spexin message, and/or protein, leading to defective expression and loss of function. Detection of these changes would be the basis for diagnostic assays.

Spexin is a human hormone, whose under-expression in obesity was identified in obese humans, not mouse models of obesity (see EXAMPLES). In one embodiment, Spexin can be used as a general weight control. In another embodiment, Spexin can be used for appetite regulation. In a further embodiment, Spexin can be used for control of lipodystrophy. In some embodiments, Spexin can be used for reduction of belly fat.

The polypeptide sequence of human Spexin is depicted in SEQ ID NO: 1. The nucleotide sequence of human Spexin is shown in SEQ ID NO: 2. Sequence information related to Spexin is accessible in public databases by GenBank Accession numbers NM_030572 (for mRNA) and NP_085049 (for protein).

SEQ ID NO: 1 is the human wild type amino acid sequence corresponding to Spexin (residues 1-116), wherein the bolded sequence represents the mature peptide sequence:

```
  1   MKGLRSLAAT TLALFLVFVF LGNSSCAPQR LLERRNWTPQ AMLYLKGAQG RRFISDQSRR
 61   KDLSDRPLPE RRSPNPQLLT IPEAATILLA SLQKSPEDEE KNFDQTRFLE DSLLNW
```

SEQ ID NO: 2 is the human wild type nucleotide sequence corresponding to Spexin (nucleotides 1-638), wherein the underscored bolded "ATG" denotes the beginning of the open reading frame:

```
  1   ctgacaagat gtccctgtgg actcccaaac tctactccag atggggaggt gcccttaaca
 61   ccaagatttt aaaagctcca atttcagagc aagagtcgaa aactcacaga taaagttata
121   gttatttcag ggttctgaaa agacgcagaa catgaaggga ctcagaagtc tggcagcaac
181   aaccttggct cttttcctgg tgtttgtttt cctgggaaac tccagctgcg ctccgcagag
241   actgttggag agaaggaact ggactcctca agctatgctc tacctgaaag gggcacaggg
301   tcgccgcttc atctccgacc agagccggag aaaggacctc tccgaccggc cactgccgga
361   agacgaagc ccaaatcccc aactactaac tattccggag gcagcaacca tcttactggc
421   gtcccttcag aaatcaccag aagatgaaga aaaaactttt gatcaaacca gattcctgga
481   agacagtctg cttaactggt gaaaatatac tggattatgt ttaattatgg ttctattctc
541   tttgaaaaca tgaaccatgt gaataaaacc tttggaccct ttttaaaaaa aaaaaaaaaa
601   aaaaaaaaaa aaaaaaaaaa aaaaaaaaaa aaaaaaaa
```

Obesity Signature Genes

This invention provides for the discovery that a number human genes have, for the first time, been identified as a cohort of genes involved in obesity. These genes were identified as being differentially expressed in human obese and normal fat. These genes, now that they have been identified, can be used for a variety of useful methods; for example, they can be used to determine whether a subject is predisposed to obesity or an obesity-associated disorder. The genes identified as part of this obesity gene cohort or group (i.e., Obesity Signature genes or "OS genes") include any gene indicated as being differentially expressed in any one of Tables 7-8.

In one embodiment, the invention provides methods to diagnose obesity or an obesity-associated disorder, as well as methods to treat obesity or an obesity-associated disorder, comprising use of nucleic acids, or proteins encoded by nucleic acids, of the Spexin gene. The method diagnoses the underlying cause of obesity and/or an obesity-related disorder.

In some embodiments, the invention encompasses methods for using OS proteins encoded by a nucleic acid (including, for example, genomic DNA, complementary DNA (cDNA), synthetic DNA, as well as any form of corresponding RNA). For example, an OS protein can be encoded by a recombinant nucleic acid of an OS gene, such as Spexin. The OS proteins of the invention can be obtained from various sources and can be produced according to various techniques known in the art. For example, a nucleic acid that encodes an OS protein can be obtained by screening DNA libraries, or by amplification from a natural source. An OS protein can be a fragment or portion of human Spexin protein. The nucleic acids encoding OS proteins of the invention can be produced via recombinant DNA technology and such recombinant nucleic acids can be prepared by conventional techniques, including chemical synthesis, genetic engineering, enzymatic techniques, or a combination thereof. Non-limiting examples of an OS protein is the polypeptide encoded by the Spexin gene and/or any of the genes listed in any one of Tables 7-8.

In some embodiments, the invention encompasses use of variants of an OS protein, such as Spexin. Such a variant can comprise a naturally-occurring variant due to allelic variations between individuals (e.g., polymorphisms), mutated alleles related to obesity, or alternative splicing forms. In one embodiment, the invention encompasses methods for using a protein or polypeptide encoded by a nucleic acid sequence of an Obesity Signature (OS) gene, such as the sequence shown in SEQ ID NO: 1, or an OS protein or polypeptide encoded by any of the genes listed in any one of Tables 7-8. In another embodiment, the polypeptide can be modified, such as by glycosylations and/or acetylations and/or chemical reaction or coupling, and can contain one or several non-natural or synthetic amino acids. An example of an OS polypeptide has the amino acid sequence shown in SEQ ID NO: 1. In certain embodiments, the invention encompasses variants of a human protein encoded by an Obesity Signature (OS) gene, such as Spexin. Such variants can include those having at least from about 46% to about 50% identity to SEQ ID NO: 1, or having at least from about 50.1% to about 55% identity to SEQ ID NO: 1, or having at least from about 55.1% to about 60% identity to SEQ ID NO: 1, or having from at least about 60.1% to about 65% identity to SEQ ID NO: 1, or having from about 65.1% to about 70% identity to SEQ ID NO: 1, or having at least from about 70.1% to about 75% identity to SEQ ID NO: 1, or having at least from about 75.1% to about 80% identity to SEQ ID NO: 1, or having at least from about 80.1% to about 85% identity to SEQ ID NO: 1, or having at least from about 85.1% to about 90% identity to SEQ ID NO: 1, or having at least from about 90.1% to about 95% identity to SEQ ID NO: 1, or having at least from about 95.1% to about 97% identity to SEQ ID NO: 1, or having at least from about 97.1% to about 99.9% identity to SEQ ID NO: 1.

DNA and Polypeptides, Methods, and Purification Thereof

The present invention utilizes conventional molecular biology, microbiology, and recombinant DNA techniques available to one of ordinary skill in the art. Such techniques are well known to the skilled worker and are explained fully in the literature. See, e.g. "*DNA Cloning: A Practical Approach*," Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" ($3^{rd}$ edition, 2001). One skilled in the art can obtain a protein encoded by an OS gene, such as Spexin, or a variant thereof, in several ways, which include, but are not limited to, isolating the protein via biochemical means or expressing a nucleotide sequence encoding the protein of interest by genetic engineering methods. For example, Spexin, or a variant thereof, can be obtained by purifying it from human cells expressing Spexin, or by direct chemical synthesis.

Host cells which contain a nucleic acid encoding an OS polypeptide (e.g., Spexin), and which subsequently express a protein encoded by an OS gene (e.g., Spexin), can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a Spexin polypeptide can be detected by DNA-DNA or DNA-RNA hybridization or amplification using probes or fragments of nucleic acids encoding a Spexin polypeptide.

Amplification methods include, e.g., polymerase chain reaction, PCR (*PCR Protocols, a Guide to Methods and Applications*, ed. Innis, Academic Press, N.Y., 1990 and *PCR Strategies*, 1995, ed. Innis, Academic Press, Inc., N.Y., ligase chain reaction (LCR) (see, e.g., Wu, Genomics 4:560, 1989; Landegren, Science 241:1077, 1988; Barringer, Gene 89:117, 1990); transcription amplification (see, e.g., Kwoh, Proc. Natl. Acad. Sci. USA 86:1173, 1989); and, self-sustained sequence replication (see, e.g., Guatelli, Proc. Natl. Acad. Sci. USA 87:1874, 1990); Q Beta replicase amplification (see, e.g., Smith, J. Clin. Microbiol. 35:1477-1491, 1997), automated Q-beta replicase amplification assay (see, e.g., Burg, Mol. Cell. Probes 10:257-271, 1996) and other RNA polymerase mediated techniques (e.g., NASBA, Cangene, Mississauga, Ontario); see also Berger, Methods Enzymol. 152:307-316, 1987; Sambrook; Ausubel; U.S. Pat. Nos. 4,683,195 and 4,683,202; Sooknanan, Biotechnology 13:563-564, 1995. All the references and patents stated herein are each incorporated by reference in their entireties.

A guide to the hybridization of nucleic acids is found in e.g., Sambrook, ed., *Molecular Cloning: A Laboratory Manual* ($3^{rd}$ Ed.), Vols. 1-3, Cold Spring Harbor Laboratory, 2001; *Current Protocols In Molecular Biology*, Ausubel, ed.

John Wiley & Sons, Inc., New York, 1997; *Laboratory Techniques In Biochemistry And Molecular Biology: Hybridization With Nucleic Acid Probes, Part L Theory and Nucleic Acid Preparation,* Tijssen, ed. Elsevier, N.Y., 1993. All the references stated herein are each incorporated by reference in their entireties.

In one embodiment, a fragment of a nucleic acid of the Spexin gene can encompass any portion of at least about 8 consecutive nucleotides of SEQ ID NO: 2. In another embodiment, the fragment can comprise at least about 10 consecutive nucleotides, at least about 15 consecutive nucleotides, at least about 20 consecutive nucleotides, or at least about 30 consecutive nucleotides of SEQ ID NO: 2. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding a polypeptide encoded by an OS gene (e.g., Spexin), or are complimentary to it, to detect transformants which contain a nucleic acid encoding an OS protein or polypeptide, e.g., Spexin.

Methods for detecting and quantifying OS polypeptides (e.g., a Spexin polypeptide) and OS polynucleotides (e.g., a Spexin polynucleotide) in biological samples are known the art. For example, protocols for detecting and measuring the expression of a polypeptide encoded by an OS gene, such as Spexin, using either polyclonal or monoclonal antibodies specific for the polypeptide are well established. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by an OS gene (e.g, Spexin) can be used, or a competitive binding assay can be employed. In one embodiment, expression of, under-, or over-expression of an OS gene product (e.g., a Spexin polypeptide or Spexin mRNA) can be determined. In one embodiment, a biological sample comprises, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines). In further embodiments, the tissue sample is adipose tissue. In specific embodiments, the adipose tissue is omental adipose, subcutaneous adipose, or mesenteric adipose. The methods of detecting or quantifying Spexin polynucleotides include, but are not limited to, amplification-based assays with signal amplification) hybridization based assays and combination amplification-hybridization assays. For detecting and quantifying Spexin polypeptides, an exemplary method is an immunoassay that utilizes an antibody or other binding agents that specifically bind to a Spexin polypeptide or epitope, for example, ELISA or RIA assays.

Labeling and conjugation techniques are known by those skilled in the art and can be used in various nucleic acid and amino acid assays. Methods for producing labeled hybridization or PCR probes for detecting sequences related to nucleic acid sequences encoding an OS protein, such as Spexin, include, but are not limited to, oligolabeling, nick translation, end-labeling, or PCR amplification using a labeled nucleotide. Alternatively, a nucleic acid sequence encoding a polypeptide encoded by an OS gene can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

Host cells transformed with a nucleic acid sequence encoding an OS polypeptide, such as Spexin, can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding an OS polypeptide can be designed to contain signal sequences which direct secretion of soluble polypeptide molecules encoded by an OS gene, such as Spexin, or a variant thereof, through a prokaryotic or eukaryotic cell membrane, or which direct the membrane insertion of a membrane-bound polypeptide molecule encoded by an OS gene or a variant thereof.

Other constructions can also be used to join a gene sequence encoding an OS polypeptide (e.g., Spexin) to a nucleotide sequence encoding a polypeptide domain which would facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Cleavable linker sequences (i.e., those specific for Factor Xa or enterokinase (Invitrogen, San Diego, Calif.)) can be included between the purification domain and a polypeptide encoded by an OS gene to facilitate purification. One such expression vector provides for expression of a fusion protein containing a polypeptide encoded by an OS gene (e.g., Spexin) and 6 histidine residues preceding a thioredoxin or an enterokinase cleavage site. The histidine residues facilitate purification by immobilized metal ion affinity chromatography, while the enterokinase cleavage site provides a means for purifying the polypeptide encoded by an OS gene.

An OS polypeptide (e.g., Spexin) can be purified from any human or non-human cell which expresses the polypeptide, including those which have been transfected with expression constructs that express an OS protein. A purified OS polypeptide (e.g., Spexin) can be separated from other compounds which normally associate with the OS polypeptide (e.g., Spexin) in the cell, such as certain proteins, carbohydrates, or lipids, using methods practiced in the art. Non-limiting methods include size exclusion chromatography, ammonium sulfate fractionation, ion exchange chromatography, affinity chromatography, and preparative gel electrophoresis.

Nucleic acid sequences comprising an OS gene (e.g., Spexin) that encode a polypeptide can be synthesized, in whole or in part, using chemical methods known in the art. Alternatively, an OS polypeptide, such as Spexin, can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer).

Optionally, fragments of OS polypeptides can be separately synthesized and combined using chemical methods to produce a full-length molecule. In one embodiment, a fragment of a nucleic acid sequence that comprises an OS gene can encompass any portion of at least about 8 consecutive nucleotides of SEQ ID NO: 2. In one embodiment, the fragment can comprise at least about 10 nucleotides, at least about 15 nucleotides, at least about 20 nucleotides, or at least about 30 nucleotides of SEQ ID NO: 2. Fragments include all possible nucleotide lengths between about 8 and about 100 nucleotides, for example, lengths between about 15 and about 100 nucleotides, or between about 20 and about 100 nucleotides.

An OS fragment can be a fragment of an OS protein, such as the Spexin protein. For example, the Spexin fragment can encompass any portion of at least about 8 consecutive amino acids of SEQ ID NO: 1. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, or at least about 75 consecutive amino acids of SEQ ID NO: 1. Fragments include all possible amino acid lengths between about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids.

A synthetic peptide can be substantially purified via high performance liquid chromatography (HPLC). The composition of a synthetic OS polypeptide can be confirmed by amino acid analysis or sequencing. Additionally, any portion of an amino acid sequence comprising a protein encoded by an OS gene (e.g., Spexin) can be altered during direct synthesis and/or combined using chemical methods with sequences from other proteins to produce a variant polypeptide or a fusion protein.

Screening to Identify Compounds that Ameliorate Obesity

The invention provides methods for identifying compounds which can be used for treating obesity or an obesity-associated disorder. The invention also provides methods for identifying compounds which can be used to promote weight loss in an obese subject or a subject afflicted with an obesity-associated disorder. The invention further provides methods for identifying compounds that can be used for promoting satiety in an obese subject or a subject afflicted with an obesity-associated disorder. Since the invention has identified genes that are differentially expressed in obese and normal fat (e.g., Spexin as well as those Obesity Signature genes listed in Tables 7-8), the invention also provides methods for identifying compounds that modulate the expression or activity of an OS gene and/or OS protein, such as Spexin.

Animal models of obesity, such as ob/ob and db/db mice, can be used to identify compounds (e.g., test agents) that ameliorate symptoms of obesity and obesity-associated disorders, e.g., excess body fat, elevated serum Leptin levels, decreased serum Spexin levels, or a combination thereof. Such animal models can be used as test substrates for the identification of drugs, pharmaceuticals, therapies, and interventions which can be effective in treating obesity and obesity-associated disorders. For example, animal models can be exposed to a compound, suspected of exhibiting an ability to ameliorate symptoms of obesity and obesity-associated disorders, e.g., excess body fat, elevated serum Leptin levels, decreased serum Spexin levels, or a combination thereof, at a sufficient concentration and for a time sufficient to elicit such an amelioration of symptoms in the exposed animals. The response of the animals to the exposure can be monitored by assessing the reversal of excess body fat, elevated serum Leptin levels, or decreased serum Spexin levels associated with obesity and obesity-associated disorders.

A gut explant assay can also be used to identify test agents that ameliorate symptoms of obesity and obesity-associated disorders, e.g., excess body fat, elevated serum Leptin levels, decreased serum Spexin levels, or a combination thereof. According to Mirabeau et al., ((2007) *Genome Res.*, 17: 320-327), strips of stomach fundus muscles can be harvested from rats and mounted in an oxygenated organ bath, where they can be stretched and challenged with bioactive agents, thereby serving as a useful bioassay system. At the beginning of each experiment, acetylcholine chloride is applied to achieve a maximal control contraction, the contractions are recorded. In one embodiment, a synthetic amidated spexin peptide (NWTPQAMLYLKGAQ-amide [SEQ ID NO: 32]; Primm; see Mirabeau et al., (2007) *Genome Res.*, 17: 320-327) can be applied. To identify an agonist with properties similar to Spexin, for example, single doses of a test agent can then be applied until reproducible responses, if any, are obtained. To identify an antagonist of Spexin, for example, single doses of a test agent can then be applied until the Spexin responses illicited in the gut explant essay are diminished.

Test compounds or agents of the invention comprise peptides (such as antibodies or fragments thereof or soluble peptides), small molecules (e.g., small organic and small inorganic molecules), nucleic acids (such as siRNA or antisense RNA), or other agents that can bind to a polypeptide molecule encoded by an OS gene (e.g., Spexin) and/or have a stimulatory or inhibitory effect on the biological activity of a protein encoded by an OS gene or its expression (e.g., Spexin). It will then be determined whether the test agents can promote satiety or weight loss in an obese subject or subject afflicted with an obesity-associated disorder, or whether the test agent can be used in the treatment of obesity or an obesity-associated disorder (e.g., by examining whether there is a change in a body weight phenotype, such as a reduction in body fat mass).

As used herein, a "Spexin modulating compound" refers to a compound that interacts with the Spexin gene, or the Spexin protein or polypeptide, and modulates its activity and/or its expression. The compound can either increase the activity or expression of a Spexin protein. Conversely, the compound can decrease the activity or expression of a Spexin protein. The compound can be a Spexin agonist or a Spexin antagonist. Some non-limiting examples of Spexin modulating compounds include peptides (such as peptide fragments comprising SEQ ID NO: 1, or antibodies or fragments thereof), small molecules (organic or inorganic), and nucleic acids (such as siRNA or antisense RNA specific for a nucleic acid comprising SEQ ID NO: 2). Spexin agonists can be molecules which, when bound to Spexin or its receptor, increase or prolong the activity of the Spexin protein. Spexin agonists can be compounds (e.g., synthetic compounds or other naturally occurring peptides) that elicit the same or similar activity as compared to Spexin. Spexin agonists include, but are not limited to, proteins, nucleic acids, small molecules, or any other molecule which activates the Spexin protein. Spexin antagonists can be molecules which, when bound to the Spexin protein, decrease the amount or the duration of the activity of Spexin. Antagonists include proteins, nucleic acids, antibodies, small molecules, or any other molecule which decrease the activity of the Spexin protein.

"Modulate" refers to a change in the activity or expression of an OS gene or protein, such as Spexin. For example, modulation can cause an increase or a decrease in protein activity, binding characteristics, or any other biological, functional, or immunological property of an OS protein. In one embodiment, the OS protein is Spexin.

In one embodiment, a Spexin modulating compound can be a peptide fragment of the Spexin protein that binds to Spexin itself. For example, it can encompass any portion of at least about 8 consecutive amino acids of SEQ ID NO: 1. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of SEQ ID NO: 1. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) Solid Phase Peptide Synthesis: a Practical Approach. IRL Press, Oxford, England). The Spexin peptide fragments can be isolated from a natural source, genetically engineered, or chemically prepared. These methods are well known in the art.

A Spexin modulating compound can be a protein, such as an antibody (monoclonal, polyclonal, humanized, chimeric, or fully human), or a binding fragment thereof, directed against a polypeptide encoded by the Spexin gene. An antibody fragment can be a form of an antibody other than the full-length form and includes portions or components that exist within full-length antibodies. An antibody fragment can also be an antibody fragment that has been engineered. Antibody fragments can include, but are not limited to, single chain Fv (scFv), diabodies, Fv, (Fab')2, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) Ann. Rev. Biomed. Eng. 2:339-76; Hudson (1998) Curr. Opin. Biotechnol. 9:395-402). Antibodies can be obtained commercially, can be custom generated, or can be synthesized against an antigen of interest according to methods established in the art (e.g., see Beck et al., Nat Rev Immunol. 2010 May; 10(5):345-52; Chan et al., Nat Rev Immunol. 2010 May; 10(5):301-16; and Kontermann, Curr Opin Mol Ther. 2010 April; 12(2):176-83, each of which are incorporated by reference in their entireties).

Inhibition of RNA encoding a polypeptide encoded by an OS gene, e.g., Spexin) can effectively modulate the expression of an OS gene from which the RNA is transcribed. Inhibitors are selected from the group comprising: siRNA; interfering RNA or RNAi; dsRNA; RNA Polymerase III transcribed DNAs; ribozymes; and antisense nucleic acids, which can be RNA, DNA, or an artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a Spexin polypeptide can be synthesized, e.g., by conventional phosphodiester techniques (Dallas et al., (2006) Med. Sci. Monit.12(4):RA67-74; Kalota et al., (2006) Handb. Exp. Pharmacol. 173:173-96; Lutzelburger et al., (2006) Handb. Exp. Pharmacol. 173:243-59). Antisense nucleotide sequences include, but are not limited to: morpholinos, 2'-O-methyl polynucleotides, DNA, RNA and the like.

siRNA comprises a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. See also, McMnaus and Sharp (2002) Nat Rev Genetics, 3:737-47, and Sen and Blau (2006) FASEB J., 20:1293-99, the entire disclosures of which are herein incorporated by reference.

The siRNA can be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3' overhang. As used herein, a 3' overhang refers to at least one unpaired nucleotide extending from the 3'-end of a duplexed RNA strand. For example, the siRNA can comprise at least one 3' overhang of from 1 to about 6 nucleotides (which includes ribonucleotides or deoxyribonucleotides) in length, or from 1 to about 5 nucleotides in length, or from 1 to about 4 nucleotides in length, or from about 2 to about 4 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector (for example, see U.S. Pat. Nos. 7,294,504, 7,148,342, and 7,422,896, the entire disclosures of which are herein incorporated by reference). Exemplary methods for producing and testing dsRNA or siRNA molecules are described in U.S. Patent Application Publication No. 2002/0173478 to Gewirtz, and in U.S. Patent Application Publication No. 2007/0072204 to Hannon et al., the entire disclosures of which are herein incorporated by reference.

RNA polymerase III transcribed DNAs contain promoters, such as the U6 promoter. These DNAs can be transcribed to produce small hairpin RNAs in the cell that can function as siRNA or linear RNAs that can function as antisense RNA. The Spexin modulating compound can contain ribonucleotides, deoxyribonucleotides, synthetic nucleotides, or any suitable combination such that the target RNA and/or gene is inhibited. In addition, these forms of nucleic acids can be single, double, triple, or quadruple stranded. (see for example Bass (2001) Nature, 411, 428 429; Elbashir et al., (2001) Nature, 411, 494 498; and PCT Publication Nos. WO 00/44895, WO 1/36646, WO 99/32619, WO 00/01846, WO 01/29058, WO 99/07409, WO 00/44914). In one embodiment, short hairpin RNAs can be synthesized exogenously or can be formed by transcribing from RNA polymerase III promoters in vivo. Examples of making and using such shRNAs for gene silencing in mammalian cells are described in, for example, Paddison et al., 2002, *Genes Dev*, 16:948-58; McCaffrey et al., 2002, Nature, 418:38-9; McManus et al., 2002, *RNA*, 8:842-50; Yu et al., 2002, *Proc Natl Acad Sci USA*, 99:6047-52). shRNAs are engineered in cells or in an animal to ensure continuous and stable suppression of a desired gene. It is known in the art that siRNAs can be produced by processing a hairpin RNA in the cell.

A Spexin modulating compound can be a small molecule that binds to the Spexin protein and disrupts its function, or conversely, enhances its function. Small molecules are a diverse group of synthetic and natural substances generally having low molecular weights. They can be isolated from natural sources (for example, plants, fungi, microbes and the like), are obtained commercially, are available as libraries or collections, or can be synthesized. Candidate small molecules that modulate Spexin can be identified via in silico screening or high-through-put screening (HTPS) of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) Brief Funct. Genomic Proteomic 5(1):32-6).

Knowledge of the primary sequence of a molecule of interest, such as a polypeptide encoded the Spexin gene, and the similarity of that sequence with proteins of known function, can provide information as to the inhibitors or antagonists of the protein of interest, in addition to agonists. Identification and screening of agonists and antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Test agents, e.g., Spexin modulating compounds, can be screened from large libraries of synthetic or natural compounds (see Wang et al., (2007) Curr Med Chem, 14(2): 133-55; Mannhold (2006) Curr Top Med Chem, 6 (10): 1031-47; and Hensen (2006) Curr Med Chem 13(4):361-76). Numerous means are currently used for random and directed synthesis of saccharide, peptide, and nucleic acid based compounds. Synthetic compound libraries are commercially available from Maybridge Chemical Co. (Trevillet, Cornwall, UK), AMRI (Albany, N.Y.), ChemBridge (San Diego, Calif.), and MicroSource (Gaylordsville, Conn.). A rare chemical library is available from Aldrich (Milwaukee, Wis.). Alternatively, libraries of natural compounds in the form of bacterial, fungal, plant, and animal extracts are available from, e.g., Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Treatment of Obesity and Obesity-Associated Disorders

Several well-established obesity treatments ranging from non-pharmaceutical to pharmaceutical intervention are known in the art. Non-pharmaceutical interventions include, but are not limited to, dietary restriction, exercise, psychiatric treatment, and surgical treatments to reduce food consumption (e.g., bariatric surgery) or remove fat (e.g., liposuction). Present pharmacological interventions can induce a weight loss of between 5 to 15 kg. Appetite suppressants and energy expenditure or nutrient-modifying agents are the main focus of pharmacological intervention. Dexfenfluramine (Redux), sibutramine (Meridia), beta3-adrenergic agonists, sympathomimetic adrenergic agents (such as amphetamines (dextroamphetamine)), phentermine, benzphetamine, phendimetrazine, mazindol, diethylpropion, phenylpropanolamine, serotonin (5-HT) reuptake inhibitors (such as sibutramine), and gastrointestinal lipases (such as orlistat) are examples of such pharmacological interventions. See also, Bays, (2004) Obesity Research 12(8):1197-1211, and Klonoff et al., J Diabetes Sci Technol. 2008 September; 2(5):913-8, the contents of each which are incorporated by reference in their entireties. However, if the medication is discontinued, renewed weight gain can ensue.

Surgical treatments are comparatively successful, but are complicated, expensive, and have significant risks. Surgical treatments are reserved for patients with extreme obesity and/or with serious medical complications.

In one embodiment, Spexin is administered to an obese subject to treat obesity or an obesity-associated disorder. In another embodiment, a polypeptide comprising SEQ ID NO: 1, or a pharmaceutically acceptable salt thereof is administered to an obese subject to treat obesity or an obesity-associated disorder. In one embodiment, Spexin is administered to an obese subject or a subject afflicted with an obesity-associated disorder to promote weight loss in the subject. In another embodiment, a polypeptide comprising SEQ ID NO: 1, or a pharmaceutically acceptable salt thereof is administered to an obese subject or a subject afflicted with an obesity-associated disorder to promote weight loss in the subject. In one embodiment, Spexin is administered to an obese subject or a subject afflicted with an obesity-associated disorder to promote satiety in the subject. In another embodiment, a polypeptide comprising SEQ ID NO: 1, or a pharmaceutically acceptable salt thereof is administered to an obese subject or a subject afflicted with an obesity-associated disorder to promote satiety in the subject.

Spexin, a polypeptide comprising SEQ ID NO: 1, or a pharmaceutically acceptable salt thereof, or a test agent of the invention (e.g., a small organic molecule, a small inorganic molecule, a soluble peptide, or an antibody) can be administered in a therapeutically effective amount. For example, an amount that is sufficient to treat obesity or the obesity-associated disorder, such as by ameliorating symptoms associated with obesity or the obesity-associated disorder (e.g., elevated Leptin levels, decreased spexin levels, and increased body mass), preventing or delaying the onset of obesity or the obesity-associated disorder, and/or also lessening the severity or frequency of symptoms of obesity or the obesity-associated disorder (e.g., elevated Leptin levels, decreased spexin levels, and increased body mass).

The amount which will be therapeutically effective in the treatment of a particular individual's disorder or condition will depend on the symptoms and severity of the disease, and can be determined by standard clinical techniques. In vitro or in vivo assays can also be used to identify optimal dosage ranges. The precise dose to be used in the formulation will also depend on the route of administration, and the severity of the obesity or the obesity-associated disorder, and should be decided according to the judgment of a practitioner and each patient's circumstances. Effective doses can be extrapolated from dose-response curves derived from in vitro or animal model test systems, such as a db/db mouse, an ob/ob mouse, or a High-fat-diet-fed mouse model (e.g., the Diet Induced Obesity (DIO) mouse model).

Spexin is a peptide hormone that has biological activity in the gut but is noticeably under-expressed by both omental and subcutaneous fat in obese patients (see EXAMPLES). In one embodiment, Spexin is a satiety factor. Spexin, or a small molecule acting through the same receptor/signaling system, can be used to inhibit food cravings and regulate caloric intake.

A satiety factor is a feedback signal related to energy expenditure and food intake. A satiety factor is involved in regulating appetite, food intake, energy intake or expenditure, or acts as a satiety signal. The satiety factor studied most to date is the hormone Leptin, which is synthesized and secreted predominantly by fat cells. In one embodiment, Spexin is a satiety factor. In a further embodiment, Spexin as a satiety factor can be used for the treatment of obesity.

In another embodiment, Spexin can be an alternative and/or complement to surgical treatments to reduce food consumption (e.g., bariatric surgery) or remove fat (e.g., liposuction).

Treatment of Other Body Weight Disorders

Obesity is the most prevalent of body weight disorders. Other body weight disorders, such as anorexia nervosa and bulimia nervosa, also are serious health threats. Further, such body weight disorders as anorexia, lipodystrophy, and cachexia (wasting) are also prominent characteristics of other diseases such as cancer, cystic fibrosis, tuberculosis, congestive heart failure, and AIDS. An aspect of the invention provides for a method of diagnosing a body weight disorder in a subject. In one embodiment, excess of Spexin production or circulating Spexin is responsible for anorexia nervosa, or other eating disorders. In one embodiment, the method for diagnosing a body weight disorder in a human subject comprises: (a) obtaining a biological sample from a subject; and (b) detecting whether or not there is an alteration in the expression of the Spexin gene in the subject as compared to a subject not afflicted with a body weight disorder.

Wasting is a syndrome characterized by loss of weight, muscle atrophy, fatigue, weakness, and significant loss of appetite in a subject who is not actively trying to lose weight.

Lipodystrophy is a medical condition characterized by abnormal or degenerative conditions of the body's adipose tissue. It is characterized by a lack of circulating Leptin which can lead to osteosclerosis.

Spexin can play a role in the pathogenesis of, or treatment of, lipodystrophy in HIV-infected patients. Thus, serum levels of Spexin can be regulated in HIV+ patients. In one embodiment, a Spexin antagonist is administered to a subject to treat lipodystrophy. In another embodiment, a polypeptide directed to the amino acid comprising SEQ ID NO: 1 (e.g., a Spexin antibody) is administered to a subject to treat lipodystrophy. In one embodiment, a Spexin antagonist is administered to a subject or to promote weight gain in the subject. In another embodiment, a polypeptide directed to the amino acid comprising SEQ ID NO: 1 (e.g., a Spexin antibody) is administered to a subject to promote weight gain in the subject.

Symptoms of these body weight disorders characterized by a lower than normal body weight phenotype (for example, cachexia or lipodystrophy) can be ameliorated by decreasing the level of Spexin gene expression and/or spexin gene product activity. For example, Spexin gene sequences (for example, SEQ ID NO: 2) can be utilized in conjunction with an antisense, a gene "knock-out," ribozyme and/or a siRNA method to decrease the level of spexin gene expression. In one embodiment, an antibody directed to the Spexin protein can neutralize Spexin activity by way of binding to the Spexin protein.

Administration and Dosing

Spexin or a Spexin modulating compound can be administered to the subject one time (e.g., as a single injection or deposition). Alternatively, Spexin or a Spexin modulating compound of the invention can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. Furthermore, Spexin or a Spexin modulating compound can be co-administrated with another therapeutic, such as dexfenfluramine (Redux), sibutramine (Meridia), a beta3-adrenergic agonist, a sympathomimetic adrenergic agent (such as amphetamines (dextroamphetamine)), phentermine, benzphetamine, phendimetrazine, mazindol, diethylpropion, phenylpropanolamine, a serotonin (5-HT) reuptake inhibitor (such as sibutramine), a gastrointestinal lipase (such as orlistat), a satiety factor, or a combination thereof.

Spexin or a Spexin modulating compound of the invention can be administered to a subject by any means suitable for delivering Spexin or a Spexin modulating compound to cells of the subject, such as omental adipose cells or subcutaneous adipose cells. For example, Spexin or a Spexin modulating compound can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with obesity or an obesity-associated disorder by any means that produce contact of the active ingredient with the agent's site of action in the body of a human or non-human subject. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (20$^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Pharmaceutical formulations of the invention can comprise Spexin or a Spexin modulating compound (e.g., 0.1 to 90% by weight), or a physiologically acceptable salt thereof, mixed with a pharmaceutically-acceptable carrier. The pharmaceutical formulations of the invention can also comprise Spexin or a Spexin modulating compound of the invention which are encapsulated by liposomes and a pharmaceutically-acceptable carrier. Useful pharmaceutically-acceptable carriers are water, buffered water, normal saline, 0.4% saline, 0.3% glycine, or hyaluronic acid.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, or magnesium carbonate.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, or magnesium carbonate. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, or sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides, small molecules, or polypeptides of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix, Pharm Res. 13: 1760-1764, 1996; Samanen, J. Pharm. Pharmacol. 48: 119-135, 1996; U.S. Pat. No. 5,391,377, describing lipid compositions for oral delivery of therapeutic agents (for example, liposomal delivery). In one embodiment, Spexin or a Spexin modulating compound can be delivered to the alimentary canal or intestine of the subject via oral administration that is can withstand digestion and degradation.

For oral administration, the therapeutic compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active agent. For buccal administration the therapeutic compositions can take the form of tablets or lozenges formulated in a conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflate or can be formulated containing a powder mix of the therapeutic agents and a suitable powder base such as lactose or starch.

Spexin or a Spexin modulating compound can be delivered in a controlled release system. For example, the polypeptide can be administered using intravenous infusion, an implantable osmotic pump, a transdermal patch, liposomes, or other modes of administration. In one embodiment, a pump can be used (see is Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The therapeutic compositions can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Suitable enteral administration routes for the present methods include oral, rectal, or intranasal delivery. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. For example, Spexin or a Spexin modulating compound of the invention can be administered by injection, infusion, or oral delivery.

In addition to the formulations described previously, the therapeutic compositions can also be formulated as a depot preparation. Such long acting formulations can be administered by implantation (for example subcutaneously or intramuscularly) or by intramuscular injection. For example, the therapeutic compositions can be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents can be used to facilitate permeation. Transmucosal administration can be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

A composition of the present invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the present invention.

In the present methods, Spexin or a Spexin modulating compound can be administered to the subject either as RNA, in conjunction with a delivery reagent, or as a nucleic acid (e.g., a recombinant plasmid or viral vector) comprising sequences which expresses the gene product. Suitable delivery reagents for administration of Spexin or a Spexin modulating compound include the Mirus Transit TKO lipophilic reagent; lipofectin; lipofectamine; cellfectin; or polycations (e.g., polylysine), or liposomes.

The dosage administered can be a therapeutically effective amount of the composition sufficient to result in amelioration of symptoms of obesity or an obesity-associated disorder in a subject, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In one embodiment, Spexin is administered at a dose so as to achieve a plasma concentration of about 10 ng/ml to about 20 ng/ml in obese patients or patients afflicted with an obesity-associated disorder. In some embodiments, the effective amount of the administered Spexin is at least about 1 ng/ml, at least about 2 ng/ml, at least about 3 ng/ml, at least about 4 ng/ml, at least about 5 ng/ml, at least about 7.5 ng/ml, at least about 10 ng/ml, at least about 15 ng/ml, at least about 20 ng/ml, at least about 25 ng/ml, at least about 30 ng/ml, at least about 35 ng/ml, at least about 40 ng/ml, at least about 45 ng/ml, at least about 50 ng/ml, at least about 60 ng/ml, at least about 70 ng/ml, at least about 80 ng/ml, at least about 90 ng/ml, at least about 100 ng/ml, at least about 125 ng/ml, at least about 150 ng/ml, at least about 175 ng/ml, at least about 200 ng/ml, at least about 250 ng/ml, at least about 300 ng/ml, at least about 350 ng/ml, at least about 400 ng/ml, at least about 450 ng/ml, at least about 500 ng/ml, at least about 600 ng/ml, at least about 700 ng/ml, at least about 800 ng/ml, at least about 900 ng/ml, at least about 1000 ng/ml, at least about 1250 ng/ml, at least about 1500 ng/ml, at least about 1750 ng/ml, at least about 2000 ng/ml, at least about 2500 ng/ml, at least about 2750 ng/ml, at least about 3000 ng/ml, at least about 3500 ng/ml, at least about 3750 ng/ml, at least about 5000 ng/ml, at least about 7500 ng/ml, or at least about 10,000 ng/ml. In one embodiment, Spexin is administered at a dose of 0.2 ml of Spexin a day (2500 ng/mL). In another embodiment, Spexin is administered by daily intraperitoneal (IP) injection.

In other embodiments, the effective amount of the administered Spexin modulating compound is at least about 0.01 µg/kg body weight, at least about 0.025 µg/kg body weight, at least about 0.05 µg/kg body weight, at least about 0.075 µg/kg body weight, at least about 0.1 µg/kg body weight, at least about 0.25 µg/kg body weight, at least about 0.5 µg/kg body weight, at least about 0.75 µg/kg body weight, at least about 1 µg/kg body weight, at least about 5 µg/kg body weight, at least about 10 µg/kg body weight, at least about 25 µg/kg body weight, at least about 50 µg/kg body weight, at least about 75 µg/kg body weight, at least about 100 µg/kg body weight, at least about 150 µg/kg body weight, at least about 200 µg/kg body weight, at least about 250 µg/kg body weight, at least about 300 µg/kg body weight, at least about 350 µg/kg body weight, at least about 400 µg/kg body weight, at least about 450 µg/kg body weight, at least about 500 µg/kg body weight, at least about 550 µg/kg body weight, at least about 600 µg/kg body weight, at least about 650 µg/kg body weight, at least about 700 µg/kg body weight, at least about 750 µg/kg body weight, at least about 800 µg/kg body weight, at least about 850 µg/kg body weight, at least about 900 µg/kg body weight, at least about 950 µg/kg body weight, or at least about 1000 µg/kg body weight. In one embodiment, the effective amount of the administered Spexin modulating compound is at least about 10 µg/kg body weight.

In one embodiment, Spexin or a Spexin modulating compound is administered at least once daily. In another embodiment, Spexin or a Spexin modulating compound is administered at least twice daily. In some embodiments, Spexin or a Spexin modulating compound is administered for at least 1 week, for at least 2 weeks, for at least 3 weeks, for at least 4 weeks, for at least 5 weeks, for at least 6 weeks, for at least 8 weeks, for at least 10 weeks, or for at least 12 weeks. In further embodiments, Spexin and/or a Spexin modulating compound is administered in combination with a second therapeutic agent.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

A therapeutically effective dose of Spexin or a Spexin modulating compound can depend upon a number of factors known to those of ordinary skill in the art. The dose(s) of Spexin or a Spexin modulating compound can vary, for example, depending upon the identity, size, and condition of the subject or sample being treated, further depending upon the route by which the composition is to be administered, if applicable, and the effect which the practitioner desires Spexin or a Spexin modulating compound to have upon the nucleic acid or polypeptide of the invention. These amounts can be readily determined by a skilled artisan.

Gene Therapy and Protein Replacement Methods

The invention provides methods for treating obesity or an obesity-associated disorder in a subject. In one embodiment, the method can comprise administering to the subject Spexin or a Spexin modulating compound, which can be a polypeptide, small molecule, antibody, or a nucleic acid.

Various approaches can be carried out to restore the activity or function of an Obesity Signature (OS) genes (e.g., Spexin) in a subject, such as those carrying an altered Spexin gene locus. For example, supplying wild-type Spexin function to such subjects can suppress phenotypic expression of obesity or an obesity related disorder in a subject. Increasing Spexin expression levels or activity can be accomplished through gene or protein therapy.

A nucleic acid encoding an OS gene, or a functional part thereof (such as Spexin) can be introduced into the cells of a subject. For example, the wild-type Spexin gene (or a functional part thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. For example, a functional copy of the Spexin gene can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Delivery of nucleic acids into viable cells can be effected ex vivo, in situ, or in vivo by use of vectors, and more specifically viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Biandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; and U.S. Application Publication Nos. 2002/0077313 and 2002/00069, which are all hereby incorporated by reference in their entireties. For additional reviews of gene therapy technology, see Friedmann, Science, 244: 1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

Protein replacement therapy can increase the amount of protein by exogenously introducing wild-type or biologically functional protein by way of infusion. A replacement polypeptide can be synthesized according to known chemical techniques or can be produced and purified via known molecular biological techniques. Protein replacement therapy has been developed for various disorders. For example, a wild-type protein can be purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

These methods described herein are by no means all-inclusive, and further methods to suit the specific application is understood by the ordinary skilled artisan. Moreover, the effective amount of the compositions can be further approximated through analogy to compounds known to exert the desired effect.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided herein to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Identification of Spexin as a Potential Satiety Factor that is Approximately 15 Fold Underexpressed in Omental and Subcutaneous Fat in Obese Patients Human and mouse models of obesity for serum levels of Spexin via radioimmunoassay (RIA) are being tested to see if circulating spexin levels correlate with tissue depot expression levels. Also, western blots of human tissues are being carried out to measure expression levels, and to determine molecular weights of expressed peptides. The genomic sequence and expressed mRNA of Spexin from human sources (both obese and normal) is being characterized to see if sequence variants (e.g., SNPs, insertions, deletions, etc) account for differential expression of Spexin, or if unknown splice variants of Spexin exist, that are not recognized by the probe on the Codelink arrays used in these studies.

Figure 9:
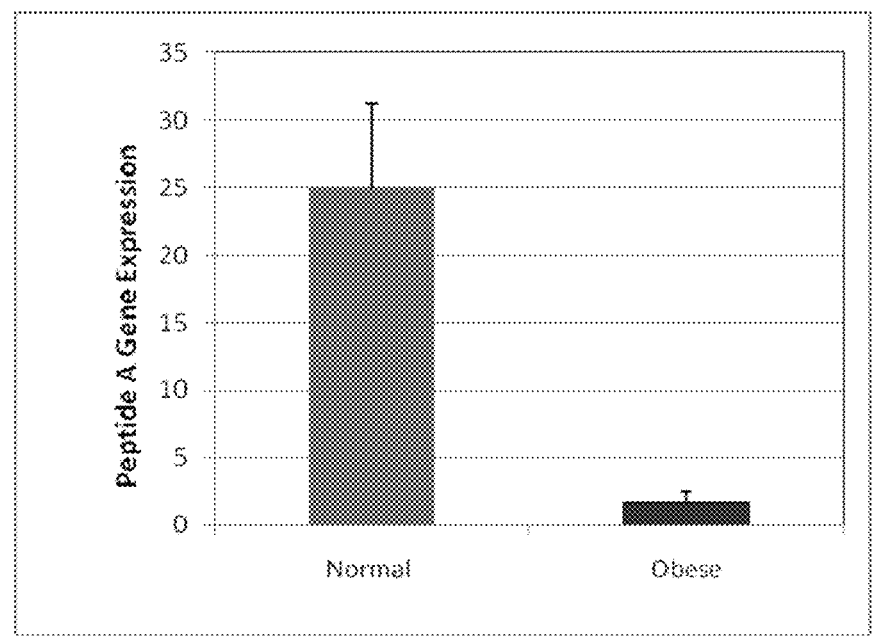
FIG. 9 is a bar graph showing that Spexin is down-regulated 14.8 fold in obese fat vs normal fat. Spexin is referred to as "Peptide A."

Using whole genome microarray analysis of human fat samples from two different depots, gene expression levels between obese vs. normal weight patients were compared (FIG. 1). Several thousand genes that are significantly differentially expressed between the two groups were identified (p<0.05, with no correction for multiple testing). Of all these, the gene with the greatest under expression (14.9 fold-change) in obese fat was Spexin (nor=24.95 vs obese=1.68; p=0.00292; "Petide A" in FIG. 9), a recently identified secreted peptide hormone that induces stomach contractions in a gut explant assay.

Since Spexin is significantly under-expressed by both omental and subcutaneous fat in obese patients, and it has biological activity in the gut, without being bound by theory, it is a factor expressed by normal fat tissues to indicate satiety. Without being bound by theory, the almost complete lack of Spexin expression in obese fat can contribute to the loss of a feedback loop which normally inhibits food intake and energy/lipid storage, leading to obesity.

Without being bound by theory, Spexin is expressed by adipocytes under normal conditions, to indicate a satiated, or energy saturated state. Therefore, under normal conditions, this signaling would have a dampening effect on energy seeking behavior.

Materials and Methods

Patients. The study population consisted of 11 patients undergoing clinically indicated abdominal laparoscopic surgical procedures, who consented to removal of an omental fat sample during surgery for studies of LCFA transport and a venous blood sample for the measurement of plasma levels of insulin and Leptin. Seven of the patients (all female) were obese, and were undergoing bariatric surgical procedures related to their obesity. The other four patients (all female) were non-obese, and were undergoing a variety of other clinically indicated laparoscopic procedures.

Gene Expression Studies

Tissue collection: Fat samples were collected at the time of bariatric surgery. One to two grams of tissue were placed in RNAlater at −80° C. for long-term storage.

Isolation of total RNA: The fat samples were thawed, then homogenized in 5 mls of TRIzol (Invitrogen). After standard phase separation and RNA isolation, the pellet was resuspended in water, RLT lysis buffer, and ethanol for RNA clean-up and on-column DNase treatment (Qiagen). Eluted RNA consistently had A260/A280 ratios >2.0. The integrity of the total RNA was verified by the presence of robust 18S and 28S peaks in the BioAnalyzer electropherogram.

Microarray target labeling and hybridization: Biotin-labeled cRNA were generated by established procedures. In brief, 2 µg of total RNA were used for synthesizing ds cDNA. This was incubated with biotin labeled 11-UTP in an in-vitro transcription reaction. cRNA was purified by RNeasy columns (Qiagen), and quantified by UV spectrophotometry at 260 nm. The size distribution of the biotin-labeled cRNA was verified on a Bioanalyzer (Agilent). 10 µg of fragmented cRNA was hybridized overnight on CodeLink Human 10K microarrays. Hybridized cRNAs were detected by Streptavidin-Cy 5 flur (GE Healthcare).

Data analysis: Spot detection was performed with the GenePix Series B scanner (Axon Instruments) and spot quantitation was performed using CodeLink™ Expression Analysis v5.0. Key quantitation parameters are described briefly here. Local background subtraction is carried out on the individual spot intensities, followed by a scaling of each array individually based on the overall array intensity. After median-normalization, individual data sets were uploaded into the GeneSifter microarray data analysis suite for further analysis.

Results

Identification of Ch12; or39 (Spexin) as significantly under-expressed in Obese fat. The Tenomodulin data point is identified to validate the data set, as this gene was recently reported to be over-expressed in obese fat samples (FIG. 1; Tolppanen, 2007; Saki, 2009). Another biomarker is chitinase, which indicates macrophage activation, reflecting an inflammatory state that is well-known in obesity (FIG. 1). Both Spexin and carbonic anhydrase III are significantly over-expressed in normal fat compared to obese fat (FIG. 1).

Ch12;orf39 is a newly identified peptide with GI activity (Mirabeau, 2007; Rucinski, 2010), and a potential satiety factor that is under-expressed in obese fat (FIG. 1).

Table 1 below depicts mRNA expression data for Spexin.

TABLE 1

Spexin mRNA Expression Data, sample by sample

| Group | Condition | N | Mean | SEM | SEM/Mean |
|---|---|---|---|---|---|
| 1 | obese | 12 | 1.6869 | +/−0.4284 | 25.4% |
| 2 | normal | 8 | 24.9532 | +/−5.2260 | 20.9% |

By Target

| Group | Sample | Median Normalized Expression |
|---|---|---|
| Obese | Subcu | 2.1212 |
| Obese | Subcu | 5.5443 |
| Obese | Subcu | 1.8812 |
| Obese | Subcu | 1.2796 |
| Obese | Omental | 0.4901 |
| Obese | Subcu | 1.5738 |
| Obese | Omental | 0.2394 |
| Obese | Omental | 2.6547 |
| Obese | Omental | 2.6115 |
| Obese | Omental | 0.6285 |
| Obese | Omental | 0.3092 |
| Obese | Omental | 0.9090 |
| normal | Subcu-1- | 22.1529 |
| normal | Subcu-2- | 45.3350 |
| normal | Subcu-3- | 16.7751 |
| normal | Subcu-4- | 29.0327 |
| normal | Omental-1- | 19.6793 |
| normal | Omental-2- | 8.5981 |
| normal | Omental-3- | 10.3961 |
| normal | Omental-4- | 47.6567 |

Figure 2:
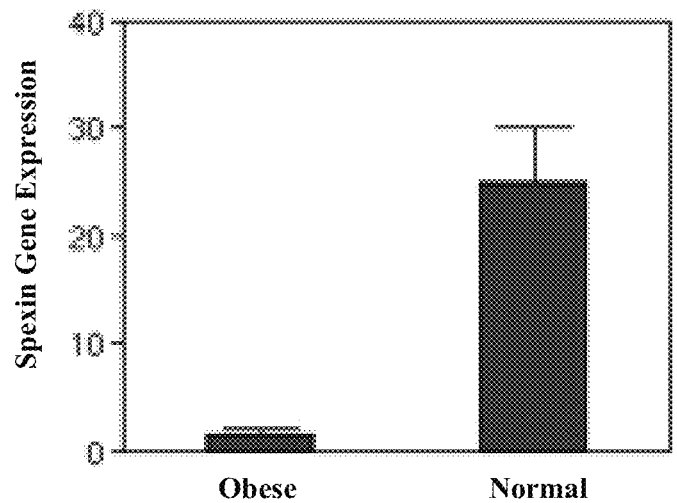
FIG. 2 is a graph of Spexin (Ch12, orf39) gene expression showing that it is down-regulated 14.8 fold in obese fat vs normal fat. Data represent mean plus SEM.

Of all the genes that are under-expressed in obese fat, Spexin demonstrates the largest fold-change between obese (1.687) and normal samples (24.95) (p<0.00292) (FIG. 2, Table 2).

TABLE 2

Spexin mRNA Expression Data, sample by sample (median normalized values for each sample sorted by group [obeses vs normal]). Statistical analysis by two-tailed t-Test, assuming unequal variance in the 2 sample sets (p = 0.00292).

| Obese | Normal |
|---|---|
| 2.1212 | 22.1529 |
| 5.5443 | 45.335 |
| 1.8812 | 16.7751 |
| 1.2796 | 29.0327 |
| 0.4901 | 19.6793 |
| 1.5738 | 8.5981 |
| 0.2394 | 10.3961 |

TABLE 2-continued

Spexin mRNA Expression Data, sample by sample (median normalized values for each sample sorted by group [obeses vs normal]). Statistical analysis by two-tailed t-Test, assuming unequal variance in the 2 sample sets (p = 0.00292).

| Obese | Normal |
|---|---|
| 2.6547 | 47.6567 |
| 2.6115 | |
| 0.6285 | |
| 0.3092 | |
| 0.909 | |
| 1.686875 | 24.95324 |

Figure 3:
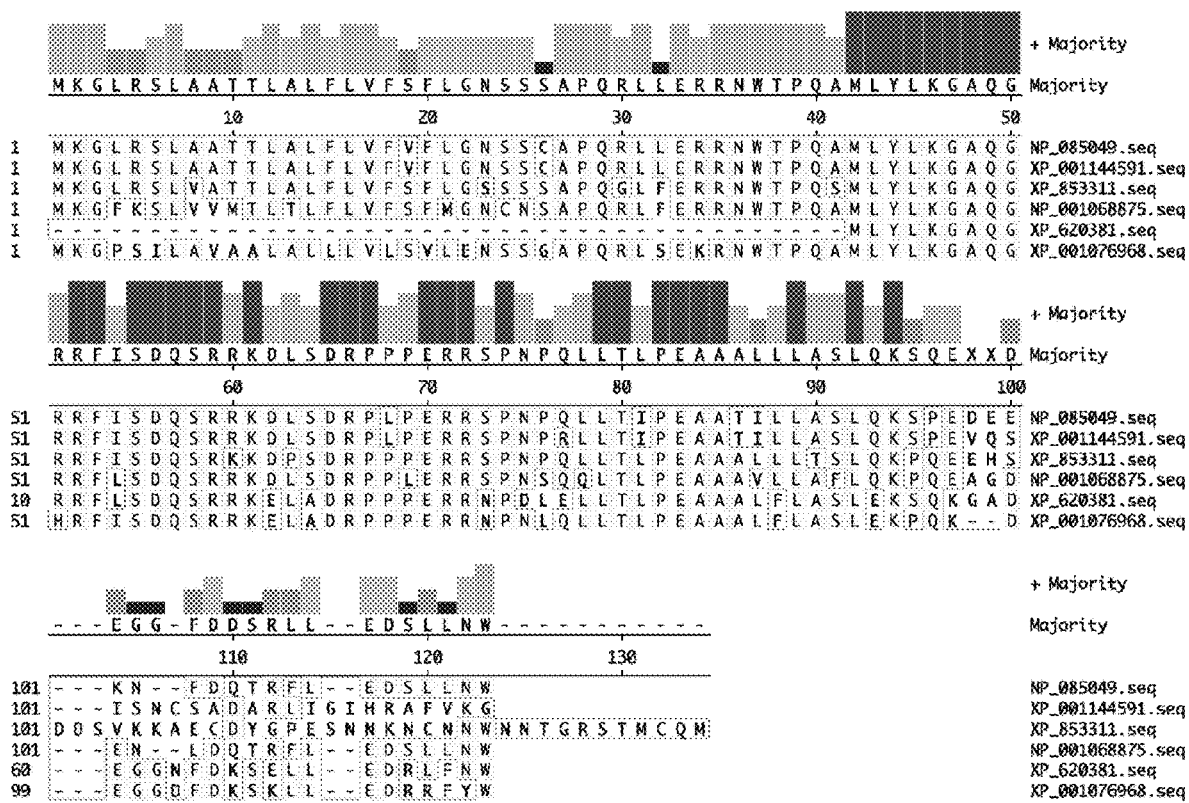
FIG. 3 is a multiple alignment of Spexin homologues from various species. Genebank was queried for human Spexin (NP_085049; SEQ ID NO: 26) and related homologues [chimpanzee (XP001144591; SEQ ID NO: 27), canine (XP_853311; SEQ ID NO: 28), bovine (NP_001068875; SEQ ID NO: 29), mouse (XP_620381; SEQ ID NO: 30), and rat (XP_001076968; SEQ ID NO: 31)]. The histogram on top of each panel indicates the degree of identity of the collection to the majority sequence (SEQ ID NO: 33) at each residue position (taller bars=greater identity). The yellow shading within the alignment indicates the amino acid residues that match the majority sequence at each position. Amino acid sequences were aligned using the Clustal W function of MegAlign (DNAstar). Sequence alignment parameters were; gap penalty (10), gap length penalty (0.20), delay divergent sequences (30%), and DNA transition weight (0.50).

Spexin is a newly identified peptide with GI activity. Mirabeau et al. (2007) was the first report describing Spexin, and they used Markov modeling analysis based on features common to peptide hormones, to find new ones in human proteome sequences. One of the hormones they identified was spexin, which demonstrated contractile activity in a rat stomach explant assay, indicating a biological activity. Spexin is secreted. Wan et al. (2010) described brefeldin A (BFA) sensitive secretion of Spexin from transfected cells, indicating a golgi dependent mechanism, and that it plays a role in the biological function of the placenta. Spexin is conserved among various species as indicated in the multiple sequence alignment of Spexin homologoues shown in FIG. 3.

REFERENCES

1: Mirabeau O, Perlas E, Severini C, Audero E, Gascuel O, Possenti R, Birney E, Rosenthal N, Gross C. Identification of novel peptide hormones in the human proteome by hidden Markov model screening. Genome Res. 2007 March; 17(3):320-7. Epub 2007 Feb. 6.
2: Rucinski M, Porzionato A, Ziolkowska A, Szyszka M, Macchi V, De Caro R, Malendowicz L K. Expression of the spexin gene in the rat adrenal gland and evidences indicating that spexin inhibits adrenocortical cell proliferation. Peptides. 2010 Jan. 4.
3: Saiki A, Olsson M, Jernås M, Gummesson A, McTernan P G, Andersson J, Jacobson P, Sjöholm K, Olsson B, Yamamura S, Walley A, Froguel P, Carlsson B, Sjöström L, Svensson P A, Carlsson L M. Tenomodulin is highly expressed in adipose tissue, increased in obesity, and down-regulated during diet-induced weight loss. J Clin Endocrinol Metab. 2009 October; 94(10): 3987-94.
4: Tolppanen A M, Pulkkinen L, Kolehmainen M, Schwab U, Lindstrom J, Tuomilehto J, Uusitupa M; Finnish Diabetes Prevention Study Group. Tenomodulin is associated with obesity and diabetes risk: the Finnish diabetes prevention study. Obesity (Silver Spring). 2007 May; 15(5): 1082-8.

Example 2—Spexin Expression in Obese and Normal Serum Samples

Example 1 discusses the significant under-expression of Spexin in omental and sub-cutaneous fat samples from obese patients. Therefore, it was decided to assay Spexin in serum samples from obese and normal weight patients, to see if the differences in obese fat gene expression resulted in significant differences in circulating Spexin levels. Leptin levels were also measured since Leptin is known to be a circulating adipokine that is elevated in the obese state. Without being bound by theory, circulating Spexin and Leptin can be "antagonistic" hormones/adipokines that are involved in the regulation of satiety, food intake, and body weight.

Serum Samples: Serum samples from 7 obese and 7 normal weight human female patients were assayed in these initial studies.

Spexin Assay: Circulating spexin levels in serum were assayed using the Spexin/NPQ (human, mouse, bovine) EIA kit from Phoenix Pharmaceuticals, Inc, Catalog #EK-023-81, Lot #601716. This kit measures what is believed to be the processed, bio-active peptide:

(SEQ ID NO: 3)
Asn-Trp-Thr-Pro-Gln-Ala-Met-Leu-Tyr-Leu-Lys-Gly-
Ala-Gln-NH2

The nature (primary sequence and structure) of circulating spexin in human serum has not been confirmed, nor has it been reported in any literature to date. The assay used has been designed to detect the peptide SEQ ID NO: 3.

Figure 4:
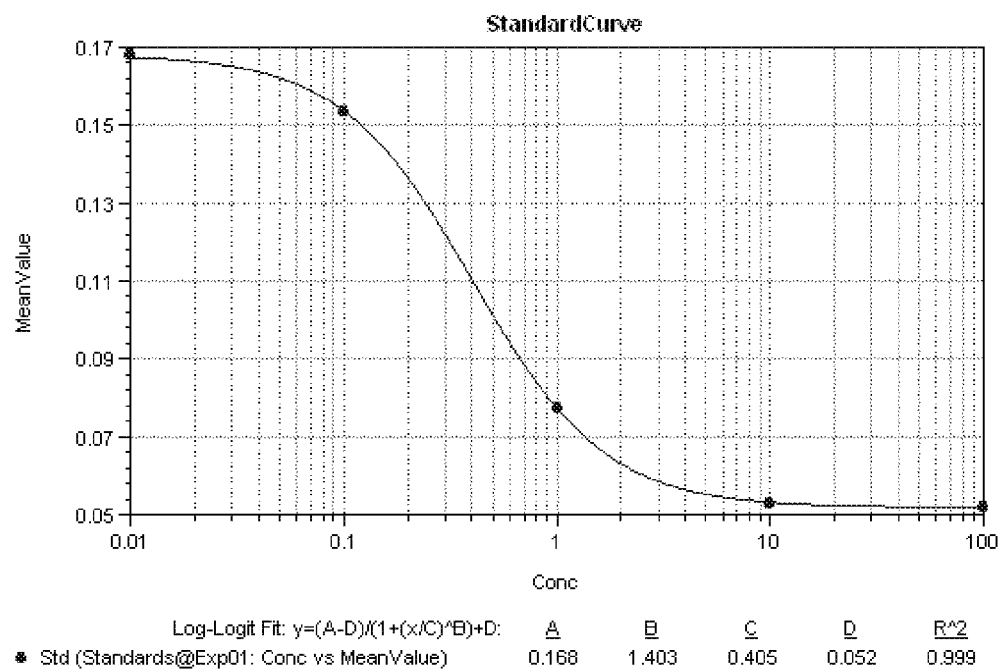
FIG. 4 shows a Spexin enzyme immunoassay (EIA) standard curve. A dilution series of known Spexin standards is plotted against their corresponding OD values to generate a standard curve for accurate quantitation.

The range of detection of circulating spexin is 0-100 ng/mL. Since this EIA is a competition assay, the measured optical density (OD) at 450 nm is inversely proportional to the amount of free antigen in the sample (see FIG. 4).

Figure 5:
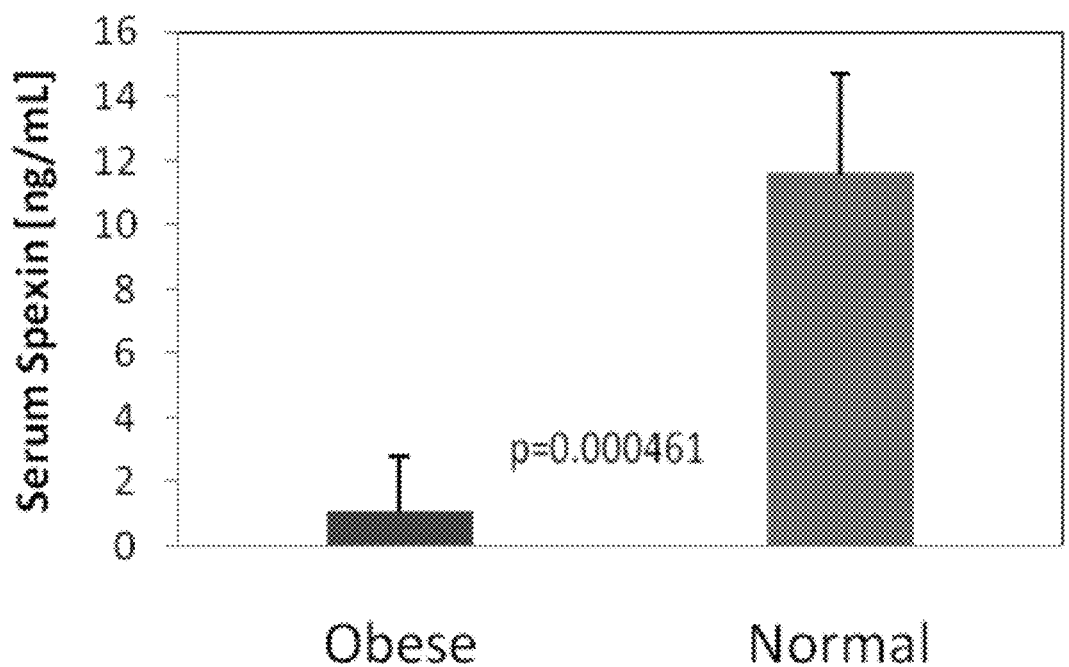
FIG. 5 is a bar graph showing that serum Spexin concentrations are lower in obese patients. Serum Spexin levels were assayed by antigen competition EIA in human serum samples from obese and normal weight individuals; (obese; n=7; 1.11+/−1.67) vs (normal; n=7; 11.60+/−3.20), (p<0.000461, by T test, 2 tailed with equal variance). Data represent means+/−St Devs in ng/mL.

With the discovery of significant under-expression of Spexin in omental and sub-cutaneous fat samples from obese patients (see FIG. 5), Spexin concentrations were assayed in serum samples from obese and normal weight patients to see if the reduced gene expression in obese fat resulted in significant differences in circulating Spexin levels. Circulating Spexin is approximately $\frac{1}{10}$th lower in concentration in obese serum, which is in reasonable agreement with the 15-fold difference in Spexin gene expression reported above (FIG. 5).

Figure 6:
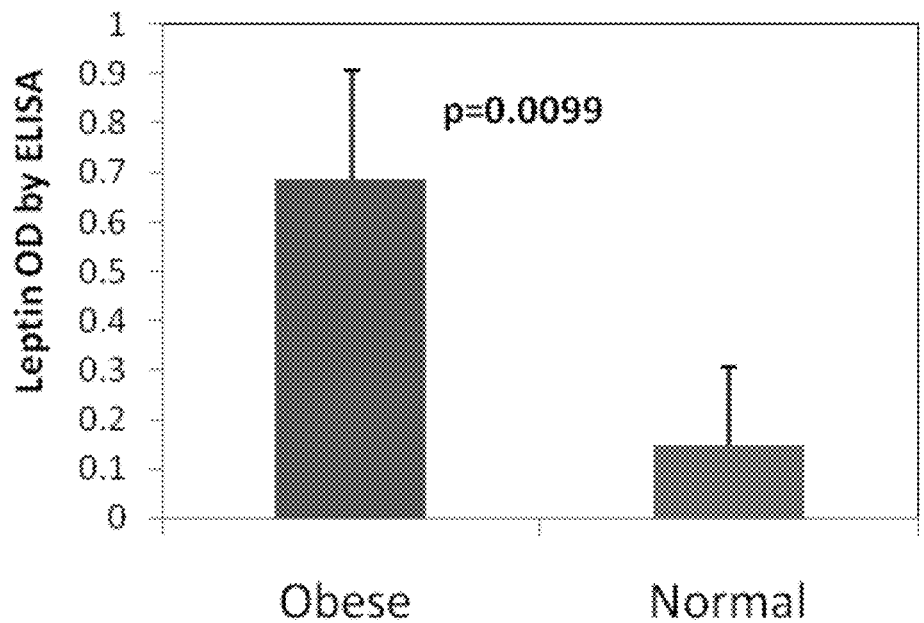
FIG. 6 is a bar graph showing that serum Leptin levels are significantly higher in obese patients. Serum Leptin levels were measured by antigen capture ELISA; obese n=7 (0.69+/−0.22) vs normals n=6 (0.15+/−0.15), (p=0.0099, by T test, 2 tailed with equal variance). Data represent mean ODs+/−St Dev, respectively.
Figure 10:
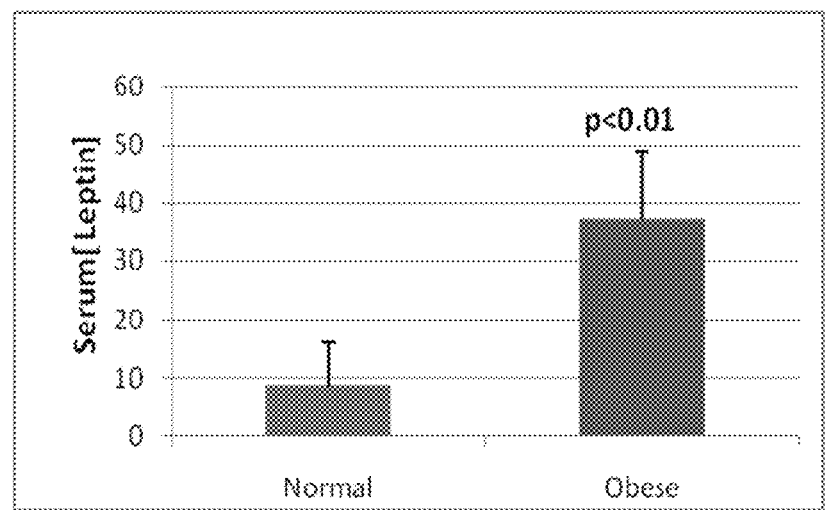
FIG. 10 is a bar graph of serum Leptin levels. Serum Leptin levels were measured by immunoassay in the same normal (8.53+/−7.55) and obese patients (37.42+/−11.56) (p<0.01, by t test, 2 tailed). Data represent mean+/−St Dev.
Figure 11:
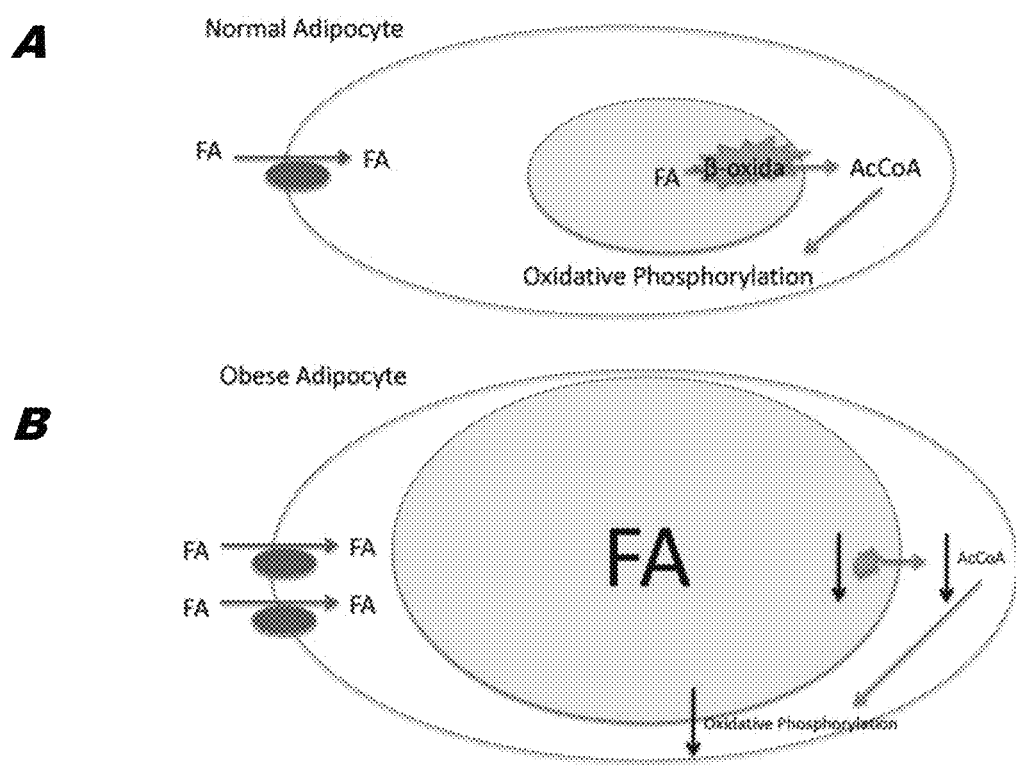
FIG. 11 depicts a schematic of a model of Long Chain Fatty Acid (LCFA) accumulation in Obese Adipocytes. In the adipocytes of normal weight subjects (FIG. 11A), LCFA uptake (including facilitated transport) and degradation (including β-oxidation in adipocytes) are in balance, with no net gain or loss of LCFA. As a result, over time, the relative amount of LCFAs in each cell is constant. In adipocytes from obese subjects (FIG. 11B), the combination of increased LCFAs by specific transporters (as demonstrated in uptake studies discussed herein), and reduced β-oxidation and fatty acid metabolism (indicated by the expression studies) leads to an accumulation of LCFAs in these adipocytes over time, resulting in enlarged adipocytes and obesity.

Leptin is known to be elevated in the obese state. Without being bound by theory, circulating Spexin and Leptin can be "antagonistic" or counter-balancing hormones/adipokines that are involved in the regulation of satiety, food intake, and body weight. The magnitude of the difference reported in FIG. 6 (0.69/0.15=4.6-fold increase in circulating Leptin in obese serum) is equivalent to that reported by Considine, et al. (1996), where the magnitude of increase in circulating Leptin in obese patients was 4.17 fold using a newly developed RIA. Considine, et al. assayed circulating human Leptin in obese (n=139 men and women) vs normal weight men and women (n=136). The mean (+/−SD) Leptin levels were 31.3+/−24.1 ng/mL in obese patients, and 7.5+/−9.3 ng/mL in normal weight patients. Circulating Leptin levels are significantly higher in obese patients (FIG. 10).

Figure 7:
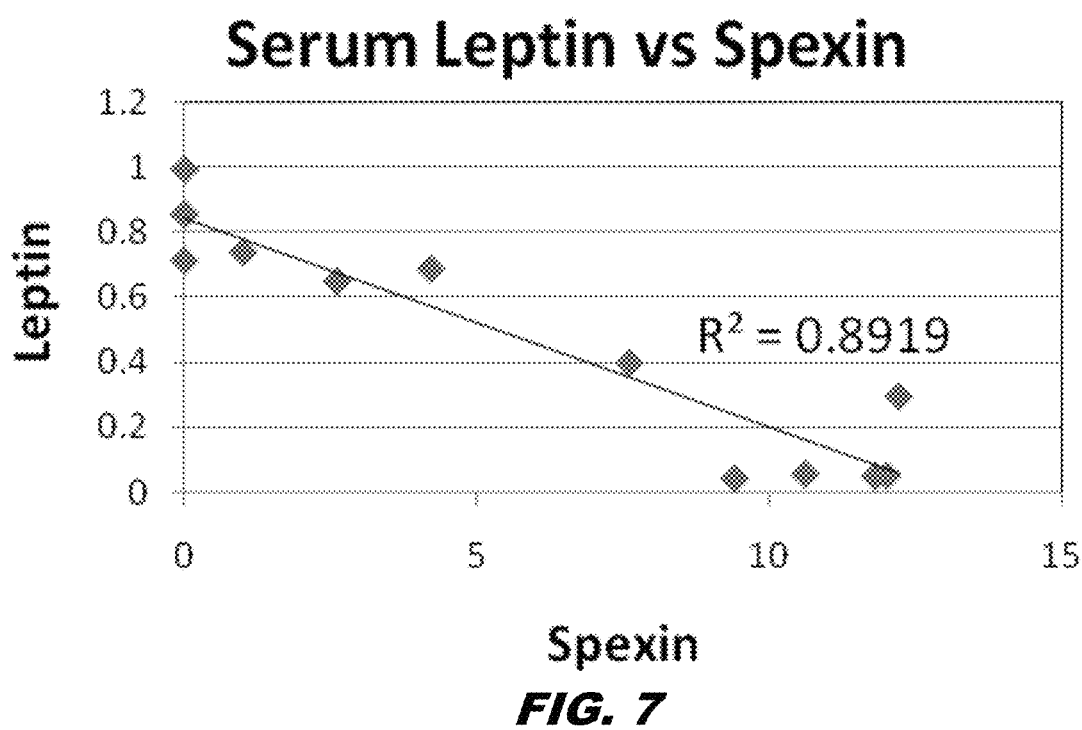
FIG. 7 is a graph showing the correlation between Leptin and Spexin levels in serum from obese (n=7) and normal weight patients (n=6). Leptin ODs (ordinate) were plotted against Spexin [ng/mL] (abscissa) for each patient sample. The negative correlation (−r=0.9444) observed between the two circulating peptides is quite strong, with an $R^2$ of 0.8919.

The strong negative correlation (r=−0.9444) between Leptin and Spexin in the serum of obese patients and normal weight controls supports the idea that these two peptides play antagonistic roles in the normal regulation of hunger, satiety, body weight and adiposity (FIG. 7). Without being bound by theory, each hormone can serve as part of a negative feedback loop, where a rise in one leads to a lowering of the other (and vice versa). In the absence of circulating Spexin, Leptin is over-expressed in the fat, and is over-produced in the serum. Therefore, when Spexin is under expressed in fat, leading to a significant decrease of circulating Spexin, Leptin is over-expressed in the fat of obese patients, resulting in pathophysiologic levels of Leptin in the serum.

Figure 8:
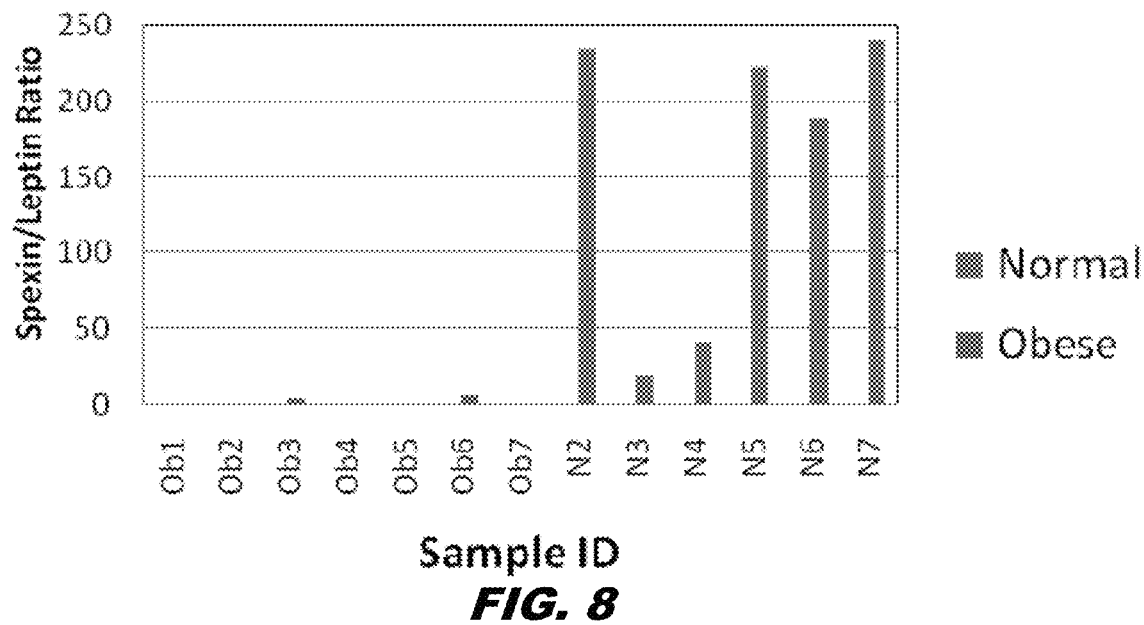
FIG. 8 is a bar graph showing that serum Spexin vs Leptin ratios distinguish Obese vs Normal weight patients. The ratios of Spexin to Leptin are plotted for each patient. Obese (n=7, red) ratios range from 0 to 6.1, and in normal patients (n=6, blue) the ratios range from 19 to 240, with most more than 150.

Calculating the ratios of negatively correlated values can magnify the differences in gene expression between groups, and serve as sensitive and reliable diagnostic markers (Gordon et al, 2002, 2003) to distinguish groups. An extension of this idea is presented in FIG. 8, where ratios of protein expression confirm the classifications based on BMIs. While this does not seem to add any new information at this time, it can be possible in the future, once more samples are analyzed, to distinguish sub-classes (metabolic syndrome, pre-diabetic, morbidly obese, hyper-lipidemic, etc) of patients in each group with this algorithm.

REFERENCES

1: Considine R V, Sinha M K, Heiman M L, Kriauciunas A, Stephens T W, Nyce M R, Ohannesian J P, Marco C C, McKee L J, Bauer T L, et al. Serum immunoreactive-Leptin concentrations in normal-weight and obese humans. N Engl J Med. 1996 Feb. 1; 334(5):292-5.
2: Gordon G J, Jensen R V, Hsiao L L, Gullans S R, Blumenstock J E, Richards W G, Jaklitsch M T, Sugarbaker D J, Bueno R. Using gene expression ratios to predict outcome among patients with mesothelioma. J Natl Cancer Inst. 2003 Apr. 16; 95(8):598-605. PubMed PMID: 12697852.
3: Gordon G J, Jensen R V, Hsiao L L, Gullans S R, Blumenstock J E, Ramaswamy S, Richards W G, Sugarbaker D J, Bueno R. Translation of microarray data into clinically relevant cancer diagnostic tests using gene expression ratios in lung cancer and mesothelioma. Cancer Res. 2002 Sep. 1; 62(17):4963-7.

Example 3—Spexin Infusion to Determine Role of Spexin in Satiety

Initial dose-determining experiments. Both normal weight and obese high-fat diet mice will be tested for circulating levels of Leptin, insulin, and Spexin. The Spexin level in human serum is approximately 10 ng/ml in normal subjects (e.g., non-obese subjects), thus the following four doses will be tested in the initial studies: about 3 ng, about 10 ng, about 30 ng, about 100 ng, about 1 μg, about 10 μg, and about 100 μg.

Pharmaceutical grade Spexin (a 14 amino acid peptide normally circulating in mice and humans) has been synthesized by conventional solid-state chemistry, and purified to >95% identity by Phoenix Pharmaceuticals (Burlingame, Calif.). This agent will be solubilized in 1× sterile saline (pH 7.4) at four different concentrations, so that doses of 1.5 μg/kg/QD, 5 μg/kg//QD, 15 μg/kg//QD, or 50 μg/kg/QD can be administered to 5 mice in each dose group. Final total doses of 3 μg/kg/day, 10 μg/kg/day, 30 μg/kg/day, 100 μg/kg/day, or 250 μg/kg/day will be delivered in volumes of 0.2 ms/dose/day via IP injections. For example, to deliver 10 μg total per day, two daily injections of 5 μg each will be administered IP (stock concentrations of Spexin will be 25 μg/ml). Alternatively, to deliver 10 μg per day, a daily injection of 10 μg can also be administered IP (stock concentrations of Spexin will be 50 μg/ml). In a further example, to deliver 50 μg per day, a daily injection of 50 μg can also be administered IP (stock concentrations of Spexin will be 2500 μg/ml).

Alternatively, five doses of Spexin (3 ng, 10 ng, 30 ng, 100 ng, and 500 ng) will be administered for 30 days via osmotic mini-pump infusions (see Fan et al, J Nutr. 2003 September; 133(9):2707-15). The doses will be selected to range around those calculated to mimic Spexin concentrations seen in normal weight animals. Blood samples will be drawn weekly via tail vein to confirm circulating levels of spexin, Leptin and insulin. Body weights, diet, and water consumption will also be monitored and recorded daily.

Administering Effective Dose of Spexin in Various Murine Models of Obesity.

Once an effective and safe dose of Spexin is identified, this will be used to test the effects of Spexin in a number of well-known murine models of obesity.

Mouse Strains to be used include: (1) C57BL/6J background as controls; (2) DIO (Diet Induced Obesity) mice, also known as High Fat Diet Fed Mice; (3) ob/ob; (4) ob/ob treated with Leptin as a positive control; (5) db/db (diabetic mouse); (5) Fat; and (6) Tubby.

Blood samples will be drawn weekly to confirm circulating levels of Spexin, Leptin and insulin. Body weights, diet, and water consumption will be monitored and recorded daily.

Spexin dose adjustments (if necessary for a specific strain or model) will be started in new sets of animals.

At the end of the experiment, heart, liver and epidydimal fat pads will be harvested for fatty acid uptake, qRT-PCR and western blot analysis of fatty acid transporters and key enzymes of the oxidative phosphorylation pathway.

Example 4—Leptin Expression is Selectively Upregulated in Obese Omental Fat

Introduction: Leptin is an adipokine that is expressed by various fat depots. While earlier studies reported that Leptin expression varies between omental, subcutaneous and mesenteric tissues, there is little data comparing expression of Leptin at different tissue depots between obese and normal patients.

Methods: Surgical samples were collected and stored at −80° C. in RNAlater. Total RNAs from omental (7 obese, 4 controls) and subcutaneous (5 obese, 4 controls) fat depots were collected from the same patients. cRNAs were generated using standard protocols, and hybridized overnight to Codelink Human Whole Genome microarrays. Median normalized expression data (arbitrary expression units) were analyzed by the GeneSifter Data package. Results are presented as mean+/−SEM.

Results: Total Leptin expression was not significantly higher in obese vs normal fat, (90.7+/−15.1 vs. 77.7+/−24.9). There is a large difference in Leptin expression between normal subcutaneous and omental fat (130.5+/−30.8 vs. 24.9+/−8.6), while in obese samples, the difference in Leptin expression between the depots was less pronounced (118.4+/−30.0 vs 71.0+/−11.6; sub cu vs. omental). Leptin expression does not change between obese and normals at the subcutaneous depot (130.5+/−30.8 vs 118.4+/−30.0). However, a dramatic increase in Leptin expression was seen in the obese vs normal omental fat samples (71.0+/−11.6 vs 24.9+/−8.6).

Conclusions: The obese state alters Leptin expression in the omental depot, while expression is unchanged in subcutaneous fat from the same patients.

Example 5—Adipocyte Accumulation of Long Chain Fatty Acids in Obesity is Multifactorial, Resulting from Increased Fatty Acid Uptake and Decreased Activity of Genes Involved in Fat Utilization Overview. The obesity epidemic causes significant morbidity and mortality. Knowledge of cellular function and gene expression in obese adipose tissue will yield insights into obesity pathogenesis and indicate therapeutic targets. This Example is directed to studying the processes determining fat accumulation in adipose tissue from obese patients.

Briefly, omental fat was collected from two cohorts of obese bariatric surgery patients and sex matched normal-weight donors. Isolated adipocytes were compared for cell size, volume and long chain fatty acid (LCFA) uptake. Omental fat RNAs were screened by 10K microarray (cohort 1:3 obese, 3 normal) or Whole Genome microarray (cohort 2:7 obese, 4 normal). Statistical differences in gene and pathway expression were identified in cohort 1 using GeneSifter Software (Geospiza) with key results confirmed in Cohort 2 samples by microarray, qRT-PCR and pathway analysis.

Obese omental adipocytes had increased surface area, volume, and $V_{max}$ for saturable LCFA uptake. Dodecenoyl-coenzyme A delta isomerase (DCI), central to LCFA metabolism, was approximately 1.6 fold under-expressed in obese fat in cohorts 1 and 2. Additionally, Kyoto Encyclopedia of Genes and Genomics (KEGG) pathway analysis identified the Oxidative Phosphorylation and Fatty Acid Metabolism pathways as having coordinate, non-random down-regulation of gene expression in both cohorts.

In obese omental fat, saturable adipocyte LCFA uptake was greater than in controls, and expression of key genes involved in lipolysis and β-oxidation and metabolism of fatty acids was reduced. Thus, both increased uptake and reduced metabolism of LCFAs contribute to the accumulation of LCFAs in obese adipocytes.

Introduction. Studies (A1-15) have shown that cellular LCFA uptake occurs by two distinct processes, of which diffusion is the minor component. At the LCFA concentrations typically found between meals, 80-95% of total cellular LCFA uptake is via a saturable, regulatable, facilitated transport process (A7, A8). Studies in animals and patients indicate that regulation of adipocyte LCFA uptake is an important control point for body adiposity (A16-21). However, as in the liver (A22-24), many additional processes also contribute to LCFA and TG accumulation. Therefore, to understand the totality of the processes leading to obesity, it is important to define the global pattern of gene expression in adipose tissue. Published data indicate that at least 50 distinct genes are potentially involved in the establishment and maintenance of obesity (A22).

This Example discusses multiple processes for determining fat accumulation in adipose tissue from obese patients. Omental adipose tissue was collected from patients undergoing bariatric surgery for the treatment of morbid obesity, and were analyzed as part of an initial, small cohort of samples. The study yielded a pathophysiologic finding and a valuable illustration of the translational research that can be performed via the combined efforts of bariatric surgeons and basic scientists. Both technical and biological validation of the original results were achieved in an ongoing study of a second, larger cohort of patient samples. Also, the observed changes in key genes from the first cohort were validated by using both an alternative microarray platform and qRT-PCR on samples from the second cohort.

Materials and Methods

Patients

The initial study population (Cohort 1) consisted of 6 patients undergoing clinically indicated abdominal laparoscopic surgical procedures who consented to removal of an omental fat sample during surgery for studies of LCFA transport. Three of the patients (two males, one female) were obese, and were undergoing bariatric surgical procedures related to their obesity. Despite obesity and the fact that none was on medications that influence glucose metabolism, none of the subjects had elevated fasting blood glucose concentrations. The other three patients (two males, one female) were non-obese, and were undergoing various other clinically indicated laparoscopic procedures. None was diabetic, had a significant chronic inflammatory disease or malignancy, or was on medications that could influence glucose metabolism, and—again—none had an elevated fasting blood glucose. Cohort 2 consisted of 7 obese female bariatric surgery patients and 4 non-obese female controls, all undergoing laparoscopic surgical procedures.

Physiologic Studies

Materials: 9,10-[$^3$H] oleic acid (OA) was purchased from NEN Life Science Products, type I collagenase for adipocyte isolation from Sigma (St. Louis, Mo.), fatty acid free bovine serum albumin (BSA) from Boehringer Mannheim (Indianapolis, Ind.), and human-insulin-specific and human Leptin RIA kits from Linco Research, Inc. (St. Charles, Mo.).

Isolation of adipocytes: Suspensions of human adipocytes were prepared by collagenase digestion of omental fat samples (A2, A9, A16). Suspensions were maintained at room temperature in Dulbecco's modified Eagle's medium (DMEM) for up to 3 hours until warmed to 37° C. for use (A16), and met established viability criteria (A2, A9, A16). Isolated adipocytes were sized by direct light microscopy at 100×, using an eyepiece reticle with which cell diameters were measured in arbitrary units (1 U=9.6μ). The corresponding mean cell surface areas (SA) and cell volumes (Vol) were calculated as described (A25).

LCFA uptake studies: The initial rate of [$^3$H]-OA uptake by omental adipocytes was determined by rapid filtration as described (A1, A2, A16). Briefly, cell suspensions with known cell counts, in 100 μl of DMEM, were added to 240 μl of DMEM containing 500 μM BSA and varying [$^3$H]-OA concentrations, and incubated for 0-30 s at 37° C. At four specified time points, uptake was stopped (A1, A2), the cells were filtered and washed on the filters, and the filters with the cells were counted by liquid scintillation spectrometry (A2, A16). Adipocyte [$^3$H]-OA uptake is linear over the initial 30 sec of incubation (A2, A16). The slopes of the cumulative uptake versus time curves, representing initial uptake velocity ($V_o$), were calculated from four samples obtained in triplicate over this portion of the curve by linear regression.

Computations and Fitting of Kinetic Data: The unbound oleate concentration ([$OA_u$]) in each test solution was calculated from the OA:BSA molar ratio (v) (A26), using the LCFA:BSA binding constants of Spector et al (A27). The rationale for the use of these particular binding constants rather than several alternatives (A28-30) has been reported in detail previously (A8). Based on prior analyses (e.g. A5-8), measurements of initial oleate uptake velocity at values of v from 0.25-2.0 were fitted to the sum of a saturable and a non-saturable function of the corresponding [$OA_u$], according to the equation [A1]:

$$UT([OA_u]) = (V_{max} \cdot [OA_u])/(K_m + [OA_u]) + k \cdot [OA_u],$$

in which $UT([OA_u])$ is the experimental measurement of uptake, in pmol/sec/50,000 cells, at the stipulated [$OA_u$]; $V_{max}$ and $K_m$ are the maximal uptake velocity of the saturable oleic acid uptake component and the value of [$OA_u$] at one-half the maximal uptake velocity; and k is the rate constant for non-saturable uptake (A2, A7, A8, A19, A21). Data fitting was via the SAAM II version of the Simulation, Analysis and Modeling (SAAM) program (A31), modified for execution on a lap-top PC computer (A32). Prior studies documented that, under the specific conditions employed in the current studies, $V_o$ and derived parameters such as $V_{max}$ are measures of trans-membrane transport, largely unmodified by pre-membrane phenomena such as rate-limiting dissociation from BSA and the effects of the peri-cellular unstirred water layer on substrate availability at the cell surface (A33), or of intracellular binding or metabolism (A1). Studies in which an increase in $V_{max}$ was preceded an increase in adipocyte size early in the development of obesity (A19) and a decrease in $V_{max}$ preceded a reduction in adipocyte size during Leptin-induced weight loss (A17) established that changes in $V_{max}$ did not simply reflect changes in cell volume.

Statistical considerations: Values for physiologic variables are reported as mean±SD, calculated according to standard methods of descriptive statistics (A34). The significance of differences between groups was assessed with Student's 2-tailed t-test, with $\alpha \leq 0.05$ being considered significant.

Gene Expression Studies

Tissue collection: Omental fat samples were collected at the time of laparoscopic surgery. Samples were divided, and 1-2 grams of tissue from each biopsy were placed in RNAlater (Invitrogen, Carslbad, Calif.) at −80° C. for long-term storage.

Isolation of total RNA: The fat samples were thawed, and then homogenized in 15 ml of TRIzol (Invitrogen). After standard phase separation and RNA isolation, the pellet was resuspended in water, RLT lysis buffer, and ethanol for RNA clean-up and on-column DNase treatment (Qiagen). Eluted RNA consistently had A260/A280 ratios >2.0. The integrity of the total RNA was verified by the presence of robust 18S and 28S peaks in BioAnalyzer electropherograms (Agilent).

Microarray target labeling and hybridization: Biotin-labeled cRNAs were generated by established procedures. In brief, 2 µg of total RNA were used for synthesizing ds cDNA. This was incubated with biotin labeled 11-UTP in an in-vitro transcription reaction. cRNA was purified by RNeasy columns (Qiagen), and quantified by UV spectrophotometry at 260 nm. The size distribution of the biotin-labeled cRNA was verified by capillary electrophoresis (Bioanalyzer, Agilent). 10 µg of fragmented cRNA was hybridized overnight on CodeLink Human 10K microarrays (Cohort 1) or Human Whole Genome microarrays (Cohort 2). Hybridized cRNAs were detected by Streptavidin-Cy5 fluor (GE Healthcare).

qRT-PCR validation: Expression of seven genes found to be under-expressed by microarray analysis in Cohort 2 was examined in the same samples by qRT-PCR. Individual gene PCR primers were designed using Primer 3 software (v.0.4.0) at (Table 3).

TABLE 3

Primer sequences for qRT-PCR studies.

| Gene | Primer | $T_m$ | Sequence (5'-3') | SEQ ID NO: | Product size (nt) |
|---|---|---|---|---|---|
| Control (housekeeping) genes | | | | | |
| BBS4 | Forward | 59.93 | atcccaaatcaaagcaccag | 4 | 157 |
| | Reverse | 59.97 | ggctttgtgaactgggatgt | 5 | |
| MTIF2 | Forward | 59.99 | tcagaaagcccgtgagaagt | 6 | 171 |
| | Reverse | 59.93 | atggcctcaacagaaccatc | 7 | |
| PGBD3 | Forward | 59.99 | ccacctgtctgggctacatt | 8 | 211 |
| | Reverse | 59.93 | gcctgatgtcccattgaact | 9 | |
| PAICS | Forward | 59.96 | ctggggagttcaggatgtgt | 10 | 183 |
| | Reverse | 59.96 | tcagcctgcttaaaggaaat | 11 | |
| Target genes | | | | | |
| DCI-SP1 | Forward | 59.82 | acaccctggagaacaccatc | 12 | 185 |
| | Reverse | 62.55 | ctgtcgagcatggtctggaat | 13 | |
| ECHD | Forward | 59.99 | cagcttctccccagactcac | 14 | 218 |
| | Reverse | 59.70 | atgttgggcaagctctgaat | 15 | |
| ADH1A | Forward | 60.13 | gtgccactgaattgatcaac | 16 | 195 |
| | Reverse | 60.17 | ggttttgggaatcaggaggt | 17 | |
| ATP5D | Forward | 59.85 | caaggcaaacttggagaagg | 18 | 175 |
| | Reverse | 60.06 | gggcagttcatccagaggt | 19 | |
| COX4I1 | Forward | 59.53 | ggcactgaaggagaaggaga | 20 | 204 |
| | Reverse | 60.02 | gggccgtacacatagtgctt | 21 | |
| CYC1 | Forward | 59.95 | ccagctaccatgtcccagat | 22 | 166 |
| | Reverse | 59.87 | tcaggactgaccacttgtgc | 23 | |
| NDUFS7 | Forward | 60.12 | agttctctgtggcccatgac | 24 | 197 |
| | Reverse | 59.17 | ggcatctggtcgtagacctt | 25 | |

Selection criteria included $T_m$s of approximately 60° C., and PCR product lengths between 150 and 250 bp. First strand cDNAs were synthesized from total RNA samples using the TaqMan Reverse Transcription Reagent kit (Applied Biosystems), with oligo dT as primers. PCRs were performed on the 7300 Real time PCR system (Applied Biosystems), with the SYBR® GREEN PCR Master Mix (Applied Biosystems) in a total volume of 50 µl containing 500 ng cDNA as detailed in the manufacturer's guidelines. PCR conditions were: cycle 1 at 50.0° C. for 2 mins, cycle 2 at 95.0° C. for 10 mins, followed by 40 cycles (two step; 95.0° C. for 0.15 mins, then 60.0° C. for 1.00 min.). Each PCR was performed in duplicate. BBS4, MIT1F, PGBD3 AND PAICS were selected as control genes based on their robust expression, with minimal differences between the normal and obese omental fat samples in the Cohort 1 analysis. The means of their expression levels were used to normalize the expression of target genes DCI-SP1, ECHD, ADH1A, ATP5D, COX4I1, CYC1 and NDUFS7 in all samples. The average fold change (AFC) was computed by using the average difference in the ΔCt between each test gene and the mean of the 4 control genes for each sample, i.e. AFC=2-(average$_{\Delta\Delta Ct}$).

Data analysis: Microarray spot detection was performed with the GenePix Series B scanner (Axon Instruments) and spot quantitation was performed using CodeLink™ Expression Analysis v4.1 (Cohort 1) or CodeLink™ Expression Analysis v5.0 (Cohort 2). Key quantitation parameters are described briefly below. Local background subtraction is carried out on the individual spot intensities, followed by a scaling of each array individually based on the overall array intensity. After median-normalization, the negative control threshold is calculated using a set of negative control probes as described (A35).

Gene ontology and KEGG pathway analysis: Median-normalized gene expression values were then imported into the GeneSifter gene expression analysis suite (Geospiza, Seattle, Wash.). Array data for significantly differently expressed genes were overlaid onto ontological pathways (A36) and KEGG pathways (A37) using GeneSifter software. The ontological and KEGG pathway analyses provide data on individual genes in the context of that gene's role in described biological/biochemical pathways. A pathway was considered significantly altered from the control gene expression profile if its z-score was less than −2 or greater than 2.

z-Scores were calculated in GeneSifter as:

$$z\text{-Score} = \frac{\left(r - n\frac{R}{N}\right)}{\sqrt{n\left(\frac{R}{N}\right)\left(1 - \frac{R}{N}\right)\left(1 - \frac{n-1}{N-1}\right)}}$$

where R=total number of genes meeting selection criteria, N=total number of genes measured, r=number of genes meeting selection criteria with the specified gene ontology (GO) term, and n=total number of genes measured with the specific GO term (38). z-Scores with an absolute value of ≥2.0 are considered to indicate significantly altered regulation of the pathway compared with controls. The meaning of the z score depends on the context of the reported score. When reported as a z up score, a positive z-score equal to or greater than 2 indicates that a significant number of genes in the list of differentially expressed genes are up-regulated in the experimental group in that particular pathway. Conversely, a negative z up score of −2 or less, is also significant, and indicates that fewer than expected genes are over-expressed in the pathway. For z down scores, the interpretation is as follows: a positive z down score indicates that more genes than expected are under-expressed, and a negative z down score indicates that fewer than expected genes are under-expressed in the pathway.

Results

Patients: The demographic and clinical characteristics of the patients are summarized in Table 4.

TABLE 4

Demographic and clinical characteristics of study patients

| Group | Sex | Age (years) | BMI (kg/m² BSA) | Insulin (ng/ml) | Leptin (ng/ml) | Glucose (mg/dL) | Cholesterol (mg/dL) | TG (mg/dL) |
|---|---|---|---|---|---|---|---|---|
| Cohort 1 | | | | | | | | |
| Obese 1 | 2 M, 1 F | 53.7 ± 7.8 | 42.7 ± 5.7* | 9.7 ± 1.5 | 22.0 ± 4.9** | 88.3 ± 7.5**** | 237 ± 38 | 213 ± 44 |
| Control 1 | 2 M, 1 F | 50.7 ± 12.6 | 23.7 ± 0.4 | 8.6 ± 3.8 | 2.2 ± 1.0 | 63.0 ± 5.8 | 176 ± 19 | 146 ± 17 |
| Cohort 2 | | | | | | | | |
| Obese 2 | 7 F | 51.6 ± 6.0* | 48.6 ± 2.6*** | ND | ND | 92.0 ± 3.1 | 196 ± 20 | 130 ± 23 |
| Control 2 | 4 F | 30.0 ± 6.0 | 22.1 ± 2.3 | ND | ND | 87.3 ± 10.3 | 161 ± 6 | 79 ± 24 |

*p < 0.05;
**p < 0.02;
***p < 0.001;
****0.1 > p > 0.05 compared with cohort controls
ND not done The initial study population (Cohort 1) consisted of three obese and three non-obese subjects, with two males and one female in each group. Cohort 2 consisted of 7 obese and 4 non-obese female patients. The average ages of the obese patients in both cohorts and control patients in Cohort 1 were similar. The non-obese patients in Cohort 2 were younger. Virtually by definition, the BMI was significantly greater in the obese patients than in the control patients in both Cohorts. Values for obese and non-obese subjects in the two cohorts were very similar. In additional studies in Cohort 1, the fasting plasma Leptin concentration was significantly higher in obese than in control subjects. Although mean fasting blood glucose, plasma insulin, and serum cholesterol and triglycerides were all higher in the obese patients than in the controls, only the difference in glucose levels between the obese and non-obese patients of Cohort 1 achieved statistical significance.

Adipocyte sizes: Adipocyte size measurements and the results of adipocyte LCFA uptake studies (Cohort 1 only) are presented in Table 5.

TABLE 5

Adipocyte measurements and fatty acid uptake kinetics.

| Group | Diameter (μm) | Surface area per cell (μm)² | Volume per cell (pL) | $V_{max}$ (pmol/s/50,000 cells) |
|---|---|---|---|---|
| Cohort 1 | | | | |
| Obese | 94.7 ± 6.8** | 32,717 ± 9,492**** | 486 ± 191 | 19.6 ± 4.7* |
| Control | 53.4 ± 4.4 | 9,953 ± 1,659 | 81 ± 18 | 4.8 ± 2.0 |
| Cohort 2 | | | | |
| Obese 2 | 101.6 ± 4.4*** | 32,799 ± 2,784*** | 568 ± 71*** | ND |
| Control 2 | 58.1 ± 5.8 | 10,910 ± 2,630 | 112 ± 42 | ND |

| Group | $K_m$ (nM) | k (ml/s/50,000 cells) | $v_{max}/SA \times 10^8$ (pmol/s/μ²) |
|---|---|---|---|
| Cohort 1 | | | |
| Obese | 149 ± 15 | 0.0105 ± 0.0055 | 1.20 ± 0.45 |
| Control | 142 ± 49 | 0.0068 ± 0.0018 | 0.96 ± 0.43 |
| Cohort 2 | | | |
| Obese 2 | ND | ND | ND |
| Control 2 | ND | ND | ND |

*$p < 0.05$;
**$p < 0.01$;
***$p < 0.001$;
****$0.1 > p > 0.05$ compared with cohort controls Adipocytes from obese patients were appreciably larger than those from non-obese controls in both Cohorts. Mean cell diameters were 1.7-1.8 times larger, surface areas 3.0-3.3 times larger, and cell volumes 5.1-6.0 times larger in obese than in non-obese patients of both Cohorts.

Figure 13:
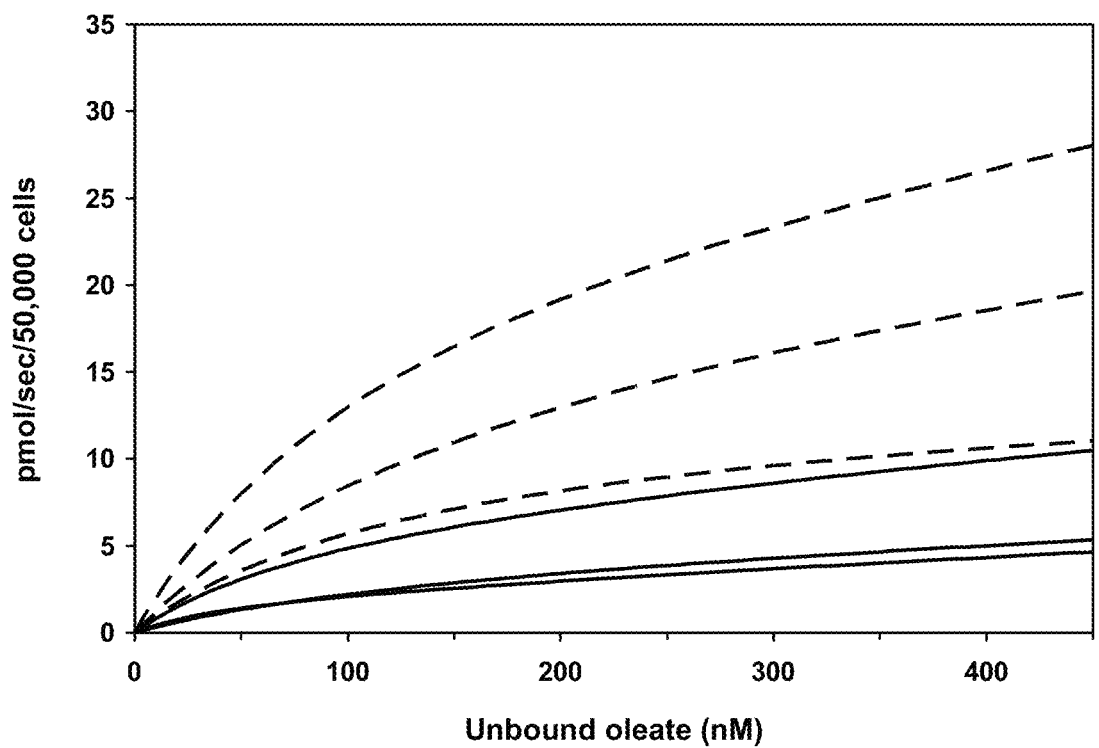
FIG. 13 is a graph showing fatty Acid Uptake Curves. [$^3$H]-oleic acid uptake by omental adipocytes was studied in 3 obese (dashed curves) and 3 normal wt individuals (solid curves). The curves represent computer fits to the sum of a saturable plus a non-saturable function of the unbound oleic acid concentration. There was no overlap between the two groups.

LCFA Uptake Kinetics: Computer fits of the LCFA uptake curves in the six study subjects in Cohort 1 are illustrated in FIG. 13. As in a series reported previously (A16), there was no overlap whatsoever in the curves from obese, compared with non-obese subjects. Both the $V_{max}$ for saturable LCFA uptake and the rate constant (k) for non-saturable uptake were increased in adipocytes from the obese patients. The increase in $V_{max}$ was statistically significant; increases in k, and in the ratio of $V_{max}$ to cell surface area were not. As with some of the biochemical values and measures of adipocyte size, the comparisons between obese and non-obese subjects paralleled those reported in the larger, earlier series (A16). Failure of differences between groups for some parameters to achieve statistical significance in the present study results principally from the small sizes of the groups comprising Cohort 1.

Microarray Analysis: In Cohort 1, the expression of approximately 10,000 human genes and expressed sequence tags (ESTs) was measured using Codelink Human 10K microarray in each sample of omental fat from obese individuals (n=3) and normal weight donors (n=3). In cohort 2, Codelink Human Whole Genome microarrays queried expression of 50,000 genes and ESTs in each sample. Thus, samples in Cohort 2 were evaluated for expression of ~5 times as many genes and ESTs as those in Cohort 1. Median normalized expression values were analyzed using the GeneSifter (Geospiza, Seattle, Wash.) software suite for the identification of differentially expressed genes, and of KEGG pathways with significantly altered gene expression.

Figure 14:
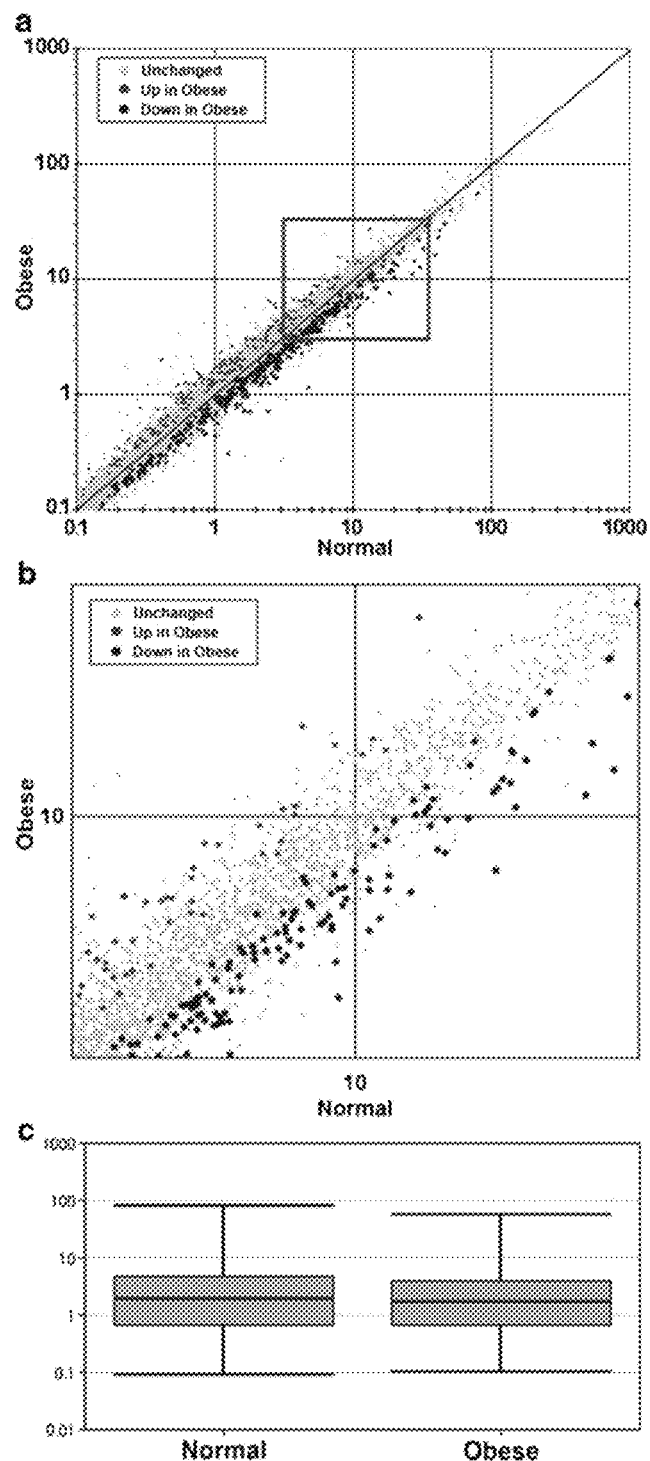
FIG. 14 shows comparisons of obese vs. normal omental fat mRNA expression (Cohort 1). The expression levels of approximately 9,200 genes were queried by microarray.

Measures of quality control of expression data: In the Cohort 1 studies, a log-log plot of the means of obese (ordinate) versus normal (abscissa) expression values for each data point is seen in FIG. 14A (complete data set) and FIG. 14B (enlarged section enclosed by the magenta square). The limited data scatter on either side of the line of identity indicates the overall equivalence of the two data sets, while the statistically significant genes (T-test, no correction for multiple testing) indicates the tightness of the data scatter for individual genes. A second indication of this overall equivalence is a comparison of the four mitochondrial ribosomal genes (L12, L38, L42 or S7) on the chips. None of these four "housekeeping genes" demonstrates significant differences in expression between the two sample sets, showing the overall metabolic equivalence between the obese and normal fat depots. A third measure of overall equivalence can be seen in the corresponding quartile plots (FIG. 14C: obese, left, and normal, right), which reveal no systematic differences between the data sets. These three global measures of gene expression indicate that there are no systematic differences between the two data sets, indicating that valid biological conclusions can be drawn if differences in expression are detected for particular individual genes. Highly similar quality control comparisons were obtained from the Cohort 2 samples.

Figure 15:
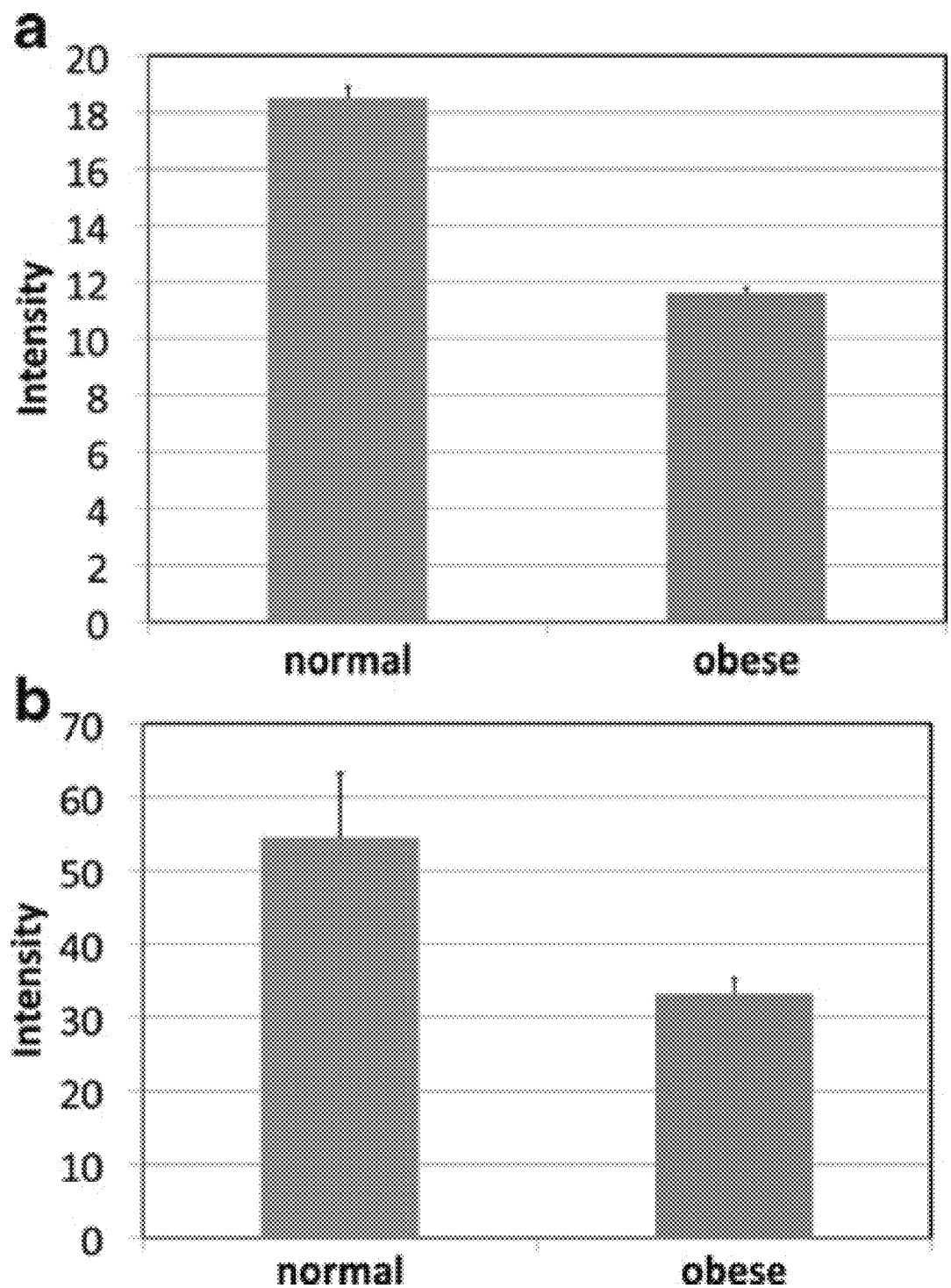
FIG. 15 shows bar graphs of the expression of dodecenoyl-CoA isomerase (DCI) mRNA in normal vs. obese omental fat samples. DCI mRNA expression in obese fat is reduced versus control fat. In cohort 1, DCI mRNA in omental fat depots from normal and obese individuals demonstrates a 1.59 fold under expression in obese patients (FIG. 15A), while in cohort 2 (FIG. 15B), very similar results were seen using whole genome arrays, with a 1.64 fold under expression in obese omental fat.

Identification of individual genes that are differentially expressed in obese fat: Pairwise comparisons between the three obese and the three normal samples in Cohort 1 were performed with minimum fold changes in expression, followed by standard t tests and corrections for multiple testing. Using criteria of an expression difference of ≥1.5-fold and a p value of ≤0.05, 166 differentially expressed genes and ESTs were identified in the Cohort 1 Analyses. However, after applying the Benjamini and Hochberg correction for multiple testing (A39), only one gene from this set, Dodecenoyl-Coenzyme A delta isomerase (3,2-trans-enoyl-Coenzyme A isomerase) (DCI) demonstrated a statistically significant difference between the two groups in Cohort 1, being under-expressed 1.6 fold in obese fat (FIG. 15A). This gene encodes a member of the hydratase/isomerase superfamily. The protein encoded is a key mitochondrial enzyme involved in beta-oxidation of unsaturated fatty acids. It catalyzes the transformation of 3-cis and 3-trans-enoyl-CoA esters arising during the stepwise degradation of cis-, mono-, and polyunsaturated fatty acids to the 2-trans-enoyl-CoA intermediates. For Cohort 2 samples, the results were nearly identical for DCI expression differences between obese and normal omental fat samples (FIG. 15B).

Lipolysis Related Gene Expression in Obese Fat: The initial step in the release of fatty acids from triacylglycerol stores is their hydrolysis via hormonally regulated lipolysis. Two key genes in this process, adenylate cyclase 6 (FIG. 16A and FIG. 16B) and adenylate cyclase activating peptide receptor 1 (FIG. 16C and FIG. 16D) are both under-expressed in the obese fat samples in both cohorts. Adenylate cyclase 6 encodes a membrane-associated enzyme that catalyzes the formation of the second messenger cyclic adenosine monophosphate (cAMP). Adenylate cyclase activating polypeptide 1 receptor type I, encodes a membrane-associated receptor protein which mediates diverse biological actions of adenylate cyclase activating polypeptide 1, and is positively coupled to adenylate cyclase. The fact that both of these key genes in the adenylate cyclase signaling cascade are under-expressed in obese omental fat indicates that this tissue demonstrates reduced responses to physiologic stimulation by lipolyic hormones.

KEGG Pathway Analysis: To identify a larger group of differentially expressed genes for inclusion in the pathway analysis, all genes in a pair-wise comparison were selected with an uncorrected p value ≤0.05, without correction for multiple testing, since the pathway analysis itself applies a second level statistical filter. Using this uncorrected p value criterion, 612 differentially expressed genes and ESTs between obese and normal fat were identified from the list of 10,000 that were queried in Cohort 1. This list of differentially expressed genes was subjected to KEGG pathway analysis for the identification of biological pathways with significantly altered gene expression in obese versus normal fat, as indicated by significant z up or z down scores. The complete set of down regulated KEGG pathways found in Cohort 1 is presented in Table 6. No pathways with z up scores had enough differentially expressed genes to be considered biologically significant.

TABLE 6

KEGG pathways with significant z down scores.

| KEGG pathway | Genes on array | Genes regulated | Up | Down | z score down Cohort 1 | Cohort 2 |
|---|---|---|---|---|---|---|
| Oxidative phosphorylation | 51 | 8 | 0 | 8 | 4.22 | 3.67 |
| Synthesis and degradation of ketone bodies | 5 | 2 | 0 | 2 | 3.99 | 2.95 |
| Fatty acid metabolism | 37 | 6 | 0 | 6 | 2.31 | 1.59 |

Of the pathways with significant z down scores and a sufficient genes involved to indicate biological relevance, Oxidative Phosphorylation and Fatty Acid Metabolism, both directly related to energy metabolism and fatty acid biosynthesis and degradation (A37), stand out. Of the genes in each pathway that demonstrate differential expression in Cohort 1, all are under-expressed in obese fat samples relative to the samples from normal weight individuals (eight genes in the Oxidative Phosphorylation pathway, and six genes in the Fatty Acid Metabolism pathway), in 12 of 14 instances with a fold change of ≥1.2. Results for these 12 genes in Cohort 2 were generally very similar to those described below (Tables 7 and 8).

TABLE 7

Downregulated genes in oxidative phosphorylation pathway.

| Gene | ID | EC | Complex | Fold change down Cohort 1 | Cohort 2 |
|---|---|---|---|---|---|
| NADH dehydrogenase (ubiquinone) Fe—S protein 7, 20 kDa (NADH-coenzyme Q reductase) | NDUFS7 | 1.6.5.3; 1.6.99.3 | I | 1.48 | 1.31 |
| Succinate dehydrogenase complex, subunit A. flavoprotein (Fp) | SDHA | 1.3.5.1 | II | 1.40 | 1.16 |
| Cytochrome c-1 | CYC1 | 1.10.2.2 | III | 1.48 | 1.37 |
| Cytochrome c oxidase subunit IV isoform 1 | COX4H | 1.9.3.1 | IV | 1.51 | 1.11 |
| ATPase, H+ transporting, lysosomal 50/57 kDa, VI subunit H | ATP6V1H | 3.6.3.14 | V | 1.55 | 1.24 |
| ATP synthase, H+ transporting, mitochondrial F0 complex, subunit G | ATP5L | 3.6.1.14 | V | 1.35 | 1.37 |
| ATP synthase, H+ transporting, mitochondrial F1 complex, delta subunit | ATP5D | 3.6.1.14 | V | 1.51 | 1.12 |

TABLE 8

Downregulated genes in fatty acid metabolism pathway.

| | | | Fold change down | |
|---|---|---|---|---|
| Gene | ID | EC | Cohort 1 | Cohort 2 |
| Acyl-coenzyme A oxidase 1, paimitoyl | ACOX1 | 1.3.3.6 | 1.36 | 1.02 |
| Alcohol dehydrogenase 1A (class, I), alpha polypeptide | ADH1A | 1.1.1.1 | 2.21 | 1.91 |
| Dodecenoyl-coenzyme A delta isomerase (3,2-trans-enoyl-coenzyme A isomerase) | DCI | 5.3.3.8 | 1.59 | 1.64 |
| 3-Hydroxyacyl-coenzyme A dehydrogenase | ECHD | 1.1.1.35 | 1.59 | 1.54 |
| Peroxisomal D3, D2-enoyl-CoA isomerase | PECI | 5.3.3.8 | 1.25 | 1.08 |

The individual genes that were under-expressed in the Oxidative Phosphorylation pathway in Cohort 1 with a fold change ≥1.2 are presented in Table 7. They include two H+ transporting mitochondrial ATP synthases, one lysosomal H+ transporting ATPase, two cytochrome c genes, and two dehydrogenases (ubiquinone and flavoprotein). Of the hundreds of proteins that make up the various enzymatic and electron transport complexes found in the inner mitochondrial membrane, the expression of the genes encoding seven of these proteins is down-regulated in obese omental fat. Five of these genes encode proteins that are regulatory enzymes or transport molecules, and these are spread across all 5 of the large complexes comprising the electron transport chain. As a result, even minor down-regulation of each of these, when factored together, can result in an important functional difference in production of ATP by Complex V. The functional organization of these down-regulated genes and their coordinate regulation has been brought into focus by the new pathway analysis employed in this study.

Figure 17:
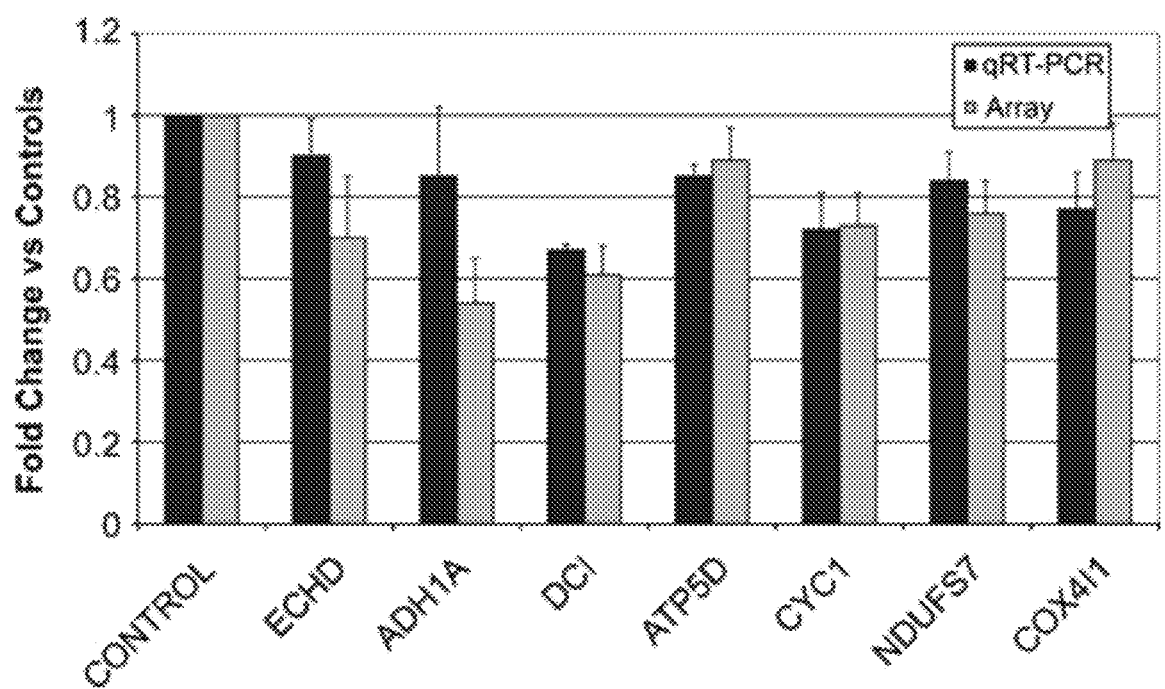
FIG. 17 is a bar graph showing the biological and technical validation of key gene expression results in Cohort 1 by Alternative Microarray and qRT-PCR in Cohort 2. Key genes which were under-expressed in obese omental fat in cohort 1 were selected for repeat testing in cohort 2 samples. Biological and technical validation was achieved in cohort 2 by both alternative microarray platform and qRT-PCR analysis. The ratio of gene expression in obese vs. normal fat in the Cohort 2 samples is presented for each of 7 genes identified as down-regulated in obesity in the original Cohort 1 study. The new results, show that all 7 genes are again underexpressed in obese omental fat in the Cohort 2 samples (n=7) vs normal weight controls (n=4). It is striking that for 5 of 7 genes assayed by both technologies, the relative expression ratios are within 10% of each other. The genes illustrated are ECHD (Enoyl Coenzyne A hydratase); ADH1A (Alcohol dehydrogenase 1A); DCI (Dodecenoyl-Coenzyme A delta isomerase); ATP5D (ATP synthase mito F1); CYC1 (cytochrome c-1); NDUFS7 (NADH dehydrogenase Fe—S); COX4I1 (Cytochrome c IV).
Figure 18:
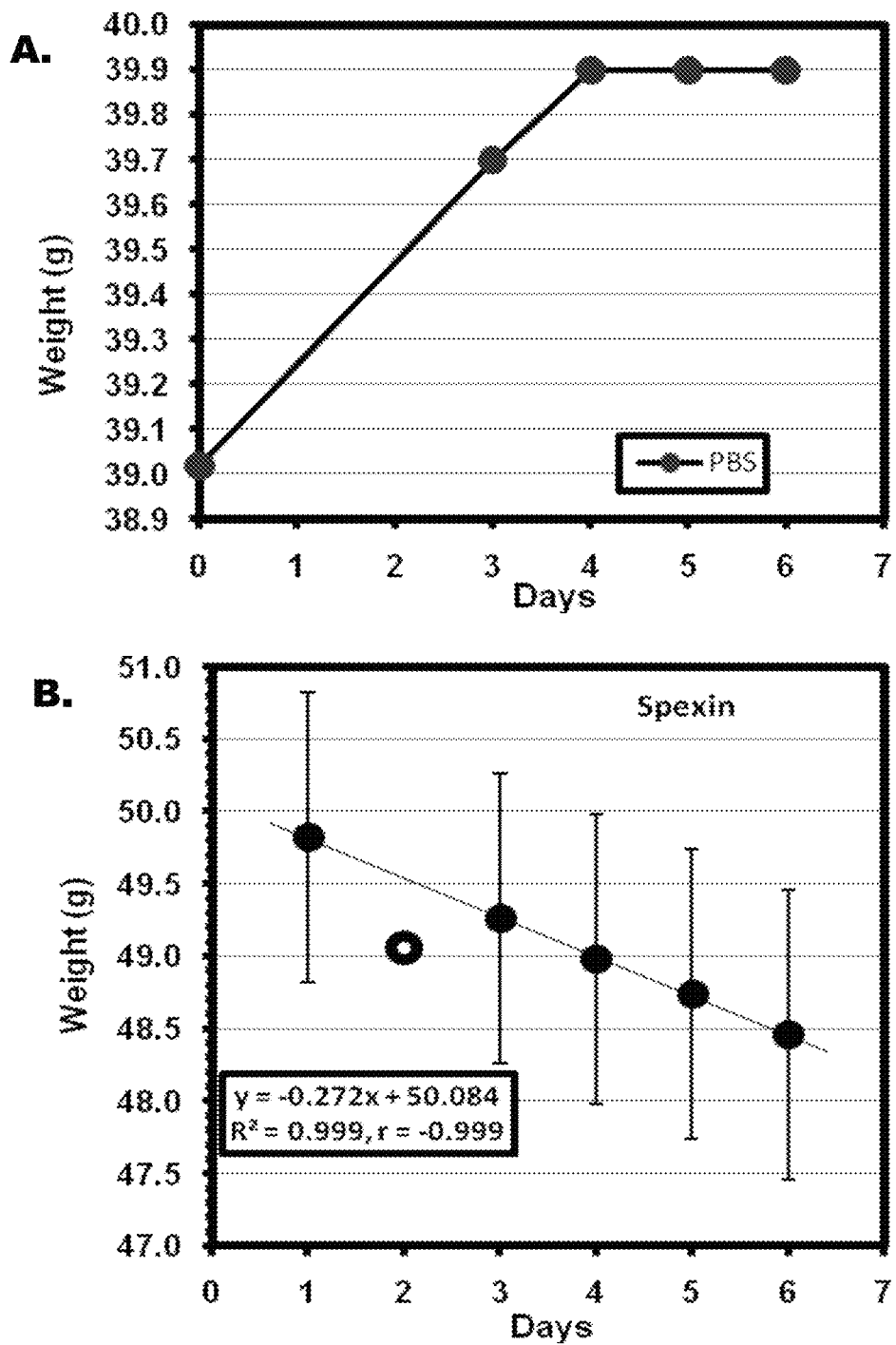
FIG. 18 shows graphs of the effect of daily Spexin Injection on High-Fat-Diet mouse weights. Two groups of Diet Induced Obesity (DIO) mice, housed under normal conditions and fed a special chow with approximately 60% of calories as fat, were injected daily for 6 days with 0.2 ml of either 1×PBS vehicle (n=5), or 1× PBS containing Spexin at a concentration of 2500 ng/mL (n=5).

In complex I, NADH dehydrogense (1.6.5.3/1.6.99.3) is the first enzyme of the complex that catalyzes the transfer of electrons from NADH to coenzyme Q. In Complex II, succinate dehydrogenase (1.3.5.1) reduces succinate to fumarate. In Complex III, ubiquinol-cytochrome-c reductase (1.10.2.2) is the heme-containing component of the cytochrome b-c1 complex, which accepts electrons from Rieske protein and transfers electrons to cytochrome c in the mitochondrial respiratory chain. In Complex IV, Cox4I1 (1.9.3.1) is one of the nuclear-encoded polypeptide chains of cytochrome c oxidase, the terminal oxidase in mitochondrial electron transport. In complex V, ATPase, H+ transporting, mitochondrial F1 complex, delta subunit (ATP6V1H, 3.6.3.14) activates the ATPase activity of the enzyme and couples ATPase activity to proton flow. Genes under-expressed with a fold change ≥1.2 in obese fat samples from Cohort 1 that are components of the Fatty Acid Metabolism pathway are presented in Table 77. These genes include acylCoenzyme A oxidase, alcohol dehydrogenase 1A, DCI, another isomerase (peroxisomal D3,D2-enoyl-CoA isomerase), and hydroxyacyl-Coenzyme A dehydrogenase.

qRT-PCR: Expression of seven genes from either the Oxidative Phosphorylation or Fatty Acid Metabolism pathways which were found to be under-expressed by microarray analysis in Cohort 1 was examined in the Cohort 2 samples by qRT-PCR. The genes are ECHD (3-Hydroxyacyl-Coenzyme A dehydrogenase); ADH1a (Alcohol dehydrogenase 1A); DCI (Dodecenoyl-Coenzyme A delta isomerase); ATP5D (ATP synthase, mito F1); CYC1 (cytochrome c-1); NDUFS7 (NADH dehydrogenase Fe—S); COX4I1 (Cytochrome c oxidase IV) (FIG. 17). Seven of these genes were under-expressed in Cohort 2 as assessed with the Whole Human Genome microarray. Thus, there was complete concordance between the Human Whole Genome array and qRT-PC with regard to the direction of regulation of expression of these 7 genes. Also, for the seven genes queried, the direction of difference in expression between obese and controls is also consistent between the two sample sets (Cohort 1 and Cohort 2), since these seven genes are all under-expressed in the obese fat samples. These findings are consistent with a generally reduced energy metabolism in obese fat.

Discussion

Obesity is the increased deposition of LCFA, principally in the form of TG, in adipose and other tissues. That this deposition is highly selective, and that its extent and turnover differ even between different adipose tissue depots (e.g. A40-43), indicates that there is a complex underlying pathophysiology that involves far more than the passive, unregulated diffusion of LCFA—the essential building blocks of TG—across cell membranes. Many processes can contribute to TG accumulation: increased LCFA uptake or synthesis, increased LCFA conversion to TG, or increased uptake of pre-formed TG from lipoproteins; or alternatively decreased TG or LCFA removal by decreasing TG lipolysis, decreased LCFA and TG excretion as components of VLDL, or decreased LCFA oxidation (A18, A22-24, A44-46). These multiple processes involve multiple genes, e.g. for plasma membrane and intracellular LCFA transporters; for enzymes of fatty acid or triglyceride synthesis; for receptors, enzymes and other proteins associated the import and/or hydrolysis of pre-formed lipoprotein-triglycerides, such as the LDL receptor, hepatic lipase, and lipoprotein lipase (LPL); genes associated with VLDL synthesis, assembly and export; and proteins and enzymes of fatty acid oxidation; not to mention numerous transcription factors and other regulatory genes. It would be desirable to assay these processes simultaneously. While the key genes involved in many of these processes have been identified, for other processes, including cellular LCFA uptake, key genes are unknown (A47, A48). Several of the processes, such as cellular LCFA uptake and oxidation, can be assayed directly. While direct quantitation of others is more difficult, a first-order approximation can be obtained via RNA expression studies.

Microarray Expression Analysis. Without being bound by theory, the number of known genes potentially involved in obesity pathogenesis is at least 50 (A22). RNA expression microarray technology is an effective approach for analyzing a large number of genes, and also for identifying genes whose role in the process of interest—in this case, obesity—is unknown. Microarrays simultaneously monitor expression of thousands of mRNAs from individual samples. In addition to providing information regarding the expression of pre-selected candidate genes, the high-throughput nature of microarray analysis is ideal for the identification of candidate genes and/or pathways responsible for the pathophysiology of complex diseases such as obesity.

Data discussed herein was analyzed using a two stage approach. The first stage was to identify individual genes whose expression was significantly different between normal and obese omental fat samples. Using a standard cut-off of 1.5 fold difference in expression, along with Benjamini and Hochberg correction for multiple testing (39), a single gene, Dodecenoyl-Coenzyme A delta isomerase (DCI) or 3,2 trans-enoyl-Coenzyme A isomerase, was identified in Cohort 1 as being under-expressed in obese omental fat. Its under-expression was confirmed in Cohort 2 both by microarray and qRT-PCR expression analyses, providing both biological and technical validation of this result. This gene is a mitochondrial enzyme involved in the β-oxidation of unsaturated fatty acids. Metabolic intermediates produced during the stepwise degradation of unsaturated LCFA enter the Citric Acid Cycle, where they contribute to ATP production by oxidative phosphorylation. Central obesity has been positively associated with an increase in n-6 unsaturated fatty acids, and inversely associated with mono-unsaturated fatty acids (A49).

Genomic Organization of DCI. This gene is located at chromosomal locus 16 p13.3, encoding a predicted protein of 302 amino acids (ENTREZ [NM_001919]). Locus 16p13.3 has twice been linked to obesity-related factors, including BMI, both by logarithm of the odds score (LOD score) of microsatellite marker D16S510 in a study of Old Order Amish families (A50) and in a genome scan of African American families enriched for non-diabetic neuropathy (A51). These reports and the reduction of DCI expression described herein make this a candidate gene for further study in obesity. The ~50% loss of DCI expression is consistent with functional loss of one DCI allele, which could reflect microdeletions in this gene region, or single nucleotide polymorphisms (SNPs) adversely affecting the splicing or stability of the DCI message.

KEGG Pathway Analysis. The power of microarray analysis is that it allows the simultaneous screening of thousands of genes in each sample, unbiased by candidate gene pre-selection. Recent advances in software allow changes in gene expression to be considered in the context of biological pathways. The Kyoto Encyclopedia of Genes and Genomics (KEGG) consortium (www.genome.jp/kegg; 37) has established a collection of gene pathways whose gene members are known to interact as parts of a greater whole. Significant changes in pathway member gene expression, especially when the changes are co-ordinate (eg: involving several sequential members of a signaling pathway) indicate that biologically meaningful alterations of pathway regulation and/or function are likely. Moreover, relatively small changes in expression of multiple genes in a pathway, each too small to achieve significance individually, can lead to biologically significant alterations in throughput along a pathway. For example, using a simplistic model, 10% down-regulation of 7 genes in a pathway, where each can be overlooked by single gene analysis, could result in a biologically significant reduction of ≥50% in throughput along the pathway.

Oxidative Phosphorylation KEGG Pathway. The Oxidative Phosphorylation pathway captures the energy released by the oxidation of NADH and succinate in the citric acid cycle, producing adenosine triphosphate (ATP) via ATP synthase. Of the 51 genes in this pathway that are included on the arrays used in this study, seven are differentially expressed, and these seven are all under-expressed in obese fat. Data discussed herein show that two protein components of the ATP synthase complex are down-regulated in obese fat: the G subunit of the ATP synthase F0 complex, and the delta subunits of the F1 complex). These results further show that components of the electron transport chain, including cytochrome c oxidase, and cytochrome c-1, plus NADH dehydrogenase and succinate dehydrogenase (sub-unit A) are also under-expressed. Without being bound by theory, ATP production can be decreased in obese fat tissues if levels of the corresponding proteins are also diminished. It is important to recognize that each of the five complexes is built up of many subunits, that depend on a delicate macrostructure.

Data discussed herein showing under-expression of all 7 of the 7 differentially expressed genes involved in oxidative phosphorylation are in agreement with similar findings in monozygotic twins that were discordant for obesity (A52). Microarray analysis of fat biopsies identified 30 genes in the oxidative phosphorylation pathway that were under-expressed in the obese subjects compared with their non-obese twins. A number of these genes were also under-expressed, including ATP5L, ATP5B, ATPV1H, and CYC1. Mustelin et al. also found members of the NADH dehydrogenase complex to be under-expressed in obese fat. Similar data have been reported by Patti et al (A53), who found a coordinated reduction in oxidative metabolism gene expression in skeletal muscle of type II diabetic Mexican-Americans, related to the reduced expression of two transcription factors, nuclear respiratory factor 1 (NRF-1) and PPARγ co-activator 1, which are known to regulate expression of genes in the oxidative phosphorylation pathway. The genes encoding these transcription factors are not present on the 10K microarrays used in the original studies. In the cohort 2 samples, NRF-1 and PPARγ co-activator 1 were essentially unchanged, indicating that another mechanism can be responsible for the consistent down-regulation of the oxidative phosphorylation pathway genes in obese omental fat.

Figure 12:
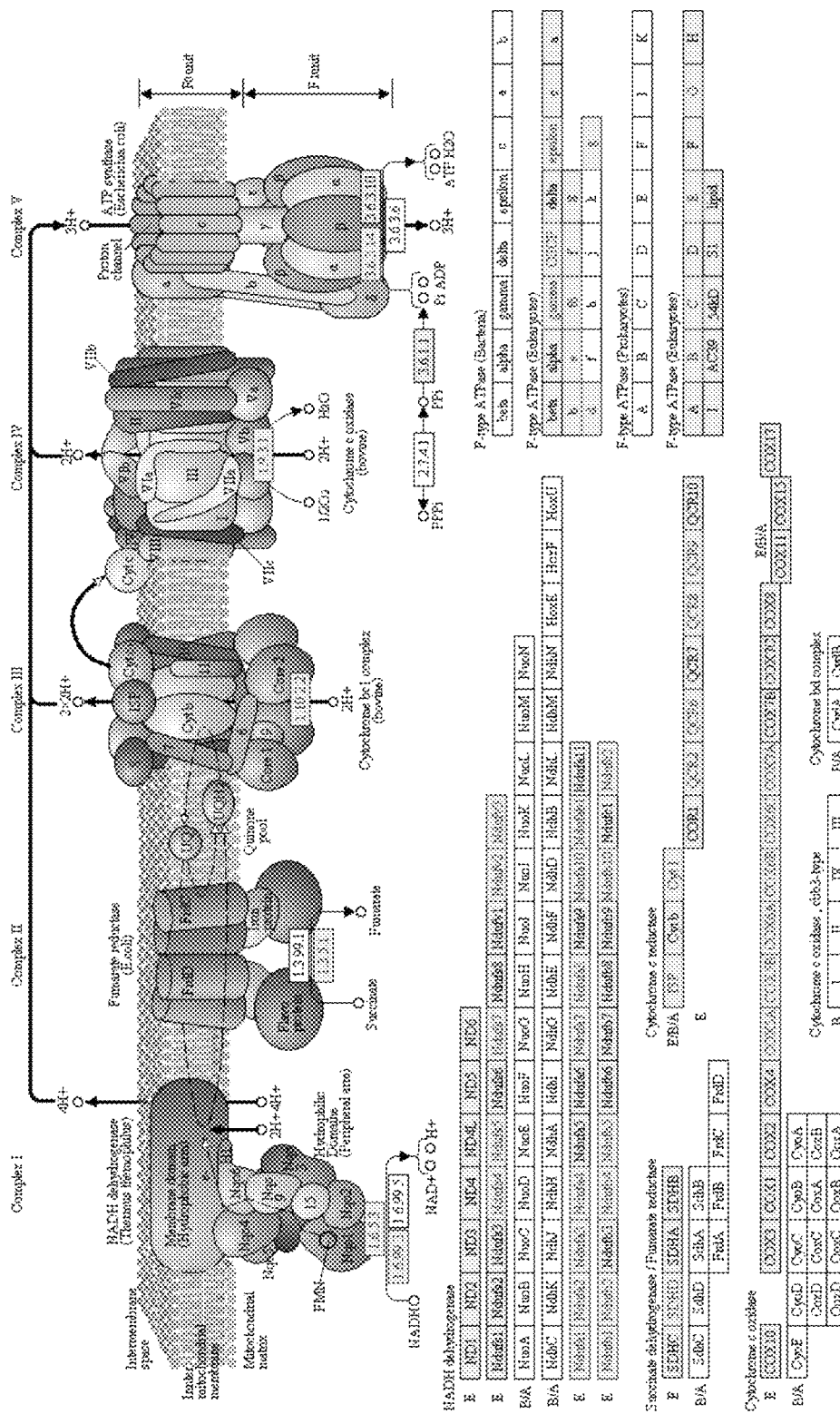
FIG. 12 is a schematic showing Complexes I-V of the oxidative phosphorylation (Ox-Phos) pathway. These five complexes of the Ox-Phos pathway are responsible for the generation of ATP from energy released by the citric acid cycle. The major subunits of each complex are drawn in the diagram, and boxes indicating key enzymes are labeled with the appropriate EC classification number. Boxes/EC numbers highlighted in red indicate enzymes that are differentially expressed in obesity. One striking result is that the eight genes that are coordinately down-regulated are distributed across all five complexes. (Walewski, et al; 2010). One key point to consider is that while 15-50% differences in gene expression (assuming the protein drops by a corresponding amount) can not be considered all that important in terms of final throughput unless these are rate-limiting enzymes. While the total protein can be lower, there is usually excess functional capacity, assuming enzyme distribution or co-regulatory functions are not important for these proteins in solution. However, in this case, the proteins in question are members of large membrane bound complexes, where the correct stoichiometry of the individual proteins in the overall architecture of the complex is quite important. A 15-50% reduction in the amount of an individual protein could reasonably be expected to affect the structural, and consequently functional, properties of the complex. Even more striking, is the coordinate reduction in the expression of key genes across each of the 5 complexes of the electron transport chain.

Fatty Acid Metabolism KEGG Pathway. The Fatty Acid Metabolism pathway includes the enzymes responsible for the biosynthesis and degradation of LCFAs, leading to the production of Acetyl-CoA, which is then directed into the TCA cycle. From there, oxidation of NADH and succinate produce ATP via ATP synthase in the Oxidative Phosphorylation pathway. Of the 37 genes probed by the arrays, six of six with differential expression were all under-expressed in obese fat. Each of these underexpressed genes plays a role in the metabolism of LCFA, and several have already been reported to play a role in obesity. Acyl-Coenzyme A oxidase 1 (1.3.3.6) expression in omental fat reportedly predicts weight loss outcome after gastric by-pass surgery (A54). DCI (5.3.3.8), grouped with 3-Hydroxyacyl-Coenzyme A dehydrogenase (1.1.1.35) in FIG. 12, plays a key role in LCFA degradation. A higher incidence of childhood obesity has been reported in children with long chain 3-Hydroxyacyl-Coenzyme A dehydrogenase (LCHAD) or trifunctional protein (TFP) deficiency. Placing these children on low fat, high protein and lower carbohydrate diets, resulted in lower energy intake, and increased energy expenditure (A55).

Lipolysis Related Gene Expression. Results discussed herein showing reduced expression of key genes in the cAMP mediated signaling of hormonally stimulated lipolysis are consistent with reports showing a blunted lipolytic response to catecholamine stimulation in obese individuals, especially in abdominal fat (A56) and adipocytes from obese individuals, due in part to reduced expression of hormone sensitive lipase (A57). However, fuller understanding of this complex system awaits ongoing transcriptome studies.

ABC-Transporters KEGG Pathway. One of the genes in this pathway encodes ATP-binding cassette, sub-family D (ALD), member 3 (ABCD3), a member of the superfamily of ATP-binding cassette (ABC) transporters. ABC proteins transport various molecules across extra- and intra-cellular membranes. ABCD3 is a member of the ALD subfamily, which is involved in peroxisomal import of fatty acids and/or fatty acyl-CoAs into the organelle. While little is known about this gene in human obesity, its up-regulation discussed herein is interesting in light of its known role in intracellular LCFA transport. Without being bound by theory, increased peroxisomal LCFA import and subsequent oxidation can partly substitute for the decreased mitochondrial β-oxidation indicated by other findings merits further study.

Validation of Results. It is widely accepted that microarray results analyses require validation. This can involve biological validation in a second, independently collected set of samples, and technological validation by using an alternative microarray platform or an entirely different technology such as qRT-PCR. Validation can also be accomplished by measurements of the proteins encoded by regulated genes, or of biological activity. In the present study, biological validation was achieved by the study of two independently collected sample sets, and technical validation by the use of two different micro-array platforms and qRT-PCR.

In the early days of micro-array analysis very large sample sizes were considered essential due to concerns about the statistical issues involved in making thousands of simultaneous comparisons on a given sample. As the statistical theory developed for this issue, the numbers required have dropped dramatically. The consensus report of a major conference sponsored by all of the major government science agencies in 2006 concluded that an n=5 per group was sufficient for most micro-array analyses (A58). Since that conference numbers have dropped further. An appreciable number of microarray papers have been published in reputable journals based on studies in even smaller cohorts, including those in which n=3 per group (e.g. A59-61). The present study is well within the published 2006 guidelines.

Because different cell populations within a tissue can express particular genes at different rates, it was once considered important to fractionate tissues into purified cell populations before performing micro-array analyses. This can still be useful in specific instances, but gene expression array studies have tended to move away from this since cell isolation procedures themselves can introduce major artifactual changes in gene expression. This has been especially well studied in whole blood vs. PBMC comparisons, where changes in RNA expression due to experimental manipulation can seriously mask what was going on in vivo (A62). Many currently believe that cell fractionation is essential only in specific situations. The present studies were preformed in unfractionated adipose tissue samples. Without being bound by theory, increased macrophage infiltration into obese fat influencing comparisons with results in non-obese fat seem very unlikely in a study, such as this one, in which the key results are down-regulation of multiple biologically relevant genes in the obese fat samples. Further, the expression ratio of 23 macrophage-specific genes in unfractionated obese vs. non-obese omental fat averaged 1.1±10.06, strongly arguing against the possibility that the observed down-regulation of DCI and related genes reflected macrophage infiltration.

Working Model of Accumulation of Long Chain Fatty Acids in Obese Adipocytes. Many laboratories have examined the balance between LCFA uptake, LCFA disposition, and cellular TG content in the liver as it relates to the pathogenesis of hepatic steatosis (A18, A22-24, A44-46). Similar considerations apply to adipocytes and the pathophysiology of obesity. In adipocytes of normal weight subjects, allowing for meal-related diurnal variation, LCFA uptake (including facilitated transport) and degradation (including β-oxidation) or elimination (e.g. lipolysis) are in balance. Consequently, the net amount of fat in each cell is essentially constant over time, resulting in the relatively stable weights seen in non-obese subjects. In contrast, in adipocytes from obese subjects, the combination of increased facilitated LCFA uptake, shown in the uptake studies discussed herein, and reduced β-oxidation, lipolysis and LCFA metabolism, indicated by gene expression analysis, leads to accumulation of LCFAs and TG over time.

The result of the observed changes in LCFA kinetics and expression of metabolic genes will be chronic accumulation of LCFA and TG, resulting in enlarged adipocytes and significant weight gain over time. The strength of this study is the combination of the high-throughput first stage, where thousands of genes are queried; and the systems biology approach of the second stage, where established pathways that contain a statistically significant number of genes with altered expression are identified. The combination of microarray analysis with extensive pathway filtering of identified genes is increasingly considered a state-of-the-art approach, which should guide future experimental validation. Without being bound by theory, synergistic effects of drug cocktails whose components are aimed at various targets in these pathways can work at lower individual doses, with less toxicity, and in more patients, than drugs that target only one of a pathway's many gene components. The interface between bariatric surgery and basic science can prove to be the optimal place to carry out this critically important translational research.

REFERENCES

A1. Stremmel W, Berk P D. Hepatocellular influx of [14C] oleate reflects membrane transport rather than intracellular metabolism or binding. *Proc Natl Acad Sci USA*. 1986; 83(10):3086-3090.

A2. Schwieterman W, Sorrentino D, Potter B J, et al. Uptake of oleate by isolated rat adipocytes is mediated by a 40-kDa plasma membrane fatty acid binding protein closely related to that in liver and gut. *Proc Natl Acad Sci USA*. January 1988; 85(2):359-363.

A3. Sorrentino D, Stump D, Potter B J, et al. Oleate uptake by cardiac myocytes is carrier mediated and involves a 40-kD plasma membrane fatty acid binding protein similar to that in liver, adipose tissue, and gut. *J Clin Invest*. September 1988; 82(3):928-935.

A4. Stremmel W. Uptake of fatty acids by jejunal mucosal cells is mediated by a fatty acid binding membrane protein. *J Clin Invest*. December 1988; 82(6):2001-2010.

A5. Nunes R M I L, Sorrentino D, Berk P D. Oleate uptake by isolated hepatocytes consists of two components, each driven by the unbound oleate concentration: Proceedings, 3rd International Congress, Mathematical Modelling of Liver Excretory Process, Juntendo University Press, Tokyo, 1990; 312-316.

A6. Stump D D, Nunes R M, Sorrentino D, Isola L M, Berk P D. Characteristics of oleate binding to liver plasma membranes and its-uptake by isolated hepatocytes. *J Hepatol*. 1992; 16(3):304-315.

A7. Berk P D, Stump D D. Mechanisms of cellular uptake of long chain free fatty acids. *Mol Cell Biochem*. February 1999; 192(1-2):17-31.

A8. Stump D D, Fan X, Berk P D. Oleic acid uptake and binding by rat adipocytes define dual pathways for cellular fatty acid uptake. *J Lipid Res*. April 2001; 42(4): 509-520.

A9. Abumrad N A, Perkins R C, Park J H, Park C R. Mechanism of long chain fatty acid permeation in the isolated adipocyte. *J Biol Chem*. Sep. 10 1981; 256(17): 9183-9191.

A10. Abumrad N A, Park J H, Park C R. Permeation of long-chain fatty acid into adipocytes. Kinetics, specificity, and evidence for involvement of a membrane protein. *J Biol Chem*. Jul. 25 1984; 259(14):8945-8953.

A11. Glatz J F, van Nieuwenhoven F A, Luiken J J, Schaap F G, van der Vusse G J. Role of membrane-associated and cytoplasmic fatty acid-binding proteins in cellular fatty acid metabolism. *Prostaglandins Leukot Essent Fatty Acids*. October 1997; 57(4-5):373-378.

A12. Luiken J J, Turcotte L P, Bonen A. Protein-mediated palmitate uptake and expression of fatty acid transport proteins in heart giant vesicles. *J Lipid Res*. 1999; 40(6): 1007-1016.

A13. Luiken J J, Glatz J F, Bonen A. Fatty acid transport proteins facilitate fatty acid uptake in skeletal muscle. *Can J Appl Physiol*. October 2000; 25(5):333-352.

A14. Kampf J P, Kleinfeld A M. Fatty acid transport in adipocytes monitored by imaging intracellular free fatty acid levels. *J Biol Chem*. Aug. 20 2004; 279(34):35775-35780.

A15. Kleinfeld A M, Kampf J P, Lechene C. Transport of 13C-oleate in adipocytes measured using multi-imaging mass spectrometry. *J Am Soc Mass Spectrom*. November 2004; 15(11):1572-1580.

A16. Petrescu O, Fan X, Gentileschi P, et al. Long-chain fatty acid uptake is upregulated in omental adipocytes from patients undergoing bariatric surgery for obesity. *Int J Obes (Lond)*. 2005; 29(2):196-203.

A17. Fan X, Bradbury M W, Berk P D. Leptin and insulin modulate nutrient partitioning and weight loss in ob/ob mice through regulation of long-chain fatty acid uptake by adipocytes. *J Nutr*. 2003; 133(9): 2707-2715.

A18. Bradbury M W, Berk P D. Lipid metabolism in hepatic steatosis. *Clin Liver Dis*. 2004; 8(3): 639-671.

A19. Berk P D, Zhou S L, Kiang C L, Stump D, Bradbury M, Isola L M. Uptake of long chain free fatty acids is selectively up-regulated in adipocytes of Zucker rats with genetic obesity and non-insulindependent diabetes mellitus. *J Biol Chem*. 1997; 272(13): 8830-8835.

A20. Berk P D, Zhou S L, Bradbury M, Stump D, Kiang C L, Isola L M. Regulated membrane transport of free fatty acids in adipocytes: role in obesity and non-insulin dependent diabetes mellitus. *Trans Am Clin Climatol Assoc*. 1997; 108:26-40.

A21. Berk P D, Zhou S, Kiang C, Stump D D, Fan X, Bradbury M W. Selective up-regulation of fatty acid uptake by adipocytes characterizes both genetic and diet-induced obesity in rodents. *J Biol Chem*. 1999; 274(40): 28626-28631.

A22. Berk P D. The Master's Perspective: Regulatable fatty acid transport mechanisms are central to the pathophysiology of obesity, fatty liver, & metabolic syndrome. *Hepatol* 2008; 48: 1362-1376.

A23. Verna E C, Berk P D. Role of fatty acids in the pathogenesis of obesity and fatty liver: Impact of bariatric surgery. Semin Liver Dis 2008; 28(4): 407-426.

A24. Goldberg I J, Ginsberg H N. Ins and outs modulating hepatic triglyceride and development of nonalcoholic fatty liver disease. Gastroent 2006; 130(4):1343-1346.

A25. Di Girolamo M, Mendlinger S & Fertig J W. A simple method to determine fat cell size and number in four mammalian species. *Am J Physiol* 1971; 221: 850-858.

A26. Wosilait W D & Nagy P. A method of computing drug distribution in plasma using stepwise association constants: clofibrate acid as an illustrative example. *Comput Programs Biomed* 1976; 6: 142-148.

A27. Spector A A, Fletcher J E & Ashbrook J D. Analysis of long-chain free fatty acid binding to bovine serum albumin by determination of stepwise equilibrium constants. *Biochemistry* 1971; 10:3229-3232.

A28. Bojesen I N & Bojesen E. Binding of arachidonate and oleate to bovine serum albumin. *J Lipid Res* 1994; 35: 770-778.

A29. Richieri G V, Anel A & Kleinfeld A M. Interactions of long-chain fatty acids and albumin: determination of free fatty acid levels using the fluorescent probe ADIFAB. *Biochemistry* 1993; 32: 7574-7580.

A30. Rose H, Conventz M, Fischer Y, Jungling E, Hennecke T & Kammermeier H. Long-chain fatty acid-binding to albumin: re-evaluation with directly measured concentrations. *Biochim Biophys Acta* 1994; 1215: 321-326.

A31. Berman M & Weiss M F. *Users'manual for SAAM* US Government Printing Office: Washington D.C. 1967.

A32. *SAAM II user guide*, SAAM Institute: Seattle, Wash. 1998.

A33. Sorrentino D, Robinson R B, Kiang C L & Berk P D. At physiologic albumin/oleate concentrations oleate uptake by isolated hepatocytes, cardiac myocytes, and adipocytes is a saturable function of the unbound oleate concentration. Uptake kinetics are consistent with the conventional theory. *J Clin Invest* 1989; 84: 1325-1333.

A34. Snedecor G W & Cochran W G. *Statistical methods* 6th edn. Iowa State University Press: Ames, Iowa 1967.

A35. Ramakrishnan R, Dorris D, Lublinsky A, Nguyen A, Domanus M, Prokhorova A, Gieser L, Touma E, Lockner R, Tata M, Zhu X, Patterson M, Shippy R, Sendera T J, Mazumder A. An assessment of Motorola CodeLink microarray performance for gene expression profiling applications. Nucleic Acids Res. 2002; 30(7):e30.

A36. Ashburner M, Ball C A, Blake J A, Botstein D, Butler H, Cherry J M, Davis A P, Dolinski K, Dwight S S, Eppig J T, Harris M A, Hill D P, Issel-Tarver L, Kasarskis A, Lewis S, Matese J C, Richardson J E, Ringwald M, Rubin G M, Sherlock G. Gene ontology: tool for the unification of biology. The Gene Ontology Consortium. Nat Genet. 2000; 25(1):25-29.

A37. Kanehisa M, Goto S, Kawashima S, Okuno Y, Hattori M. The KEGG resource for deciphering the genome. Nucleic Acids Res. 2004; 32 D277-280.

A38. Doniger S W, Salomonis N, Dahlquist K D, Vranizan K, Lawlor S C, Conklin B R. MAPPFinder: using Gene Ontology and GenMAPP to create a global gene-expression profile from microarray data. Genome Biol. 2003; 4(1):R7.

A39. Benjamini, Y. and Hochberg, Y. (1995). "Controlling the False Discovery Rate: a Practical and Powerful Approach to Multiple Testing," Journal of the Royal Statistical Society B, 1995; 57, 289-300.

A40. Fried, S. K. and Kral, J. G. Sex differences in regional distribution of fat cell size and lipoprotein lipase activity in morbidly obese patients. Int J Obes 1987; 11(2):129-140.

A41. Edens, N. K., Fried, S. K., Kral, J. G., Hirsch, J., and Leibel, R. L. In vitro lipid synthesis in human adipose tissue from three abdominal sites. Am J Physiol 1993; 265(3 Pt 1):E374-379.

A42. Ostman, J., Amer, P., Engfeldt, P., and Kager, L. Regional differences in the control of lipolysis in human adipose tissue. Metabolism 1979; 28(12):1198-1205.

A43. Russell, C. D., Petersen, R. N., Rao, S. P., Ricci, M. R., Prasad, A., Zhang, Y., Brolin, R. E., and Fisher, F. M., McTernan, P. G., Valsamakis, G., Chetty, R., Harte, A. L., Anwar, A. J., Starcynski, J., Crocker, J., Barnett, A. H., McTernan, C. L., and Kumar, S. Differences in adiponectin protein expression: effect of fat depots and type 2 diabetic status. Horm Metab Res 2002; 34: 650-654.

A44. Chirieac D V, Chirieac L R, Corsetti J P, Cianci J, Sparks C E, Sparks J D. Glucose-stimulated insulin secretion suppresses hepatic triglyceride-rich lipoprotein and apoB production. *Am J Physiol Endocrinol Metab.* 2000; 279(5):E1003-1011.

A45. Diehl A M. Lessons from animal models of NASH. *Hepatol Res.* 2005; 33(2):138-144.

A46. Yamaguchi K, Yang L, McCall S, et al. Inhibiting triglyceride synthesis improves hepatic steatosis but exacerbates liver damage and fibrosis in obese mice with nonalcoholic steatohepatitis. *Hepatology.* June 2007; 45(6):1366-1374.

A47. Kampf J P, Parmley D, Kleinfeld A M. Free fatty acid transport across adipocytes is mediated by an unknown membrane protein pump. *Am J Physiol Endocrinol Metab.* 2007; 293(5):E1207-1214.

A48. Su X, Abumrad N A. Cellular fatty acid uptake: a pathway under construction. *Trends Endocrinol Metab.* 2009 March; 20(2): 72-7.

A49. Garaulet M, Pérez-Llamas F, Pérez-Ayala M, Martinez P, de Medina F S, Tebar F J, Zamora S. Site-specific differences in the fatty acid composition of abdominal adipose tissue in an obese population from a Mediterranean area: relation with dietary fatty acids, plasma lipid profile, serum insulin, and central obesity. Am J Clin Nutr. 2001; 74:585-591.

A50. Hsueh W C, Mitchell B D, Schneider J L, et al. Genomewide scan of obesity in the Old Order Amish. *J Clin Endocrinol Metab.* 2001; 86:1199-205.

A51. Freedman B I, Langefeld C D, Rich S S, Valis C J, Sale M M, Williams A H, Brown W M, Beck S R, Hicks P J, Bowden D W. A genome scan for ESRD in black families enriched for nondiabetic nephropathy. J Am Soc Nephrol. 2004; 15(10):2719-2127.

A52. Mustelin L, Pietiläinen K H, Rissanen A, Sovijärvi A R, Piirilä P, Naukkarinen J, Peltonen L, Kaprio J, Yki-Järvinen H. Acquired obesity and poor physical fitness impair expression of genes of mitochondrial oxidative phosphorylation in monozygotic twins discordant for obesity. Am J Physiol Endocrinol Metab. 2008; 295(1):E148-54.

A53. Patti M E, Butte A J, Crunkhorn S, Cusi K, Berria R, Kashyap S, Miyazaki Y, Kohane I, Costello M, Saccone R, Landaker E J, Goldfine A B, Mun E, DeFronzo R, Finlayson J, Kahn C R, Mandarino L J. Coordinated reduction of genes of oxidative metabolism in humans with insulin resistance and diabetes: Potential role of PGC1 and NRF1. Proc Natl Acad Sci USA. 2003; 100 (14):8466-71.

A54. Kim K, Perroud B, Espinal G, Kachinskas D, Austrheim-Smith I, Wolfe B M, Warden, CH.Genes and networks expressed in perioperative omental adipose tissue are correlated with weight loss from Roux-en-Y gastric bypass. International Journal of Obesity (2008) 32: 1395-1406.

A55. Gillingham M B, Purnell J Q, Jordan J, Stadler D, Haqq A M, Harding C O. Effects of higher dietary protein intake on energy balance and metabolic control in children with long-chain 3-hydroxy acyl-CoA dehydrogenase (LCHAD) or trifunctional protein (TFP) deficiency. Mol Genet Metab. 2007; 90(1):64-69.

A56. Buijs M M, Burggraaf J, Wijbrandts C, de Kam M L, Frölich M, Cohen A F, Romijn J A, Sauerwein H P, Meinders A E, and Pijl H. Blunted lipolytic response to fasting in abdominally obese women: evidence for involvement of hyposomatotropism. Am J Clin Nutr 2003; 77: 544-550.

A57. Langin D, Dicker A, Tavernier G, Hoffstedt J, Mairal A, Rydén M, Amer E, Sicard A, Jenkins C M, Viguerie N, van Harmelen V, Gross R W, Holm C, Amer P. Adipocyte lipases and defect of lipolysis in human obesity. Diabetes. 2005; 54(11):3190-3197.

A58. Shi, L., Reid, L. H., Jones, W. D., Shippy, R., Warrington, J. A., Baker, S. C., Collins, P. J., de Longueville, F., Kawasaki, E. S., Lee, K. Y., et al. 2006. The MicroArray Quality Control (MAQC) project shows inter- and intraplatform reproducibility of gene expression measurements. *Nat Biotechnol* 24:1151-1161.

A59. Bardag-Gorce F, Oliva J, Dedes J, Li J, French B A, French S W. Chronic ethanol feeding alters hepatocyte memory which is not altered by acute feeding. Alcohol Clin Exp Res. 2009; 33(4):684-692.

A60. Trentin L, Giordan M, Dingermann T, Basso G, Te Kronnie G, Marschalek R. Two independent gene signatures in pediatric t(4; 11) acute lymphoblastic leukemia patients. Eur J Haematol. 2009 Jun. 25.

A61. Ukena S N, Koenecke C, Geffers R, Fuehner T, Welte T, Ganser A, Buer J, Franzke A. T helper type 2 differentiation is associated with induction of antibacterial defense mechanisms in blood lymphocytes of patients with sarcoidosis. Immunol Invest. 2009; 38(1):49-66.

A62. Kennedy L, Vass J K, Haggart D R, Moore S, Burczynski M E, Crowther D, Miele G. Hematopoietic Lineage Transcriptome Stability and Representation in PAXgene Collected Peripheral Blood Utilising SPIA Single-Stranded cDNA Probes for Microarray. Biomark Insights. 2008; 3:403-417.

Example 6—Spexin Dose Response Experiment in C57BL/6J DIO Mice

The effect of Spexin on weight loss will be investigated by daily IP injections of Spexin (about 3 µg/kg/day, about 10 µg/kg/day, about 30 µg/kg/day, and about 100 µg/kg/day) in Diet-Induced-Obesity (DIO) mice, where all of the known signaling systems are intact. Both normal weight and DIO mice will be tested for circulating levels of Leptin, insulin, and Spexin.

Pharmaceutical grade Spexin (a 14 amino acid peptide normally circulating in mice and humans) has been synthesized by conventional solid-state chemistry, and purified to >95% identity by Phoenix Pharmaceuticals (Burlingame, Calif.). This agent will be solubilized in 1× sterile saline (pH 7.4) at four different concentrations, so that doses of 10 µg/kg/day/QD, 50 µg/kg/day/QD, 250 µg/kg/day/QD, or 500 µg/kg/day/QD can be administered to 5 mice in each dose group. Final total doses of 10 ng/day, 50 ng/day, 250 ng/day, or 500 ng/day, will be delivered in volumes of 0.2 ms/dose/day via IP injections. For example, to deliver 10 ng total per day, two daily injections of 5 ng each will be administered IP (stock concentrations of Spexin will be 25 ng/ml). Alternatively, to deliver 10 ng per day, a daily injection of 10 ng can also be administered IP (stock concentrations of Spexin will be 50 ng/ml). The doses are calculated to result in physiologic levels of Spexin with some latitude introduced to allow for the rough estimates based on the current data available and the preliminary characterization of Spexin's basic pharmacologic parameters.

C57BL/6J DIO mice from Jackson Labs, whose average weight is approximately 30% greater than their age-matched controls at 17 weeks, will be acclimated to laboratory conditions prior to initiating the Spexin dosing studies.

Experimental Outlines

Spexin Dose-Response Experiment. The objective of this experiment will be to determine dose(s) of Spexin to be used in subsequent studies. The effects of Spexin will be followed by daily monitoring of body weights, food and water consumption, and their plasma will be assayed for Leptin, insulin and Spexin periodically.

| Mouse Strain | Number |
| --- | --- |
| DIO/60% HFD (untouched neg controls) | 5 |
| DIO/60% HFD (saline injection neg controls) | 5 |
| DIO/60% HFD (5 animals @ at each of 4 different doses) (doses = 10, 50, 250, and 500 ngs Spexin/injection/QD) | 20 |
| C57BL/6J (saline injection neg controls) | 5 |
| C57BL/6J (Spexin at 30 ngs/injection/QD) | 5 |
| Total | 40 |

Spexin Dosing in Various Murine Models of Obesity.

| Mouse Strain | Saline | Spexin | Leptin (as + control) |
| --- | --- | --- | --- |
| C57BL/6J background as controls | 6 | 6 | |
| DIO/60% HFD | 6 | 6 | |
| ob/ob | 6 | 6 | |
| ob/ob treated with leptin as positive control | | | 6 |
| db/db | 6 | 6 | |
| Fat | 6 | 6 | |
| Tubby | 6 | 6 | |
| Additional animals for dose-adjusted experiments | 6 | 6 | |
| sub-totals | 42 | 42 | 6 |
| Total | | 90 | |

Grand total = 130 animals

The studies described herein will be expanded by measuring and/or analyzing Spexin and its actions on the hypothalamus via traditional neuroscience techniques, such as immunohistochemisty, and by functional imaging, such as PET scans, of living animals in the absence or presence Spexin, as well as in the absence or presence Spexin under a variety of physiological conditions.

Example 7—Spexin Experiment in C57BL/6J DIO Mice

Obesity has reached epidemic proportions in adults and children in the US, and is linked to a myriad of co-morbidities, including insulin resistance, the metabolic syndrome, type 2 diabetes, and fatty liver disease. Whole human genome microarrays were used to identify individual genes and biological pathways whose expression is altered in omental and subcutaneous fat samples from obese patients. The gene with the most dramatic under expression in obese fat was Spexin, a recently identified peptide of unknown function, the expression of which has never been reported in fat. The data indicate that Spexin message is highly expressed in omental and subcutaneous fat from normal weight human subjects, but is dramatically reduced (~15-fold) in obese fat samples (p<0.00292). Serum Spexin peptide levels are approximately 10× lower in obese than in non-obese patients (p<0.0002), and Spexin and Leptin levels in the serum of obese patients and normal weight controls demonstrate a strong negative correlation (r=−0.92). These results in human patients and parallel findings in high fat diet-fed (HFD) obese mice indicate that Spexin plays a role in the regulation of food consumption, energy metabolism and body weight.

Figure 19:
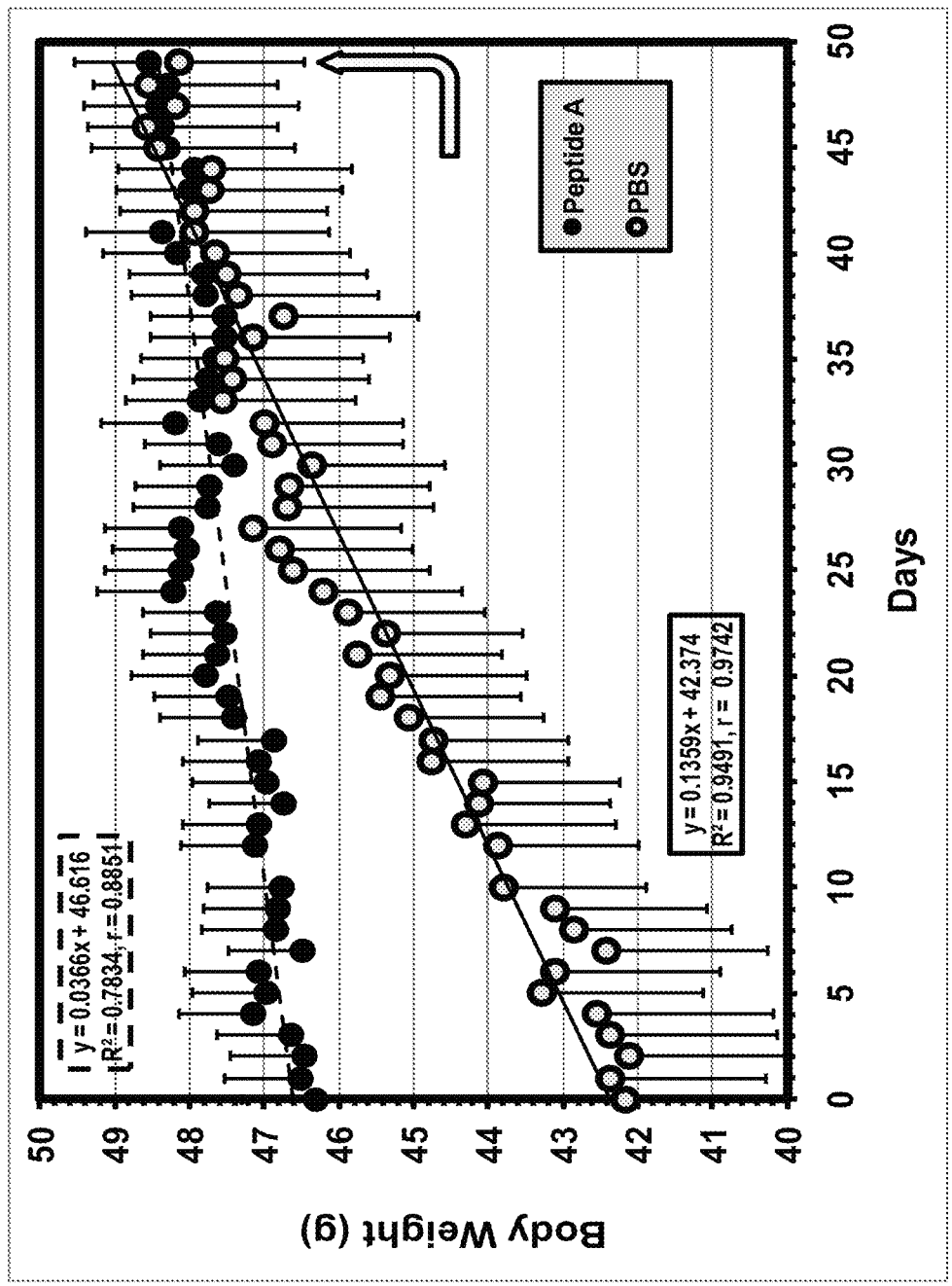
FIG. 19 is a graph showing a comparison of 2 groups of obese, high fat diet (HFD)-fed C57BL/6J mice. One group, with a mean starting weight of 42 grams, was treated with daily intraperitoneal injections of phosphate buffered saline (PBS) plus 0.05% bovine serum albumin (BSA). The second, with a mean starting weight 46 grams, received daily Spexin (Peptide A) injections in 1×PBS plus 0.05% BSA at a dose predicted to minimize weight gain or maintain body weight. The PBS group continued rapid weight gain; the Spexin group gained weight much more slowly. The weight curves of the 2 groups crossed at 6 weeks of treatment. Animals were sacrificed at 7 weeks, at which time the mean weights of the two groups were not different.
Figure 20:
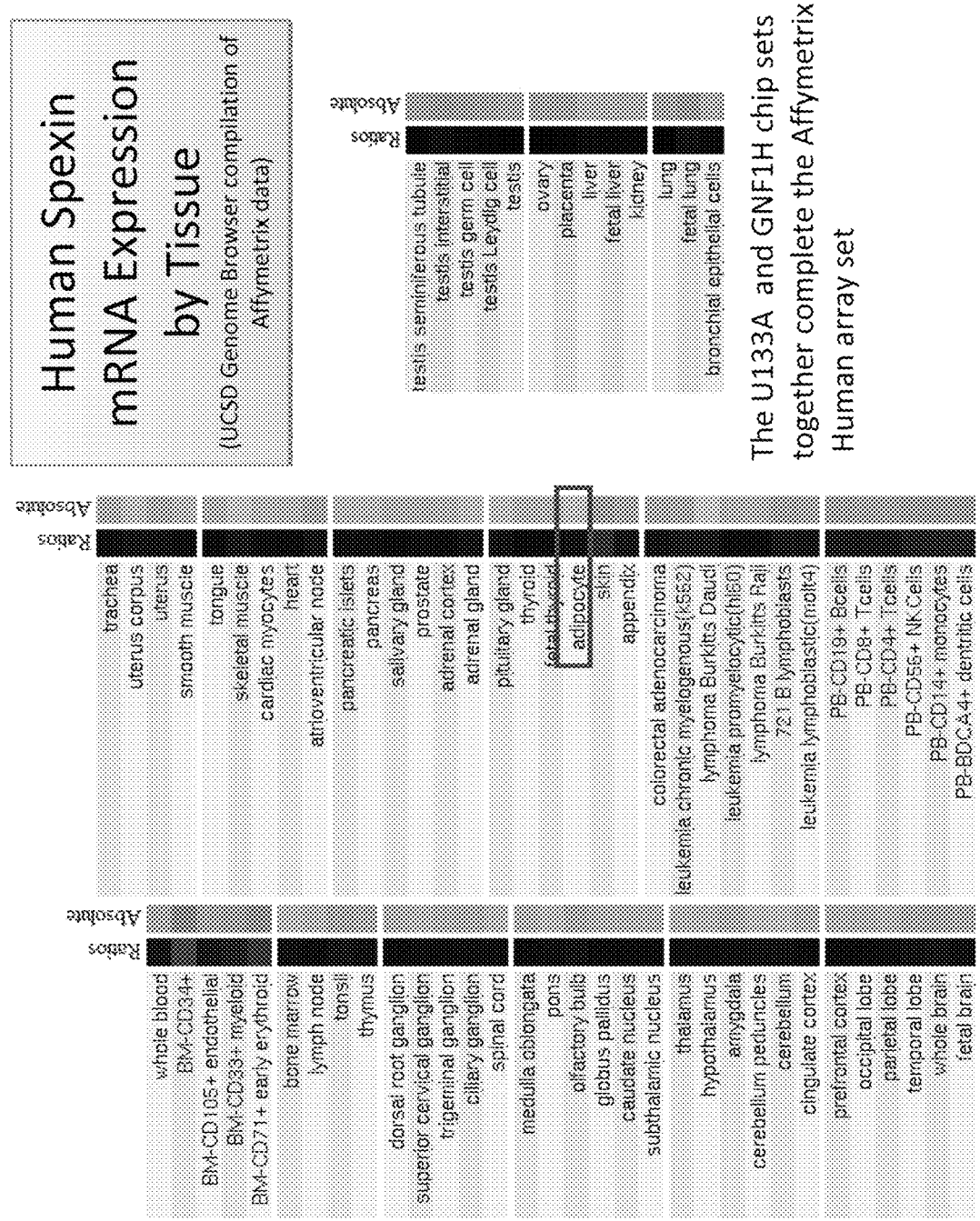
FIG. 20 is a schematic of human Spexin mRNA expression by tissue. A compilation of Affymetrix human gene expression data from the UCSD Genome Browser indicates that expression of Spexin is limited to a few tissues (for example, CNS nuclei, skeletal muscle, Burkits's lymphoma [Daudi], and adipose tissue). Spexin expression is low in most human tissues by Affymetrix microarray analysis.

Spexin was administered at 10 µg/kg body weight/day IP to obese HFD-fed C57BL/6J mice. The injections reduced food consumption and body weight in mice with HFD-induced obesity, while the corresponding control HFD-mice, receiving only vehicle, continued to gain weight. It was previously shown that regulation of adipocyte LCFA uptake is an important control point for body adiposity, Spexin was subsequently administered for 7 weeks at a dose to maintain body weight in obese HFD-fed mice (FIG. 19).

Example 8—Effect of Spexin on Adipocyte LCFA Uptake

Multiple studies suggest that regulation of adipocyte LCFA uptake is an important control point for body adiposity, e.g. [S1-S3]. To study the potential role of Spexin in this process, epididymal fat pads were removed from Spexin-treated DIO mice, and [3H]-oleic acid uptake kinetic constants in isolated adipocytes were determined by standard methods [S1-S5, S10, S12-S15] The Vmax for facilitated LCFA uptake in Spexin-treated mice, 61±9 pmol/sec/50,000 cells, was only 28% of that of the control mice (211±60 pmol/sec/50,000cells, p=0.047). In other studies, adipocyte suspensions were prepared from untreated DIO mice. Paired aliquots were incubated with either PBS (controls) or in PBS/Spexin (20 ng/mL). Two preparations of Spexin were used: (1) Phoenix Pharmaceuticals—a commercial supplier, and (2) Ferring Research Institute, (custom synthesis). Both were >99% pure by HPLC and ID'd by LC/MS. Uptake results are shown in FIG. 21. Short incubations in vitro (2 hrs) resulted in a significant down-regulation of adipocyte LCFA uptake, with nearly identical results with both Spexin preparations, indicating that Spexin can inhibit weight gain in part by downregulation of LCFA uptake in adipocytes. Further studies are examining the time-dose-response characteristics of Spexin on adipocyte LCFA uptake, and expression of LCFA transporter genes in this system by both qRT-PCR and Western Blot.

REFERENCES

S1. Fan, X., M. W. Bradbury, and P. D. Berk, *Leptin and insulin modulate nutrient partitioning and weight loss in ob/ob mice through regulation of long-chain fatty acid uptake by adipocytes.* J Nutr, 2003. 133(9): p. 2707-15.

S2. Berk, P. D., et al., *Selective up-regulation of fatty acid uptake by adipocytes characterizes both genetic and diet-induced obesity in rodents.* J Biol Chem, 1999. 274(40): p. 28626-31.

S3. Petrescu, O., et al., *Long-chain fatty acid uptake is upregulated in omental adipocytes from patients undergoing bariatric surgery for obesity.* Int J Obes (Lond), 2005. 29(2): p. 196-203.

S4. Stump, D. D., X. Fan, and P. D. Berk, *Oleic acid uptake and binding by rat adipocytes define dual pathways for cellular fatty acid uptake.* J Lipid Res, 2001. 42(4): p. 509-20.

S5. Zhou, S., Stump D, Kiang, C L, isola L M, and Berk P D, *Mitochondrial aspartate aminotransferase expressed on the surface of 3T3-L1 adipocytes mediates saturable fatty acid uptake.* Proc Soc Exp Biol Med, 1995. 208: p. 263-270.

S10. Walewski, J., Ge, F, Gagner, M, Inabnet, W B, Pomp, A, Branch, A D, Berk, P D, *Adipocyte accumulation of long chain fatty acids in obesity is multifactorial, resulting from increased fatty acid uptake and decreased activity of genes involved in fat utilization.* Obesity Surgery (In press), 2010.

S11. Considine, R. V., et al., *Serum immunoreactive-leptin concentrations in normal-weight and obese humans.* N Engl J Med, 1996. 334(5): p. 292-5.

S12. Ge, F., et al., *Insulin- and leptin-regulated fatty acid uptake plays a key causal role in hepatic steatosis in mice with intact leptin signaling but not in ob/ob or db/db mice.* Am J Physiol Gastrointest Liver Physiol, 2010. 299(4): p. G855-66.

S13. Petrescu, O., Fan, X Q, Bradbury, M W and Berk, P D, *Selective regulation of long chain fatty acid uptake across adipocyte plasma membranes is a control point for body adiposity.* Gastroenterology, 2003: p. 124-A70.

S14. Stremmel, W. and P. D. Berk, *Hepatocellular influx of [14C]oleate reflects membrane transport rather than intracellular metabolism or binding.* Proc Natl Acad Sci USA, 1986. 83(10): p. 3086-90.

S15. Zhou, S., Sorrentino, D, Stump, D, Potter, B, and Berk, P D, *Adipocyte Differentiation in 3T3-L1 Fibroblasts Is Associated with Expression of A Plasma-Membrane Fatty-Acid Binding-Protein.* Hepatology, 1990(12): p. 897.

Example 9—Effect of Spexin on 24 Hour Feeding Behavior in DIO Rats

Obese adult female Wistar rats (n=4/group) received single daily injections (sc) of vehicle or Spexin (35 μg/kg BW). Body weights and food intake were measured daily. Average daily food intake (FIG. 22A) and body weight (FIG. 22B) for each group was recorded for each 24 hr period. 24 hr food intake was reduced in the Spexin treated animals (dark circles) by Day 3. The Spexin-treated rats reduced their cumulative food intake over Days 3 and 4 by 31.5%. This effect persisted well beyond the immediate treatment period, and was apparent out to Day 7. Spexin treatment also led to a reduction in body weight, which showed a delay in onset (starting on Day 4, and with considerable persistence of the effect well beyond the treatment period, out to at least Day 15.

Figure 23:
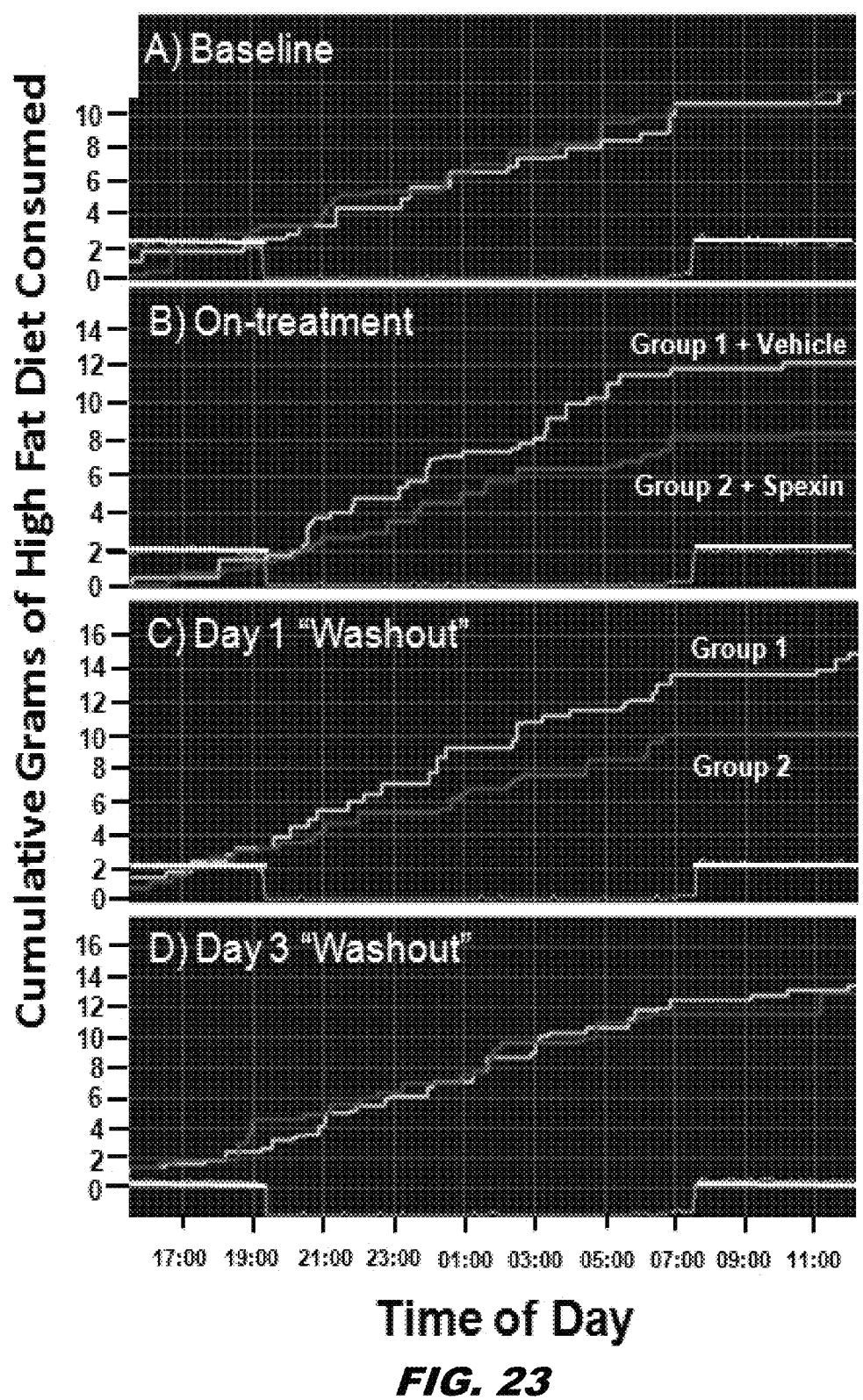
FIG. 23 are graphs showing that spexin injections reduce the total amount of food consumed by DIO rats over a twenty-four hour period.

A more detailed analysis of hourly feeding behaviors, including 1) number of "meals" during a 24 hr light/dark cycle, and 2) meal duration and incidence were continuously recorded by a BioDaq Food Intake Monitoring System (FIG. 23). Pre-treatment baselines (FIG. 23A), on-treatment responses (FIG. 23B), early (FIG. 23C) and late (FIG. 23D) "wash-out" periods are presented. Horizontal white lines indicate "lights on". As expected, the vast majority of feeding occurs during "lights off" since rats are nocturnal feeders. At baseline, the two groups of animals demonstrated essentially identical feeding behaviors. After two days of treatment, the Spexin-dosed animals (Group 2+Peptide A (Spexin)–red line) demonstrated a clear reduction in food consumption during the normal feeding period (lights out; 19:00 to 07:00 hours) of Day 3, and normal cessation of feeding during the light period (horizontal white bars) of Day 4. It is noteworthy that the temporal (light/dark) feeding pattern and meal frequency during this normal feeding period remained normal in the peptide-treated group. What was reduced was the meal size and duration (both smaller). No indications of nausea or taste aversion behaviors were seen in this study. Without being bound by theory, Spexin is a potent natural satiety-inducing agent.

Example 10—Effects of Spexin on 24 hr Metabolic Parameters in DIO Mice

DIO mice were dosed with Spexin (35 μg/kg i.p.) daily for 19 days while individually housed in metabolic chambers. Oxygen consumption, CO2 output, the respiratory exchange ratio (RER), and locomotor activity were monitored continuously using a CLAMS (Columbus Instruments) open-circuit indirect calorimetry system. The calorimetry cage data show: 1) a tendency to fail to maintain adipose weight over the 2 wk period (see FIG. 24B inset; N=4/group); 2) that Spexin significantly reduces RER toward fat oxidation (FIG. 24A), particularly at night, predominantly by blocking typical night-time elevation in RER toward carbohydrate (typical night-time fuel utilization is carbohydrate, as this is when rodents typically eat); and 3) that Spexin increases locomotor activity (Z=rearing (z plane) and TOTAL (=x,-y and Z planes summed) relative to vehicle treated DIO controls (FIG. 24B).

The increased locomotor activity in the Spexin treated animals can be either a compensatory response to the failure to maintain body weight, or an indication of increased fat oxidation. The latter could reflect Spexin-mediated diversion of LCFA away from storage in adipocytes to tissues such as liver, muscle and heart, where they are oxidized. These intriguing data indicate that Spexin can induce "fasting like" metabolism in DIO animals.

Example 11—Spexin is a New Human Peptide that Reduces Adipocyte Uptake of Long Chain Fatty Acids and Causes Weight Loss in Mice Obesity and obesity-related disorders have undergone a worldwide epidemic over the past 5 decades, and are expected to be one of the greatest challenges to the public health in the 21st century. The U. S. in particular is experiencing an obesity epidemic with profound consequences [P1-P4], e.g. ~300,000 deaths annually [P5, P6], a decrease in life expectancy [P7], and enormous health care costs [P8-P10]. Obesity is linked to increased prevalences of non-insulin-dependent diabetes mellitus, atherosclerotic cardiovascular disease, fatty liver disease, stroke, osteoarthritis, sleep apnea, and certain cancers, all leading to excess morbidity and mortality in this patient population [P11].

Virtually by definition, obesity represents the excess accumulation of long chain fatty acids (LCFA) as triglycerides (TG) in white adipose tissues (WAT), which play a major role in energy storage throughout the body. In addition, WAT also function as "endocrine organs" [P12] by secreting unique profiles of adipokines, a diverse collection of more than 50 cytokines, chemokines, and hormone-like factors [P13] which contribute to the maintenance of energy homeostasis in the healthy state. While not expressed exclusively by WAT, some locally secreted adipokines have been shown to affect appetite, satiety, and glucose and lipid metabolism [P12-P15]. The actions of many of these adipokines are ultimately integrated to regulate glucose and energy metabolism, LCFA uptake and storage, and insulin activity via both paracrine and endocrine mechanisms.

A central characteristic of the obese state is that the delicate, complex and integrated adipokine networks in OWAT lose their normal regulatory mechanisms, thereby adversely affecting the homeostatic endocrine balance of WAT. A serious consequence of this alteration in endocrine balance is the disruption of healthy adipocyte metabolism, further aggravating the pathologic storage of excess energy as lipids. The pathophysiologic significance of dysregulated OWAT signaling networks, a key consequence of the obese state, is only beginning to be understood [P12-P15].

Microarray studies ongoing in the inventors' laboratory since 2008 comparing gene expression in obese vs non-obese human omental and subcutaneous WAT have identified both individual genes, and biological pathways whose components are significantly dysregulated in obese human WAT [P16]. Studies using Codelink Human Whole Genome microarrays, with probes for ~55K genes and ESTs, identified ~3,500 genes and ESTs that exhibited significant differences in expression (p<0.05, without correction). Studies identified Ch12: orf39 as the mRNA with the greatest difference in expression, down 14.9-fold in obese WAT. This gene appeared to encode a peptide, and probably a secreted peptide. When the product of the gene expressed from Ch12: orf39 was examined, it was identical to Spexin, a new peptide very recently identified by Mirabeau et al using a Markov modeling algorithm [P17].

The finding that Sepxin was the single most down-regulated gene in obese human fat, coupled with the observations by Mirabeau et al that Spexin induced muscarinic-like contractions in stomach smooth muscle in an in vitro assay [P17], led the inventors to conclude that Spexin can normally function as an adipocyte-expressed satiety factor, and that the lack of Spexin expression by obese WAT led to the loss of a key adipokine involved in the regulation gut motility, food intake, energy metabolism and long chain fatty acid (LCFA) uptake and storage into adipocytes. Therefore, the biological role of Spexin in rodent models of diet-induced obesity was examined.

Methods

Patients. Patient undergoing clinically indicated abdominal laparoscopic surgical procedures consented to removal of omental and sub-cutaneous fat samples for studies of LCFA transport, molecular studies, and a venous blood sample for the measurement of circulating adipokines. Obese patients were undergoing bariatric surgical procedures, and the non-obese patients were undergoing other clinically indicated laparoscopic procedures at either the Weill Cornell or Columbia Presbyterian campuses of New York Presbyterian Hospital. The protocols, consent documents, and procedures for these studies were approved by the individual Institutional Review Boards of the Columbia University and Weil Cornell Medical Centers.

Studies of LCFA Uptake Kinetics

Materials. 9,10-[3H]-Oleic acid (OA) was purchased from NEN Life Science Products, type I collagenase for adipocyte isolation from Sigma (St. Louis, Mo., USA), fatty acid free bovine serum albumin (BSA) from Boehringer Mannheim (Indianapolis, Ind., USA).

Isolation of Adipocytes from Human Fat Samples and DIO Mice. Adipocytes from human omental and subcutaneous fat biopsies [P18] and from epididymal fat pads of DIO C57BL/6J mice (18 weeks of age) [P19, P20] were prepared by collagenase digestion according to established protocols. Adipocyte suspensions were maintained at room temperature in Dulbecco's modified Eagle's medium (DMEM) for up to 3 h until warmed to 37° C. for use [P18, P21], and met established viability criteria [P18,P 21]. After isolation, adipocytes were sized by direct light microscopy as described [P22].

Studies of LCFA Uptake

The initial rate of [3H]-OA uptake by both human and mouse adipocytes was determined by rapid filtration [P16, P18]. In brief, known numbers of cells in suspension in 100 μl of DMEM were added to five tubes, each of which contained 240 μl of DMEM containing 500 μM BSA and [3H]-OA at one of five different OA:BSA molar ratios (v) ranging from 0.25:1 to 2.5:1. The tubes were incubated for 0-30 s at 37° C., during which LCFA uptake was stopped at four pre-determined times at which cells were filtered and washed, and bound tracer was counted by liquid scintillation spectrometry [P18, P21].

Computations and Fitting of Kinetic Data. The slopes of the respective cumulative uptake versus time curves at each value of v, representing initial uptake velocity (Vo), were calculated from the four times samples obtained in triplicate over the initial 30 secs of incubation, since adipocyte uptake of [3H]-OA is linear over this timeframe [P18, P21]. The unbound oleate concentration ([OAu]) in each test solution was calculated from the OA/BSA molar ratio (v) [P22], using the LCFA/BSA binding constants of Spector et al [P23].

Initial [3H]-OA uptake velocities at each of the 5 values of [OAu] studied were fitted by computer to the sum of a saturable plus a linear function of [OAu], according to the equation: Equation 1: $Vo([OAu])=(Vmax \cdot [OAu])/(Km+[OAu])+k \cdot [OAu]$, where $Vo([OAu])$=initial [3H]-OA uptake velocity (pmol/sec/50,000 cells) at unbound oleate concentration [OAu] (nM); Vmax and Km are the maximum uptake velocity (pmol/sec/50,000 cells) and the concentration at which initial uptake velocity is ½ maximum (nM); and k is the rate constant for non-saturable uptake (μl/50,000 cells/sec). Data fitting was accomplished with the SAAM II program of Berman and Weiss [P23].

Statistical Considerations. Values for physiologic variables are reported as the mean±standard error were calculated according to standard methods of descriptive statistics [P24]. The significance of differences between groups was assessed with Student's two-tailed t test with p≤0.05 being considered significant.

Whole Human Genome Microarray Gene Expression Studies

Gene expression in omental and subcutaneous fat samples from obese versus normal weight subjects was compared by whole genome microarray analysis. Paired omental and subcutaneous fat biopsies were collected during laparoscopic surgical procedures and stored at −80° C. in RNAlater. Biotin-labeled cRNAs were generated using standard protocols, and hybridized overnight to Codelink Human Whole Genome microarrays (Applied Microarrays, Tempe. Ariz.), as previously described in detail [P16]. Median normalized gene expression data (arbitrary expression units) were analyzed using the GeneSifter Data package. Statistical treatment of the results was as reported earlier [P16, P24].

Quantitative immunoassays. Quantitative immunoassays to determine circulating levels of Spexin by competitive EIA (Cat #EK-023-81) and human Leptin by antigen capture ELISA (Cat #EK-003-12) were purchased from Phoenix Pharmaceuticals (Burlingame, Calif.), and performed according to the manufacturer's instructions. Human serum samples were diluted 1/20 (Spexin) and 1/5 (Leptin) in 1× assay buffer. After incubation with appropriate antibodies, plates were washed and incubated with 100 μL of TMB. When appropriate color development was noted, reactions were stopped by adding an equal volume of 2N HCL. Plates were read at 450 nm, and OD values were converted to ng/mL of serum based on the standard curves incorporated into each assay.

Metabolic Assessments DIO Mice

C57BL/6J mice with diet induced obesity (DIO) were obtained from Jackson Labs (Bar Harbor, Me., USA). DIO mice were maintained ad lib on a high fat diet (D12492, Research Diets, New Brunswick, N.J.) which provide 60% of the total calories consumed as fat.

After adaptation, 18-20 week old DIO mice were dosed with Spexin (35 µg/kg i.p.in 1×PBS) daily for 19 days while individually housed in metabolic chambers. Individual body weights, twenty-four hour locomotor activity (ambulation in the X, Y and Z planes), oxygen consumption, CO2 output, and the respiratory exchange ratio (RER), were monitored continuously using a CLAMS (Columbus Instruments, Columbus, Ohio) open-circuit indirect calorimetry system [P25, P26].

24 hr Feeding Behavior in DIO Rats

Obese (DIO) adult female Wistar rats (n=4/group) received single daily injections (sc) of vehicle or Spexin (35 µg/kg BW). Individual body weights and food intake were measured and recorded daily, and the average food intake and body weight for each group was recorded for each 24 hour period. For a more detailed analysis of hourly feeding behaviors, number of feeding events or "meals" during a 24 hour light/dark cycle, and frequency and durations of individual meals were continuously recorded via a BioDaq Food Intake Monitoring System (New Brunswick, N.J.).

Conditioned Taste Aversion Studies in Rats

Conditioned taste aversion studies were conducted using adult female Wistar rats according to established protocols [P27-P29]. For training, rats were water but not food deprived for 20 hrs (1800-1400 hrs the following day), then offered a single bottle of water ad libitum for 20 min. Training sessions took place on 2 days of each week, spaced at 3-4 day intervals, to allow recovery of normal food intake and body weight. A total of 7 training sessions were conducted, by which time all animals had learned to drink promptly when fluid was offered. Testing was initiated on the same schedule, with 0.1% sodium saccharin rather than water as the available liquid. On test days 1-3 groups of rats were injected ip with either physiological saline, spexin (70 µg/kg body weight), or LiCl (63.5 mg/kg body weight). All groups experienced their first saccharin exposure and injection on test day 1. Spexin and LiCl were mixed in 1×PBS in concentrations of 7 µg/ml and 0.15M, respectively, and a solution dose of ml injected=1% of body weight (g) was used for all injections. No injections were administered on the final test day. A mild dose of LiCl was used over repeated test sessions to generate a slowly developing conditioned taste aversion. This data was used as the positive control comparator arm to assess the effects of repeated injections of Spexin.

Results

Gene expression in omental and subcutaneous fat samples from obese versus normal weight subjects was compared by whole genome microarray analysis [P30]. Median normalized gene expression ratios for each probe, representing 55K known genes and ESTs, were compared by log-log plot (FIG. 1). Of all the genes and ESTs demonstrating dysregulated expression in obese human WAT, Ch12, ORF39 (Spexin) demonstrated the largest change, a 14.8-fold drop in expression in obese WATs (p=0.00292 by two tailed t-test).

Figure 25:
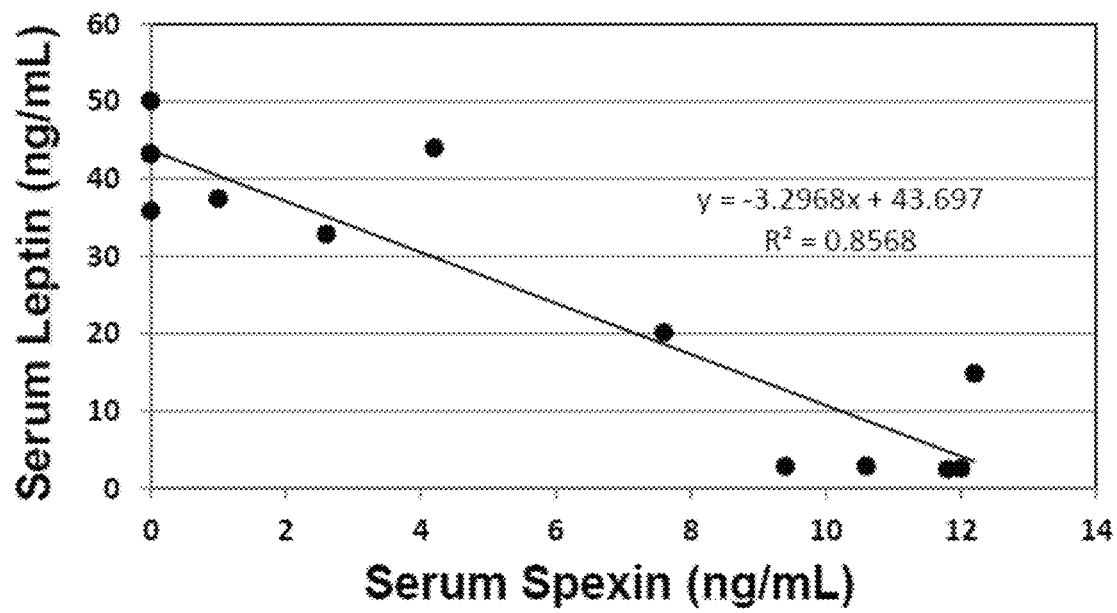
FIG. 25 is a plot showing a negative correlation between Spexin and Leptin concentrations in human serum. Paired Spexin (abcissa) and Leptin (ordinate) serum concentrations for individual patients (6 obese, 6 normal weight) were measured by immunoassays (EIA and ELISA, respectively; Phoenix Pharmaceuticals, Burlingame, Calif.) according to the manufactuer's instructions. A strong negative correlation in serum concentrations is seen between the two adipokines ($r=-0.9256$).

Spexin and Leptin in Human Serum. Human serum samples from obese and non-obese patients were assayed for both circulating Spexin and Leptin concentrations by commercial immunoassays (EIA and ELISA, respectively). The mean concentration of the Spexin peptide in the serum of obese patients was found to be approximately 1/10th that of Spexin in normal weight subjects by immunoassay (FIG. 5: p<0.0002, by 2 tailed t test), in reasonable agreement with the 15-fold difference in Spexin gene expression found in WATs from obese patients. Circulating Leptin averaged 8.53±7.55 ng/mL in serum from non-obese patients, and 37.42±11.56 ng/mL in serum from obese patients (p<0.01, 2 tailed t-test). Without being bound by theory, the strong negative correlation (r=−0.92) between Leptin and Spexin in the serum of obese patients and normal weight controls (FIG. 25) indicates that these peptides play antagonistic roles in the normal regulation of hunger, satiety, body adiposity and weight, where they serve as opposing components of a negative feedback loop.

Figure 26:
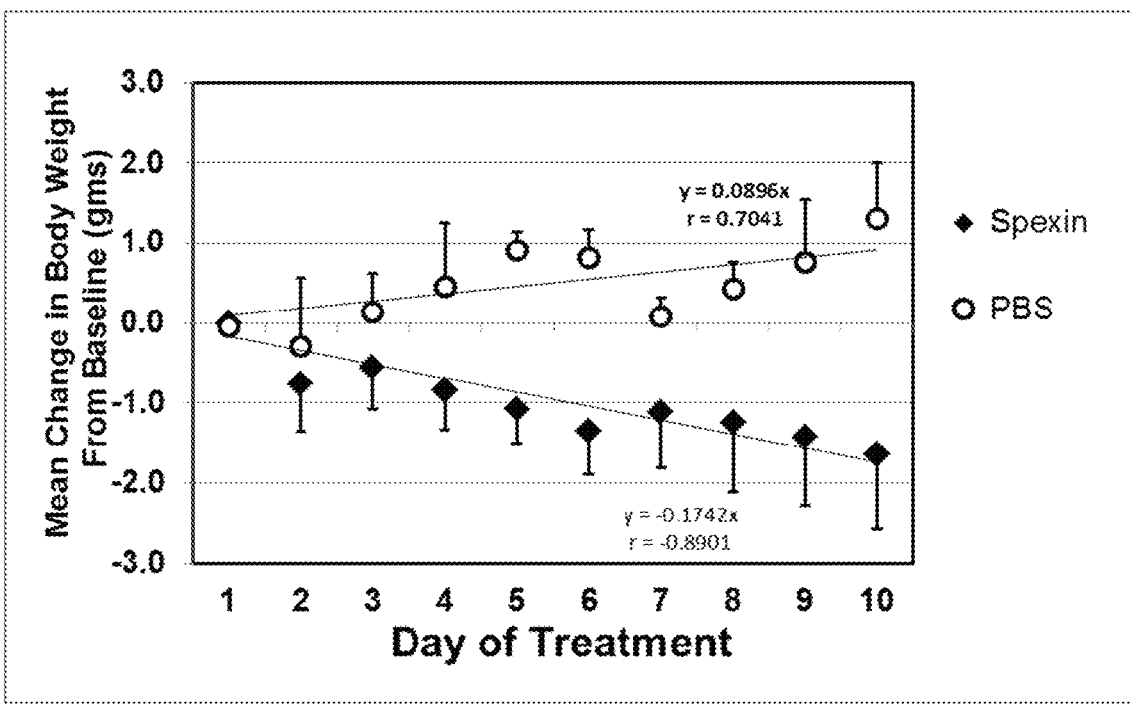
FIG. 26 is a plot showing daily intraperitoneal injections of spexin that result in weight loss in DIO mice. All DIO mice were maintained on ad lib high fat diet (D12492, Research Diets, New Brunswick, N.J.). Body weights, plus food and water intake were measured daily. Data are mean change from baseline weight±SD, (n=5/group). Day 1 is the first day of injection. Adult male C57BL/6J DIO mice (Jackson Labs) received daily injections of Spexin (25 µg/kg IP in 0.1 mL of 1×PBS). All 5 animals lost weight progressively (Slope=$-0.1742$ g/day, $r=-0.8901$). Age-matched DIO controls received daily vehicle injections IP, and continued to gain weight over the next 10 days on the high-fat diet (Slope=$+0.0896$, $r=0.7041$).

Effect of exogenous Spexin on body weight in C57BL/6J mice with DIO. To test that Spexin is a satiety factor that helps to regulate feeding behavior, Spexin was administered to DIO mice by daily IP injections for 10 days. Food and water consumption was measured daily. Control animals received daily IP injections of equal volumes of 1×PBS. At 10 µg/kg; (IP QD), all mice injected with Spexin lost weight over the course of the experiment (average daily weight loss=~0.17 gms/day) (FIG. 26), due to the Spexin animals consuming approximately 20% less high-fat diet per day. Controls receiving 1×PBS continued to gain weight on the HFD (FIG. 26).

Figure 27:
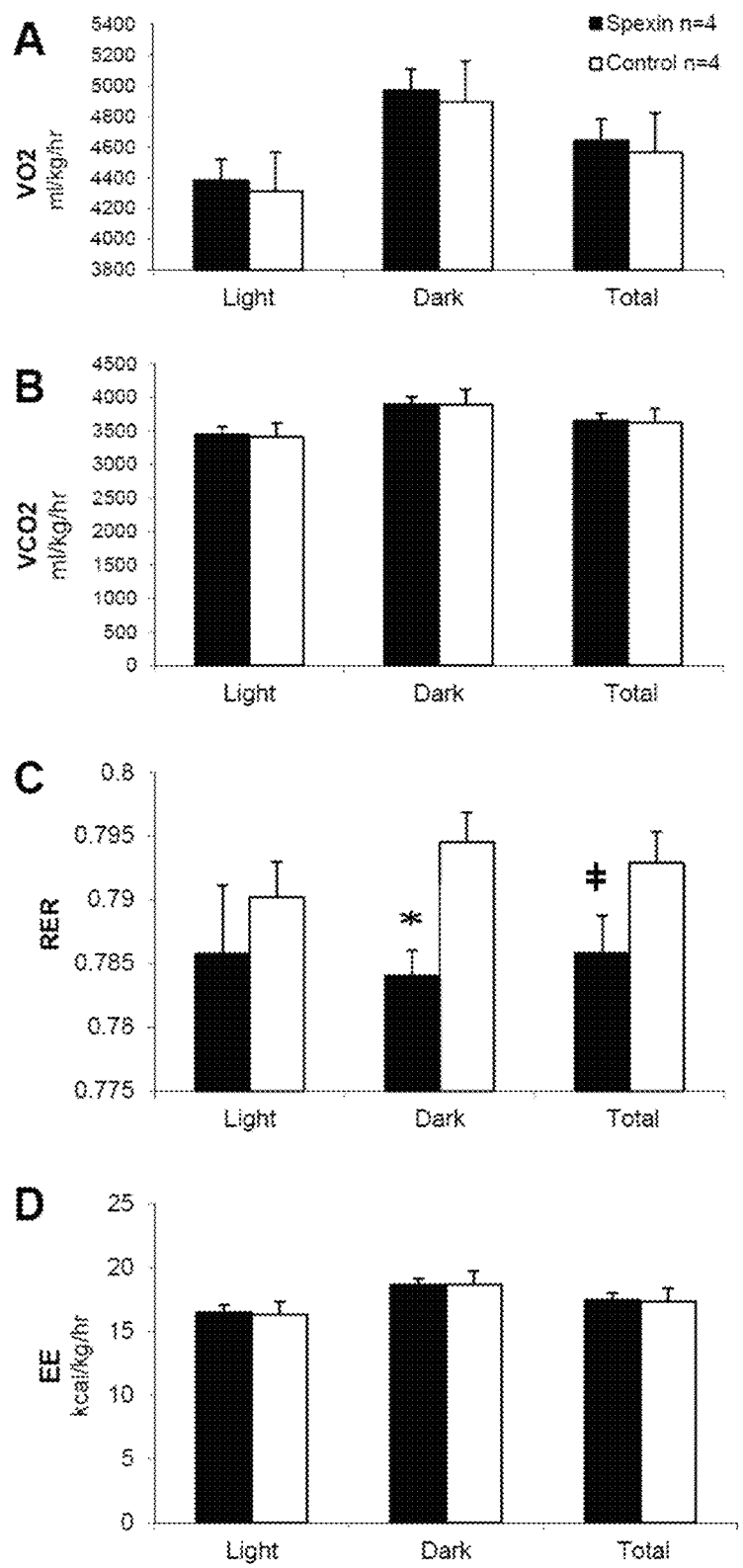
FIG. 27 shows bar graphs of the effects of spexin on metabolic parameters in DIO mice. After adaptation, DIO mice (N=4/group) were dosed with Spexin (35 µg/kg i.p.) daily for 19 days while individually housed in metabolic chambers. Key parameters, including twenty-four hour oxygen consumption (FIG. 27A), CO2 output (FIG. 27B), the respiratory exchange ratio (RER) (FIG. 27C) (*=$p<0.05$, ‡=$0.10>p>0.05$), and energy expenditure (EE) (FIG. 27D) were monitored continuously using a CLAMS (Columbus Instruments) open-circuit indirect calorimetry system.

Effects of Spexin on Metabolic Parameters in DIO Mice. After adaptation to the metabolic cages, individually housed mice were monitored for O2 and CO2 consumption, and the respiratory exchange ratio (RER), and energy expenditure (EE) were measured and determined over the 19 days of Spexin treatment. Time frames that were monitored included the Light (12 hours lights on), Dark (12 hours lights off) and Total (24 hours/day) periods. VO2 consumption (FIG. 27A) was greater during the Dark cycle (lights off) than during the Light period when the mice are less active, however the Spexin-treated animals demonstrated only a modest, non-significant increase in VO2 consumed through the Light, Dark and total periods. VCO2 consumption (FIG. 27B) was similar between the Light and Dark cycles, and virtually identical in both the Spexin and control animals. The cumulative RER results (FIG. 27C) show different patterns between the Light and Dark cycles, and between the treated and controls. The control mice have a modestly higher RER during the Dark versus the Light cycle, and the Spexin-treated animals have significantly lower RERs compared to the control mice (0.784+/−0.002 versus 0.795+/−0.002, p=0.006, respectively) during the Dark cycle. The total RERs were also lower in the Spexin-treated animals, although this difference was not significant (p=0.056). Total energy expenditure (EE) showed little difference in any comparison (FIG. 27D). The total kcal/kg/hr burned increased slightly during the Dark period versus the Light period, however the total amounts of energy consumed during each period were almost identical between the Spexin-treated animals and the controls.

Detailed recordings of the calorimetry cage data over a representative 24 hr period during Spexin treatment show that: 1) Spexin increases locomotor activity (Z=rearing (z plane) and TOTAL (=x-y and Z planes summed) relative to vehicle treated DIO controls (FIG. 24B), and 2) that Spexin significantly reduces RER toward fat oxidation (FIG. 24A), particularly at night, predominantly by blocking typical night-time elevation in RER toward carbohydrate (night-time fuel utilization is primarily carbohydrate).

Figure 24:
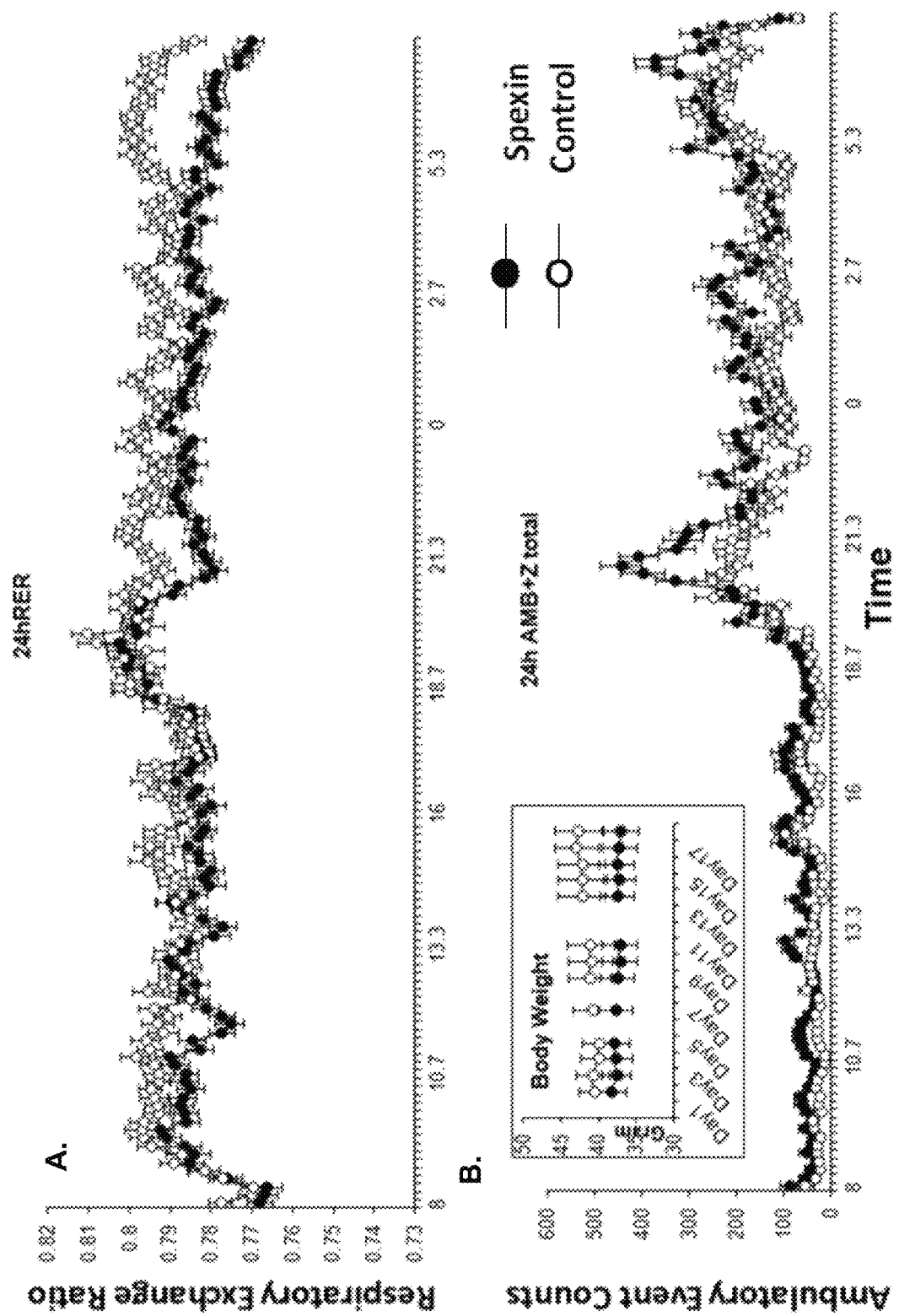
FIG. 24 shows plots of the effects of spexin on 24 hr metabolic parameters in DIO mice. Twenty-four hour locomotor activity (ambulation in the X, Y and Z planes) (Panel A), oxygen consumption, $CO_2$ output, and the respiratory exchange ratio (RER) (Panel B) were monitored continuously using a CLAMS (Columbus Instruments) open-circuit indirect calorimetry system. Body weights were recorded daily (inset). Elevations in ambulation (especially in the Z plane, increased rearing), and reductions in the RER reach significance during the Dark cycle.

Body weights were recorded throughout the 19 days of the experiment (inset FIG. 24). The vehile treated animals continued to gain weight over the course of the experiment (y=0.1625x+39.801 r=0.9262), while the Spexin-treated animals lost weight over the same period (y=−0.0438x+38.005, r=−0.7318).

Spexin inhibits LCFA uptake into isolated adipocytes. Multiple studies indicate that regulation of adipocyte LCFA uptake is an important control point for body adiposity, e.g. [P18, P19, P31]. To study the potential role of Spexin in this process, epididymal fat pads were removed from Spexin-treated DIO mice, and [3H]-oleic acid uptake kinetic constants in isolated adipocytes were determined by standard methods [P18-P20, P30-P36]. The Vmax for facilitated LCFA uptake in Spexin-treated mice, 61±9 pmol/sec/50,000 cells, was only 28% of that of the control mice (211±60 pmol/sec/50,000 cells, p=0.047). In other studies, adipocyte suspensions were prepared from untreated DIO mice. Paired aliquots were incubated with either PBS (controls) or in PBS/Spexin (20 ng/mL). Two preparations of Spexin were used: (1) Phoenix Pharmaceuticals—a commercial supplier, and (2) the Ferring Research Institute, (custom synthesis). Both were >99% pure by HPLC and ID'd by LC/MS. Short incubations in vitro (2 hrs) resulted in approximately a 40% down-regulation of adipocyte LCFA uptake, with nearly identical results with both Spexin preparations, indicating that Spexin can reduce lipid accumulation in adipose tissues in part by down-regulation of LCFA uptake into adipocytes.

Figure 28:
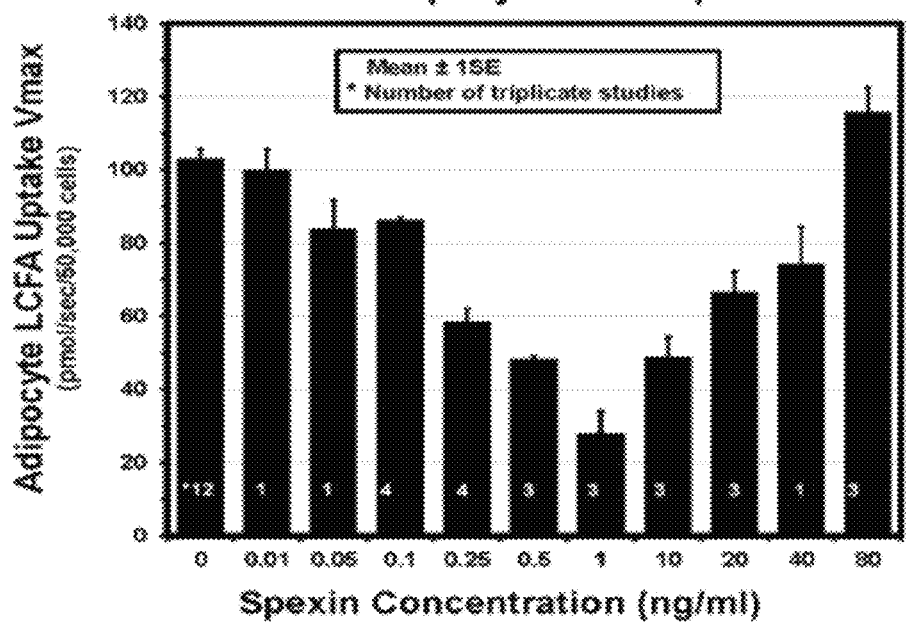
FIG. 28 shows bar graphs depicting concentration-response studies of spexin inhibition of LCFA uptake into isolated murine adipocytes demonstrate hormesis. Adipocytes isolated from DIO mice were suspended in iced PBS until ready for study. After being warmed to 37° C., the cells were then incubated for two hours in either PBS alone (controls) or PBS+Spexin at 10 different concentrations, ranging from 0.01 to 80 ng/ml. The cells were then washed, and their LCFA uptake kinetics determined. A biphasic dose response curve (hormesis) is often seen with peptide hormones whose effects are receptor mediated, when the peptide's bioactivity is tested over doses ranging several orders of magnitude.

Concentration response study of Spexin inhibition of LCFA uptake into isolated adipocytes. Adipocytes isolated from DIO mice were suspended in iced PBS until ready for study. At that point the temperature was warmed to 37° C., and the cells were then incubated for two hours in either PBS alone (controls) or PBS+Spexin at 10 different concentrations, ranging from 0.01 to 80 ng/ml. The cells were then washed, and their LCFA uptake kinetics determined. A total of 38 uptake inhibition studies have been performed in DIO mouse adipocytes, each in triplicate (FIG. 28).

Effect of Spexin on body weight and 24 hour feeding behavior in DIO rats. 24 hr food intake was reduced in the Spexin treated animals (FIG. 22A, dark circles) by Day 3. The Spexin-treated rats reduced their cumulative food intake over Days 3 and 4 by 8.2 g, or 31.5%. This effect persisted well beyond the immediate treatment period, and was apparent out to Day 7. Spexin treatment also led to a reduction in body weight (FIG. 22B), which showed a delay in onset (starting on Day 5, and considerable persistence of the effect well beyond the treatment period, to at least Day 16.

Pre-treatment baselines (FIG. 23A), on-treatment responses (FIG. 23B), early (FIG. 23C) and late (FIG. 23D) "wash-out" periods are presented. Horizontal white lines indicate "lights on". The vast majority of feeding occurs during "lights off" since rats are nocturnal feeders. At baseline, the two groups of animals demonstrated essentially identical feeding behaviors. After two days of treatment, the Spexin-dosed animals (Group 2+Spexin–red line) demonstrated a clear reduction in food consumption during the normal feeding period (lights out; 19:00 to 07:00 hours) of Day 3, and normal cessation of feeding during the light period (horizontal white bars) of Day 4. It is noteworthy that the temporal (light/dark) feeding pattern and meal frequency during the 24 hr feeding period remained normal in the peptide-treated group. However, both the meal size (total food consumed) and meal duration (time at the food bin) were both smaller in the Spexin-treated animals, who consumed approximately 30% fewer calories overall.

Figure 29:
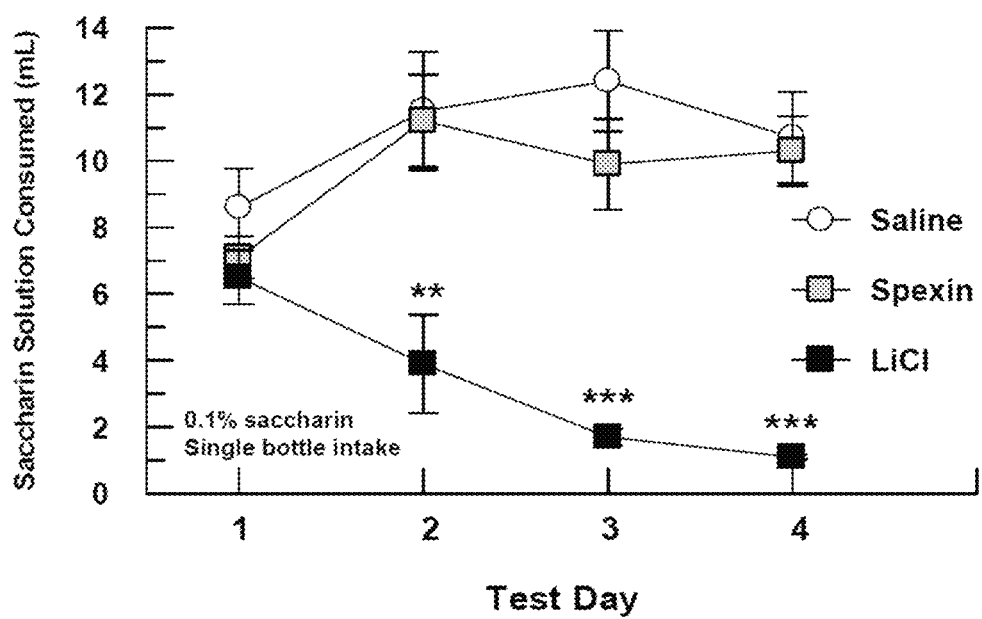
FIG. 29 shows plots conditioned taste aversion testing in adult female wistar rats. After 20 hrs of water deprivation, rats were offered a single bottle containing 0.1% sodium saccharin for 20 min, followed by an ip injection of physiological saline (n=6), 70 µg spexin/kg body weight (n=6), or 63.5 mg LiCl/kg body weight (0.15M LiCl) (n=5) after an additional 20 min. Injections were administered on test days 1-3, with no injection on the final test day. The total amount of saccharin solution consumed by the LiCl-treated animals was significantly less than consumed by either the saline or spexin-treated animals, $p<0.01$, *$p<0.001$. Data points represent mean±SEM.

Conditioned taste aversion testing in Wistar Rats. The total amount of saccharin solution consumed by the LiCl-treated animals was significantly less than consumed by either the saline or spexin-treated animals, (FIG. 29) p<0.01, *p<0.001. This reduction in consumption of the saccharine solution in the LiCl-treated animals was noted by day two of testing, and this trend persisted throughout the challenge period. No significant differences in saccharin consumption were noted in the Spexin-treated animals, indicating that the reductions in 24 hr food consumption previously seen in Spexin-treated animals were not due to aversive effects by Spexin on taste.

Discussion

Spexin was recently identified as a new peptide hormone by Mirabeau et al (2007), using a bioinformatics approach based on hidden Markov model screening to identify novel peptide-encoding sequences in the human genome [P17]. In contrast to many well-known adipokines [P12-P15], virtually nothing was known about the biological activity of Spexin at the time.

The invetors' finding that Spexin was the most down-regulated gene in obese human fat, and the demonstration of its contractile activity in an in vitro rat stomach explant model system [P17], led the inventors to conclude that Spexin can function as a adipocyte-expressed satiety factor. Therefore, the lack of Spexin expression by obese WAT can reflect the loss of a key adipokine involved in the regulation of gut activity, food consumption, energy metabolism and long chain fatty acid (LCFA) uptake and storage in adipocytes in the obese state.

Leptin plays a major role in the regulation of body weight and food consumption [P19, P31, P37], and it expression is well-known to be elevated in the obese state [P37]. One intriguing idea is that circulating Spexin and Leptin are each involved in the regulation of satiety, food intake and body weight, and may be "antagonistic" or counter-balancing hormones/adipokines whose proper "balance" is essential to the normal homeostasis of food consumption and energy metabolism. To test this relationship, Spexin and leptin concentrations were measured in human serum by immunoassays in both obese and non-obese patients. Spexin levels were found to be much lower (or undetectable) in the obese patients, whereas non-obese patients consistently had much higher levels of circulating Spexin. Circulating leptin was also measured by ELISA in the same serum samples. Leptin averaged 8.53±7.55 ng/mL in the non-obese, and 37.42±11.56 ng/mL in the obese patients (p<0.01, by 2 tailed t-test). The observed 4.44-fold increase circulating Leptin in our obese patients is equivalent to that previously described in 1996 by Considine et al [P37], who reported a 4.17 fold increase in Leptin in obese patients, where the mean±SD Leptin levels were 7.5±9.3 ng/mL (normal subjects, n=136) and 31.3±24.1 ng/mL (obese patients, n=139). The circulating levels of Spexin and Leptin in obese patients and non-obese controls exhibited a strong negative correlation.

The biological role of Spexin was also examined in energy metabolism and storage in two rodent models of diet-induced obesity. Daily intraperitoneal injections of Spexin over 10 days led to a reduction in food consumption and body weight in DIO mice, while vehicle-injected DIO mice continued to gain weight over the same period. These findings were pursued in a separate cohort of mice undergoing Spexin treatment for 18 days in metabolic chambers.

After an appropriate adaptation period, the calorimetry cage studies indicated that compared to the vehicle-treated control animals, the Spexin-treated mice demonstrated a tendency to fail to maintain adipose tissue weight over the treatment period (a negative slope for body weight data, versus the controls who continued to gain weight (positive slope), little difference in the total amounts of O2 consumed, and essentially no difference in the CO2 produced throughout the day.

However, Spexin significantly reduced the RER towards fat oxidation, particularly during the Dark cycle, where the difference in RER was highly significant. This is intriguing because the RER is normally elevated during the night-time, reflecting the preferential use of carbohydrate as a fuel source during the dark cycle, when rodents typically eat. The observed reduction in the RER during the Dark cycle appears to result from a "blocking" of the normal night-time elevation in the use of carbohydrates, with an attendant shift to lipid oxidation.

Spexin also significantly increased locomotor activity, primarily in the Z (rearing plane), which contributed to an increase in the total locomotion measured in all three planes. The reducing in the RER and the increase in Z-plane locomotor activity in the Spexin-treated animals can be either compensatory responses to the failure to maintain body weight, or an indication of increased fat oxidation. The latter can reflect Spexin-mediated diversion of LCFA away from storage in adipocytes to tissues such as liver, muscle and heart, where they are oxidized. Taken together, and without being bound by theory, Spexin can induce "fasting like" metabolism in DIO animals. These observations need to be extended for longer observation periods, direct measures of serum lipids, and by direct studies of rates of LCFA uptake and oxidation in chronically Spexin-treated animals.

The regulation of the saturable component of LCFA uptake into adipocytes has been proposed to be an important control point for body adiposity [P18]. This process has been studied extensively using isolated adipocytes from various genetic and diet-induced animal models of obesity, and obese patients. To test the role of Spexin in the regulation of LCFA uptake into adipocytes via specific membrane transporters, isolated adipocytes from DIO mice were incubated with varying concentrations of Spexin. The resulting concentration-response curve for Spexin-induced inhibition of LCFA uptake into adipocytes demonstrates classic "hormesis", presenting a bi-phasic peptide concentration-response curve [P38]. This is most often seen with peptide hormones whose effects are receptor mediated, when the peptide is tested at doses that span several orders of magnitude. Hormesis can have several mechanistic explanations, such as 1) the presence of multiple receptor subtypes with opposing effects on the cell via different second-messenger systems; 2) occupation of several peptide binding sites on a single receptor protein (analogous to cooperative binding of agonists on large protein complexes), thereby altering their interactions with down-stream messenger systems; or 3), the induction of an opposing pathway via "excess stimulation" [P38-P40].

The results demonstrate that acute in vitro incubation of isolated adipocytes from DIO mice with Spexin results in strong inhibition of LCFA, with a "bi-phasic" concentration-response curve that spans four orders of magnitude in Spexin concentrations. Taken together, Spexin is exerting these effects through a receptor-mediated process, and that Spexin can play a role in the regulation of long chain fatty acid uptake into adipocytes.

In an additional rodent model of obesity, DIO Wistar rats, daily Spexin injections significantly inhibited food intake and reduced body weight, an effect which persisted at least a week beyond the brief treatment period. The most striking result of this study was the finding that Spexin treatment reduced food consumption by approximately 30%, while preserving the animals normal, diurnal feeding behavior, with appropriate light/dark feeding patterns. What did change on Spexin treatment was the "size" (duration) of individual meals, which were smaller, leading to reduced overall consumption. No overt signs of Spexin-induced toxic effects on feeding behaviors, potentially leading to diminished total 24 hr food consumption, were observed in these studies. To confirm this impression, formal conditioned taste aversion testing was performed in a separate cohort of rats who were naïve to Spexin. In this study, varied Spexin doses were administered over several days to examine the possible aversive effects of this peptide on feeding behavior. Despite repeated dosing over the 5 day testing period, no signs of taste aversion were detected over a wide dose range in this rigorous paradigm.

To the inventors' knowledge, they are the first to demonstrate Spexin expression in WAT, to identify the almost complete absence of Spexin expression in human obese WAT, to show that Spexin has a role in the normal regulation of adipose tissue function, including uptake of LCFA, that the absence of Spexin can be a major component of the hormonal dysreguation seen in obese fat, and that repletion of circulating Spexin ca help restore normal feeding behaviors and energy balance in obese animals and man. The data strongly support that Spexin is a potent, natural satiety-inducing peptide that plays key roles in regulating feeding behavior, uptake of LCFAs into adipocytes, energy utilization and metabolism, and body weight in DIO mice and rats.

REFERENCES

P1. Yanovski, S. Z. and J. A. Yanovski, *Obesity*. N Engl J Med, 2002. 346(8): p. 591-602.

P2. Flegal, K. M., et al., *Prevalence and trends in obesity among US adults,* 1999-2000. JAMA, 2002. 288(14): p. 1723-7.

P3. Ogden, C. L., et al., *The epidemiology of obesity*. Gastroenterology, 2007. 132(6): p. 2087-102.

P4. Wang, Y., Beydoun, M A, *The obesity epidemic in the United States gender, age socio-economic, racial/ethnic and geograpical characteristics: a systematic review and meta-regression analyses*. Epidemol Reviews, 2007. 29: p. 6-28.

P5. Allison, D. B., et al., *Annual deaths attributable to obesity in the United States*. JAMA, 1999. 282(16): p. 1530-8.

P6. Oldridge, N., et al., *Goal attainment in a randomized controlled trial of rehabilitation after myocardial infarction*. J Cardiopulm Rehabil, 1999. 19(1): p. 29-34.

P7. Olshansky, S. J., et al., *A potential decline in life expectancy in the United States in the 21st century*. N Engl J Med, 2005. 352(11): p. 1138-45.

P8. Finkelstein, E. A., C. J. Ruhm, and K. M. Kosa, *Economic causes and consequences of obesity*. Annu Rev Public Health, 2005.26: p. 239-57.

P9. Bachman, K. H., *Obesity, weight management, and health care costs: a primer*. Dis Manag, 2007. 10(3): p. 129-37.

P10. Powers, K. A., S. T. Rehrig, and D. B. Jones, *Financial impact of obesity and bariatric surgery*. Med Clin North Am, 2007. 91(3): p. 321-38, ix.

P11. Bray, G. A., *Medical consequences of obesity.* J Clin Endocrinol Metab, 2004. 89(6): p. 2583-9.
P12. Wozniak, S. E., et al., *Adipose tissue: the new endocrine organ? A review article.* Dig Dis Sci, 2009. 54(9): p. 1847-56.
P13. Balistreri, C. R., C. Caruso, and G. Candore, *The role of adipose tissue and adipokines in obesity-related inflammatory diseases.* Mediators Inflamm, 2010. 2010: p. 802078.
P14. Lago, F., et al., *The emerging role of adipokines as mediators of inflammation and immune responses.* Cytokine Growth Factor Rev, 2007. 18(3-4): p. 313-25.
P15. Lago, F., et al., *Adipokines as novel modulators of lipid metabolism.* Trends Biochem Sci, 2009. 34(10): p. 500-10.
P16. Walewski, J. L., et al., *Adipocyte accumulation of long-chain fatty acids in obesity is multifactorial, resulting from increased fatty acid uptake and decreased activity of genes involved in fat utilization.* Obes Surg, 2010. 20(1): p. 93-107.
P17. Mirabeau, O., et al., *Identification of novel peptide hormones in the human proteome by hidden Markov model screening.* Genome Res, 2007. 17(3): p. 320-7.
P18. Petrescu, O., et al., *Long-chain fatty acid uptake is upregulated in omental adipocytes from patients undergoing bariatric surgery for obesity.* Int J Obes (Lond), 2005. 29(2): p. 196-203.
P19. Fan, X., M. W. Bradbury, and P. D. Berk, *Leptin and insulin modulate nutrient partitioning and weight loss in ob/ob mice through regulation of long-chain fatty acid uptake by adipocytes.* J Nutr, 2003. 133(9): p. 2707-15.
P20. Ge, F., et al., *Insulin- and leptin-regulated fatty acid uptake plays a key causal role in hepatic steatosis in mice with intact leptin signaling but not in ob/ob or db/db mice.* Am J Physiol Gastrointest Liver Physiol, 2010. 299(4): p. G855-66.
P21. Abumrad, N. A., et al., *Mechanism of long chain fatty acid permeation in the isolated adipocyte.* J Biol Chem, 1981. 256(17): p. 9183-91.
P22. Di Girolamo, M., S. Mendlinger, and J. W. Fertig, *A simple method to determine fat cell size and number in four mammalian species.* Am J Physiol, 1971. 221(3): p. 850-8.
P23. Berman, M. and M. Weiss, *User's Manual for SAAM U.S. Public Health Service Publication* 1703, D.o.H.a.H. Services, Editor 1967: Washington, D.C.
P24. Walewski, J. L., et al., *A Novel Human Peptide that Reduces Adipocyte Uptake of Long Chain Fatty Acids and Causes Weight Loss in Mice, in The Obesity Society* 2012: San Antonio, Tex.
P25. Li, X., et al., *Intracerebroventricular leptin infusion improves glucose homeostasis in lean type 2 diabetic MKR mice via hepatic vagal and non-vagal mechanisms.* PLoS One, 2011. 6(2): p. e17058.
P26. Vijayakumar, A., et al., *Targeted loss of GHR signaling in mouse skeletal muscle protects against high-fat diet-induced metabolic deterioration.* Diabetes, 2012. 61(1): p. 94-103.
P27. Liang, N. C., N. T. Bello, and T. H. Moran, *Experience with activity based anorexia enhances conditioned taste aversion learning in rats.* Physiol Behav, 2011. 102(1): p. 51-7.
P28. Ma, L., et al., *Region-specific involvement of BDNF secretion and synthesis in conditioned taste aversion memory formation.* J Neurosci, 2011. 31(6): p. 2079-90.
P29. Sun, H. D., et al., *Monoclonal antibody antagonists of hypothalamic FGFR1 cause potent but reversible hypophagia and weight loss in rodents and monkeys.* Am J Physiol Endocrinol Metab, 2007. 292(3): p. E964-76.
P30. Walewski, J., Ge, F, Gagner, M, Inabnet, W B, Pomp, A, Branch, A D, Berk, P D, *Adipocyte accumulation of long chain fatty acids in obesity is multifactorial, resulting from increased fatty acid uptake and decreased activity of genes involved in fat utilization.* Obesity Surgery (In press), 2010.
P31. Berk, P. D., et al., *Selective up-regulation of fatty acid uptake by adipocytes characterizes both genetic and diet-induced obesity in rodents.* J Biol Chem, 1999. 274(40): p. 28626-31.
P32. Petrescu, O., Fan, X Q, Bradbury, M W and Berk, P D, *Selective regulation of long chairn fatty acid uptake across adipocyte plasma membranes is a control point for body adiposity.* Gastroenterology, 2003: p. 124-A70.
P33. Stremmel, W. and P. D. Berk, *Hepatocellular influx of [14C]oleate reflects membrane transport rather than intracellular metabolism or binding.* Proc Natl Acad Sci USA, 1986. 83(10): p. 3086-90.
P34. Stump, D. D., X. Fan, and P. D. Berk, *Oleic acid uptake and binding by rat adipocytes define dual pathways for cellular fatty acid uptake.* J Lipid Res, 2001. 42(4): p. 509-20.
P35. Zhou, S., Sorrentino, D, Stump, D, Potter, B, and Berk, P D, *Adipocyte Differentiation in 3T3-L1 Fibroblasts Is Associated with Expression of A Plasma-Membrane Fatty-Acid Binding-Protein.* Hepatology, 1990(12): p. 897.
P36. Zhou, S., Stump D, Kiang, C L, isola L M, and Berk P D, *Mitochondrial aspartate aminotransferase expressed on the surface of 3T3-L J adipocytes mediates saturable fatty acid uptake.* Proc Soc Exp Biol Med, 1995. 208: p. 263-270.
P37. Considine, R. V., et al., *Serum immunoreactive-leptin concentrations in normal-weight and obese humans.* N Engl J Med, 1996. 334(5): p. 292-5.
P38. Calabrese, V., et al., *Cellular stress responses, the hormesis paradigm, and vitagenes: novel targets for therapeutic intervention in neurodegenerative disorders.* Antioxid Redox Signal, 2010. 13(11): p. 1763-811.
P39. Celik, I., et al., *Therapeutic efficacy of endostatin exhibits a biphasic dose-response curve.* Cancer Res, 2005. 65(23): p. 11044-50.
P40. Puzzo, D., L. Privitera, and A. Palmeri, *Hormetic effect of amyloid-beta peptide in synaptic plasticity and memory.* Neurobiol Aging, 2012. 33(7): p. 1484 e15-24.

What is claimed is:

1. A method of reducing fatty acid uptake in adipose tissue of a subject, the method comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby reducing fatty acid uptake in adipose tissue of the subject.

2. The method of claim 1, wherein the subject is obese or is afflicted with an obesity-associated disorder.

3. A method of reducing food intake in a subject, the method comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby reducing food intake in the subject.

4. The method of claim 3, wherein the subject is obese or is afflicted with an obesity-associated disorder.

5. A method of reducing fatty acid uptake in heart tissue or liver tissue of an obese subject or a subject afflicted with an obesity-associated disorder, the method A comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby reducing fatty acid uptake in heart tissue or liver tissue of the subject.

6. A method of promoting satiety in an obese subject or a subject afflicted with an obesity-associated disorder, the method comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby promoting satiety in the subject.

7. The method of claim 6, wherein the total amount of food consumed per day by the subject is reduced.

8. A method of treating obesity or an obesity-associated disorder in a subject, the method comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby treating obesity or an obesity-associated disorder in the subject.

9. A method of promoting weight loss in an obese subject or a subject afflicted with an obesity-associated disorder, the method comprising administering to the subject a therapeutically effective amount of a polypeptide consisting of the amino acid sequence of SEQ ID NO: 3 or SEQ ID NO: 3 A6S, or a pharmaceutically acceptable salt thereof, thereby promoting weight loss in the subject.

10. The method of any one of claims 1-9 and 4, wherein the subject is a human or non-human animal.

11. The method of claim 9, wherein the non-human animal is a mouse, rat, dog, or cat.

12. The method of any one of claims 2-9 and 4, wherein the obesity-associated disorder comprises metabolic syndrome, fatty liver disease, congestive heart failure, type II diabetes mellitus, hyperglycemia, insulin resistance, hyperinsulinemia, dyslipidemia, or a combination thereof.

13. The method of any one of claims 1-9 and 4, wherein the subject has a Body Mass Index (BMI) greater than about 25 kg/m$^2$.

14. The method of any one of claims 1-9 and 4, wherein the subject has a Body Mass Index (BMI) greater than about 30 kg/m$^2$.

15. The method of any one of claims 1-9 and 4, wherein the subject has a Body Mass Index (BMI) greater than about 35 kg/m$^2$.

16. The method of any one of claims 1-9 and 4, wherein the subject displays a decrease in adipose tissue mass after treatment with the polypeptide consisting of the amino acid sequence of SEQ ID NO: 3 or SEQ ID NO: 3 A6S.

17. The method of any one of claims 1-9 and 4, wherein the amount administered results in at least about 1 ng/ml in the serum.

18. The method of any one of claims 1-9 and 4, wherein the amount administered results in at least about 3 ng/ml in the serum.

19. The method of any one of claims 1-9 and 4, wherein the amount administered results in at least about 10 ng/ml in the serum.

20. The method of anyone of claims 1-9 and 4, wherein the amount administered results in at least about 30 ng/ml in the serum.

21. The method of any one of claims 1-9 and 4, wherein the amount administered results in at least about 100 ng/ml in the serum.

22. The method of any one of claims 1-9 and 4, wherein the amount administered results in at least about 250 ng/ml in the serum.

23. The method of any one of claims 1-9 and 4, wherein the amount administered results in at least about 500 ng/ml in the serum.

24. The method of anyone of claims 1-9 and 4, wherein the polypeptide consisting of the amino acid sequence of SEQ ID NO: 3 or SEQ ID NO: 3 A6S is administered at least once daily or at least twice daily.

25. The method of anyone of claims 1-9 and 4, wherein the polypeptide consisting of the amino acid sequence of SEQ ID NO: 3 or SEQ ID NO: 3 A6S is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 24 weeks, or for at least 48 weeks.

26. The method of any one of claims 1-9 and 4, wherein the polypeptide consisting of the amino acid sequence of SEQ ID NO: 3 or SEQ ID NO: 3 A6S is administered for at least 1 year, for at least 1.5 years, for at least 2 years, for at least 2.5 years, or for at least 5 years.

\* \* \* \* \*

SEQUENCE LISTING

<160> NUMBER OF SEQ ID NOS: 33

<210> SEQ ID NO 1
<211> LENGTH: 116
<212> TYPE: PRT
<213> ORGANISM: Homo sapiens

<400> SEQUENCE: 1

Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Leu Pro Glu Arg Arg Ser Pro Asn Pro Gln Leu Leu Thr
65                  70                  75                  80

Ile Pro Glu Ala Ala Thr Ile Leu Leu Ala Ser Leu Gln Lys Ser Pro
                85                  90                  95

Glu Asp Glu Glu Lys Asn Phe Asp Gln Thr Arg Phe Leu Glu Asp Ser
                100                 105                 110

Leu Leu Asn Trp
            115

<210> SEQ ID NO 2
<211> LENGTH: 638
<212> TYPE: DNA
<213> ORGANISM: Homo sapiens

<400> SEQUENCE: 2
ctgacaagat gtccctgtgg actcccaaac tctactccag atggggaggt gcccttaaca      60
ccaagatttt aaaagctcca atttcagagc aagagtcgaa aactcacaga taaagttata     120
gttatttcag ggttctgaaa agacgcagaa catgaaggga ctcagaagtc tggcagcaac     180
aaccttggct cttttcctgg tgtttgtttt cctgggaaac tccagctgcg ctccgcagag     240
actgttggag agaaggaact ggactcctca agctatgctc tacctgaaag gggcacaggg     300
tcgccgcttc atctccgacc agagccggag aaaggacctc tccgaccggc cactgccgga     360
aagacgaagc ccaaatcccc aactactaac tattccggag gcagcaacca tcttactggc     420
gtcccttcag aaatcaccag aagatgaaga aaaaaacttt gatcaaacca gattcctgga     480
agacagtctg cttaactggt gaaaatatac tggattatgt ttaattatgg ttctattctc     540
tttgaaaaca tgaaccatgt gaataaaacc tttggaccct ttttaaaaaa aaaaaaaaaa     600
aaaaaaaaaa aaaaaaaaaa aaaaaaaaaa aaaaaaaa                             638

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Trp Thr Pro Gln Ala Met Leu Tyr Leu Lys Gly Ala Gln
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 4
atcccaaatc aaagcaccag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggctttgtga actgggatgt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcagaaagcc cgtgagaagt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggcctcaa cagaaccatc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacctgtct gggctacatt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcctgatgtc ccattgaact                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 10
ctggggagtt caggatgtgt                                                      20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcagcctgct tcaaggaaat                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acaccctgga gaacaccatc                                                      20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgtcgagca tggtctggaa t                                                    21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagcttctcc ccagactcac                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgttgggca agctctgaat                                                      20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
gtgccactga atgcatcaac                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggttttggga atcaggaggt                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caaggcaaac ttggagaagg                                                   20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggcagttca tccagaggt                                                    19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcactgaag gagaaggaga                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggccgtaca catagtgctt                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 22
ccagctacca tgtcccagat                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaggactga ccacttgtgc                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agttctctgt ggcccatgac                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggcatctggt cgtagacctt                                               20

<210> SEQ ID NO 26
<211> LENGTH: 116
<212> TYPE: PRT
<213> ORGANISM: Homo sapiens

<400> SEQUENCE: 26

Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Leu Pro Glu Arg Arg Ser Pro Asn Pro Gln Leu Leu Thr
65                  70                  75                  80

Ile Pro Glu Ala Ala Thr Ile Leu Leu Ala Ser Leu Gln Lys Ser Pro
                85                  90                  95

Glu Asp Glu Glu Lys Asn Phe Asp Gln Thr Arg Phe Leu Glu Asp Ser
            100                 105                 110

Leu Leu Asn Trp
        115

```
<210> SEQ ID NO 27
<211> LENGTH: 120
<212> TYPE: PRT
<213> ORGANISM: Pan troglodytes

<400> SEQUENCE: 27

Met Lys Gly Leu Arg Ser Leu Ala Ala Thr Thr Leu Ala Leu Phe Leu
1               5                   10                  15

Val Phe Val Phe Leu Gly Asn Ser Ser Cys Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Leu Pro Glu Arg Arg Ser Pro Asn Pro Arg Leu Leu Thr
65                  70                  75                  80

Ile Pro Glu Ala Ala Thr Ile Leu Leu Ala Ser Leu Gln Lys Ser Pro
                85                  90                  95

Glu Val Gln Ser Ile Ser Asn Cys Ser Ala Asp Ala Arg Leu Ile Gly
            100                 105                 110

Ile His Arg Ala Phe Val Lys Gly
        115                 120

<210> SEQ ID NO 28
<211> LENGTH: 134
<212> TYPE: PRT
<213> ORGANISM: Canis lupus

<400> SEQUENCE: 28

Met Lys Gly Leu Arg Ser Leu Val Ala Thr Thr Leu Ala Leu Phe Leu
1               5                   10                  15

Val Phe Ser Phe Leu Gly Ser Ser Ser Ala Pro Gln Gly Leu Phe
            20                  25                  30

Glu Arg Arg Asn Trp Thr Pro Gln Ser Met Leu Tyr Leu Lys Gly Ala
        35                  40                  45

Gln Gly Arg Arg Phe Ile Ser Asp Gln Ser Arg Lys Lys Asp Pro Ser
    50                  55                  60

Asp Arg Pro Pro Glu Arg Arg Ser Pro Asn Pro Gln Leu Leu Thr
65                  70                  75                  80

Leu Pro Glu Ala Ala Leu Leu Thr Ser Leu Gln Lys Pro Gln
                85                  90                  95

Glu Glu His Ser Asp Asp Ser Val Lys Lys Ala Glu Cys Asp Tyr Gly
            100                 105                 110

Pro Glu Ser Asn Asn Lys Asn Cys Asn Asn Trp Asn Asn Thr Gly Arg
        115                 120                 125

Ser Thr Met Cys Gln Met
    130

<210> SEQ ID NO 29
<211> LENGTH: 116
<212> TYPE: PRT
<213> ORGANISM: Bos taurus

<400> SEQUENCE: 29

Met Lys Gly Phe Lys Ser Leu Val Val Met Thr Leu Thr Leu Phe Leu
1               5                   10                  15

Val Phe Ser Phe Met Gly Asn Cys Asn Ser Ala Pro Gln Arg Leu Phe
            20                  25                  30
```

-continued

Glu Arg Arg Asn Trp Thr Pro Gln Ala Met Leu Tyr Leu Lys Gly Ala
    35                  40                  45

Gln Gly Arg Arg Phe Leu Ser Asp Gln Ser Arg Lys Asp Leu Ser
50                  55                  60

Asp Arg Pro Pro Leu Glu Arg Arg Ser Pro Asn Ser Gln Gln Leu Thr
65                  70                  75                  80

Leu Pro Glu Ala Ala Ala Val Leu Leu Ala Phe Leu Gln Lys Pro Gln
                85                  90                  95

Glu Ala Gly Asp Glu Asn Leu Asp Gln Thr Arg Phe Leu Glu Asp Ser
            100                 105                 110

Leu Leu Asn Trp
        115

<210> SEQ ID NO 30
<211> LENGTH: 77
<212> TYPE: PRT
<213> ORGANISM: Mus musculus

<400> SEQUENCE: 30

Met Leu Tyr Leu Lys Gly Ala Gln Gly Arg Arg Phe Leu Ser Asp Gln
1               5                   10                  15

Ser Arg Arg Lys Glu Leu Ala Asp Arg Pro Pro Glu Arg Arg Asn
            20                  25                  30

Pro Asp Leu Glu Leu Leu Thr Leu Pro Glu Ala Ala Ala Leu Phe Leu
        35                  40                  45

Ala Ser Leu Glu Lys Ser Gln Lys Gly Ala Asp Glu Gly Gly Asn Phe
    50                  55                  60

Asp Lys Ser Glu Leu Leu Glu Asp Arg Leu Phe Asn Trp
65                  70                  75

<210> SEQ ID NO 31
<211> LENGTH: 116
<212> TYPE: PRT
<213> ORGANISM: Rattus norvegicus

<400> SEQUENCE: 31

Met Lys Gly Pro Ser Ile Leu Ala Val Ala Leu Ala Leu Leu Leu
1               5                   10                  15

Val Leu Ser Val Leu Glu Asn Ser Ser Gly Ala Pro Gln Arg Leu Ser
            20                  25                  30

Glu Lys Arg Asn Trp Thr Pro Gln Ala Met Leu Tyr Leu Lys Gly Ala
        35                  40                  45

Gln Gly His Arg Phe Ile Ser Asp Gln Ser Arg Lys Glu Leu Ala
    50                  55                  60

Asp Arg Pro Pro Glu Arg Arg Asn Pro Asn Leu Gln Leu Leu Thr
65                  70                  75                  80

Leu Pro Glu Ala Ala Ala Leu Phe Leu Ala Ser Leu Glu Lys Pro Gln
                85                  90                  95

Lys Asp Glu Gly Gly Asp Phe Asp Lys Ser Lys Leu Leu Glu Asp Arg
            100                 105                 110

Arg Phe Tyr Trp
        115

<210> SEQ ID NO 32
<211> LENGTH: 14
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 32

Asn Trp Thr Pro Gln Ala Met Leu Tyr Leu Lys Gly Ala Gln
1               5                   10

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      majority sequence
<220> FEATURE:
<221> NAME/KEY: MOD_RES
<222> LOCATION: (98)..(98)
<223> OTHER INFORMATION: Asp, Val, Glu, Ala, Gly or absent
<220> FEATURE:
<221> NAME/KEY: MOD_RES
<222> LOCATION: (99)..(99)
<223> OTHER INFORMATION: Glu, Gln, His, Gly, Ala or absent

<400> SEQUENCE: 33

Met Lys Gly Leu Arg Ser Leu Ala Ala Thr Thr Leu Ala Leu Phe Leu
1               5                   10                  15

Val Phe Ser Phe Leu Gly Asn Ser Ser Ser Ala Pro Gln Arg Leu Leu
            20                  25                  30

Glu Arg Arg Asn Trp Thr Pro Gln Ala Met Leu Tyr Leu Lys Gly Ala
        35                  40                  45

Gln Gly Arg Arg Phe Ile Ser Asp Gln Ser Arg Arg Lys Asp Leu Ser
    50                  55                  60

Asp Arg Pro Pro Glu Arg Arg Ser Pro Asn Pro Gln Leu Leu Thr
65                  70                  75                  80

Leu Pro Glu Ala Ala Ala Leu Leu Leu Ala Ser Leu Gln Lys Ser Gln
                85                  90                  95

Glu Xaa Xaa Asp Glu Gly Gly Phe Asp Asp Ser Arg Leu Leu Glu Asp
            100                 105                 110

Ser Leu Leu Asn Trp
            115
```